US008852928B2

(12) United States Patent
Emelyanov et al.

(10) Patent No.: US 8,852,928 B2
(45) Date of Patent: Oct. 7, 2014

(54) LEXA-BASED CHEMICAL-INDUCIBLE GENE EXPRESSION SYSTEM FOR USE IN TRANSGENIC ANIMALS

(75) Inventors: Alexander Emelyanov, Singapore (SG); Sergey Parinov, Singapore (SG); Nam-Hai Chua, New York, NY (US)

(73) Assignee: Temasek Life Sciences Laboratory Limited, Singapore (SG)

( * ) Notice: Subject to any disclaimer, the term of this patent is extended or adjusted under 35 U.S.C. 154(b) by 511 days.

(21) Appl. No.: 12/663,323

(22) PCT Filed: Jul. 2, 2008

(86) PCT No.: PCT/SG2008/000237
§ 371 (c)(1),
(2), (4) Date: Dec. 7, 2009

(87) PCT Pub. No.: WO2009/008837
PCT Pub. Date: Jan. 15, 2009

(65) Prior Publication Data
US 2010/0269182 A1  Oct. 21, 2010

Related U.S. Application Data

(60) Provisional application No. 60/948,250, filed on Jul. 6, 2007.

(51) Int. Cl.
C12N 15/00 (2006.01)
C07H 21/02 (2006.01)
C07H 21/04 (2006.01)
C12N 15/85 (2006.01)
A01K 67/027 (2006.01)
A01K 67/00 (2006.01)

(52) U.S. Cl.
CPC ............ *C12N 15/85* (2013.01); *C07K 2319/71* (2013.01); *C12N 2800/40* (2013.01); *C07K 2319/715* (2013.01); *A01K 2227/40* (2013.01); *A01K 2217/15* (2013.01); *A01K 2267/03* (2013.01); *C12N 15/8509* (2013.01); *A01K 67/0275* (2013.01); *C12N 2830/002* (2013.01); *A01K 2217/052* (2013.01); *A01K 2217/203* (2013.01); *C07K 2319/80* (2013.01); *A01K 2267/0393* (2013.01)
USPC ...................................... 435/320.1; 536/23.4

(58) Field of Classification Search
USPC ...................................... 435/320.1; 536/23.4
See application file for complete search history.

(56) References Cited

U.S. PATENT DOCUMENTS 5,561,053 A * 10/1996 Crowley ....................... 435/69.1
6,784,340 B1 * 8/2004 Aoyama et al. .............. 800/290

2002/0182698 A1 * 12/2002 O'Malley et al. ............ 435/199
2004/0146906 A1 * 7/2004 Robinson et al. ................ 435/6
2009/0131272 A1 * 5/2009 Parinov et al. ................. 506/10

FOREIGN PATENT DOCUMENTS

WO    97/38117 A1    10/1997
WO    02/066615 A2    8/2002

OTHER PUBLICATIONS

Weil et al. Transposition of maize Ac/Ds transposable elements in the yeast *Saccharomyces cerevisiae*. Nature genetics 26:187-190, 2000.*
Burcin et al. Adenovirus-mediated regulatable target gene expression in vivo. Proc. Natl. Acad. Sci. USA 96:355-360, 1999.*
Emelyanov et al. Trans-kingdom transposition of the maize Dissociation element. Genetics 174:1095-1104, 2006.*
Emelyanov, A. et al. "Mifepristone inducible. LexPR system to drive and control gene expression in transgenic zebrafish," Developmental Biology, 2003, vol. 320, pp. 113-121.
Padidak M. et al., "Chemical-inducible, ecdysone receptor-based gene expression system for plants," Transgenic Research, 2003, vol. 12, pp. 101-109.
Ngan, Elly S.W. et al., "The Mifepristone-Inducible Gene Regulatory System in Mouse Models of Disease and Gene Therapy," Seminars in Cell and Developmental Biology, Apr. 1, 2002, vol. 13, No. 2, pp. 143-149, © 2002.
Ngan, Elly S.W. et al., "Inducible Expression of FGF-3 in Mouse Mammary Gland," PNAS, Aug. 20, 2002, vol. 99. No. 17, pp. 11187-11192.
Bo, J. et al., "Cardiac-Specific and Ligand-Inducible Target Gene Expression in Transgenic Mice," Journal of Molecular and Cellular Cardiology, Apr. 1, 2005, vol. 38, No. 4, pp. 685-691, © 2005 Elsevier Ltd.
Shah, V.R.et al., "Double-Inducible Gene Activation System for Caspase 3 and 9 in Epidermis," GENESIS: The Journal of Genetics and Development, vol. 45, No. 4, Apr. 1, 2007, pp. 194-199, © Wiley-Liss, Inc.
Lai, Sen-Lin et al., "Genetic Mosaic with Dual Binary Transcriptional Systems in Drosophila," Nature Neuroscience, Apr. 2, 2006, vol. 9, No. 5; pp. 703-709, © Nature Publishing Group.
Szuets, D et al., "LexA Chimeras Reveal the Function of Drosophila Fos as a Context-Dependent Transcriptional Activator," PNAS, May 9, 2000, vol. 97, No. 10, pp. 5351-5356.
Burcin, M et al., "Adenovirus-Mediated Regulable Target Gene Expression in Vivo," Proceedings of the National Academy of Sciences, Jan. 1, 1999, vol. 96, pp. 355-360.
Hanife, E. et al., "Siriall-Molecule Regulation of Zebrafish Gene Expression," Nature Chemical Biology, Jan. 21, 2007, vol. 3, No. 3, pp. 154-155, © 2007 Nature Publishing Group.

(Continued)

Primary Examiner — Quang Nguyen
(74) Attorney, Agent, or Firm — Rothwell, Figg, Ernst & Manbeck P.C.

(57) ABSTRACT

The present invention relates generally to chemical-inducible system and to methods of use in transgenic animals. More specifically, the present invention relates to a chimeric transcription factor that binds to a ligand and functions in ligand-dependent manner to induce expression of genes of interest under the control of a synthetic operator-promoter sequence. The expression of genes of interest can be tightly controlled by adding or removing the ligand.

17 Claims, 15 Drawing Sheets

(56) References Cited

OTHER PUBLICATIONS

Davison, J.M., "Transactivation from Gal4-VP16 Transgenic Insertions for Tissue-Specific Cell Labeling and Ablation in in Zebrafish," Developmental Biology, Apr. 5, 2007, vol. 304, No. 2, pp. 811-824, © 2007 Elsevier Inc.

Nicholson, L et al., "Spatial and Temporal Control of Gene Expression in Drosophila Using the Inducible GeneSwitch GAL4 System. I. Screen for Larval Nervous System Drivers," GENETICS, Jan. 1, 2008, vol. 178, No. 1, pp. 215-234, © 2008 by the Genetics Society of America.

* cited by examiner

B

DRIVER g/ap: LexPR/LexOP:EGFP4  X  EFFECTOR LexOP: CHERRY/cry: ECFP1

C

DRIVERg/ap: LexPR/LexOP:ECFP4  X  EFFECTOR LexOP: CHERRY/cry: ECFP1

LEXA-BASED CHEMICAL-INDUCIBLE GENE EXPRESSION SYSTEM FOR USE IN TRANSGENIC ANIMALS

CROSS-REFERENCE TO RELATED APPLICATIONS

The present application is a national stage filing under 35 U.S.C. §371 of PCT/SG2008/000237, filed 2 Jul. 2008 and claims priority to U.S. provisional patent application Ser. No. 60/948,250, filed 6 Jul. 2007, each application incorporated herein by reference.

BACKGROUND OF THE INVENTION

The present invention relates generally to chemical-inducible system and to methods of use in transgenic animals. More specifically, the present invention relates to a chimeric transcription factor that binds to a ligand and functions in ligand-dependent manner to induce expression of genes of interest under the control of a synthetic operator-promoter sequence. The expression of genes of interest can be tightly controlled by adding or removing the ligand.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

Transgenic organisms that express or misexpress various transgenes are commonly generated for biological research and biotechnology. However it is often problematic to generate or study the transgenic organisms that carry and express certain transgenes. For example, i) expression of a transgene which causes lethality or infertility makes it is impossible to create transgenic animals carrying a given transgene; ii) the developmental or other effects caused by expression of a given transgene in the earlier development makes it is impossible or problematic to unambiguously study the effects that occur later in development; and iii) continuous expression of the transgene after a certain time point may be undesirable.

Also, many developmentally regulated genes are re-deployed at different times of development in different cell types. Therefore, in order to dissect their unique functions in each context in a precise manner, methods for manipulation and spatiotemporal control of gene expression are essential. Using a simple promoter to drive target gene expression is the most commonly used strategy in transgenic fish and other vertebrate species. However, the number of well-characterized tissue-specific promoters is very limited. Furthermore, constitutive and ubiquitous expression is often not adequate or disadvantageous, for example, when gene expression at earlier stages of development causes severe effects, which obscure the roles of this gene at later stages or when expression of the transgene cause infertility or premature lethality, hindering generation and maintenance of transgenic animals.

One way to address these problems is by generating two independent transgenic lines, the "effector (target)" line, carrying a transcriptionally silent gene of interest, and the "driver" line, expressing a transcription activator which can induce expression of the gene of interest in double transgenic hybrid driver/effector animals (e.g. Gal4/UAS system (Davison et al., 2007; Scott et al., 2007)). The use of gene- and enhancer-trap screening can allow the generation of a large number of driver lines with various expression patterns of a transcription activator (Kotani et al., 2006; Parinov et al., 2004; Scott et al., 2007). However, it is not feasible to cover all required spatiotemporal patterns even in large-scale enhancer-trap screens. Therefore, improved techniques that permit switching gene expression on and off when required, would allow more experimental flexibility and better control of expression.

Heat shock promoters have been utilized in fish to induce ubiquitous gene expression at specific time points by exposure to heat (Bajoghli et al., 2004). For example, heat-inducible expression of the dominant-negative form of the FGF receptor driven by a zebrafish hsp70 was used to study the roles of Fgf signaling during regeneration (Lee et al., 2005; Lepilina et al., 2006). However, heat shock promoters allow relatively low inducibility and lack spatial control of transgene expression. Also, using lasers to induce cell-specific gene expression (Halloran et al., 2000) is technically difficult and applicable only on a small scale.

Non-inducible gene expression systems utilizing the LexA DNA binding domain have been previously used in invertebrates and in vertebrate cell cultures (Hoshino et al., 2004; Lai and Lee, 2006; Nettelbeck et al., 1998; Szuts and Bienz, 2000).

Chemical-inducible techniques allow temporal control of gene expression combined with the spatial control of tissue-specific promoters. Furthermore, binary inducible expression systems allow a combination of inducibility with the power of enhancer trap screening (Nicholson et al., 2008). Chemical inducible expression systems have been previously applied to study gene functions at various stages of development. For example, "tet-on" inducible system was used to dissect multiple roles of genes during chicken somitogenesis, which would not be possible using a conventional promoter because the phenotypes caused by the early expression of some genes precluded studying the effects at the later stages (Watanabe et al., 2007). Mifepristone-inducible expression of FGF-3 during postnatal development, and in the adult tissues was used to assess the complex temporal roles of the FGF signaling in organ development, adult physiology and tumor development in transgenic mice, because manipulation of FGF signaling at earlier stages caused abnormal development and neonatal lethality (Ngan et al., 2002; Zhao et al., 2001). In another example, inducible expression of dominant negative thyroid hormone receptor was used to determine the developmental periods within which thyroid hormone controls specific aspects of *Xenopus* morphogenesis (Das and Brown, 2004). Inducible expression used in this example also helped to circumvent the severe developmental abnormalities and death caused by expression of the dominant negative receptor using conventional promoters.

Hormone-responsive transcriptional activators have been used previously in ligand-inducible strategies to regulate target gene expression. For example, a chimeric transactivator consisting of a mutated progesterone receptor ligand-binding domain fused to the HSV VP16 transactivation domain and the yeast GAL4 DNA-binding domain (DBD) has been shown to transactivate UAS-controlled target genes only in the presence of mifepristone/RU-486 (Wang et al., 1994). A similar chimeric transactivator GLp65, which contains the activation domain of the human p65 protein (instead of VP16), has been used for inducible expression of target genes in mammalian cells (Burcin et al., 1999). Mifepristone-inducible GAL4/UAS-based techniques have been successfully used in transgenic mice (Kellendonk et al., 1999; Ngan et al., 2002; Pierson et al., 2000; Wang et al., 1997a; Zhao et al., 2001), in *Xenopus* (Das and Brown, 2004) and in *Drosophila* (Nicholson et al., 2008). Although the Gal4/UAS system has been widely utilized previously, some reports suggest that high level of GAL4 expression can be toxic and causes developmental defects (Habets et al., 2003; Kramer and Staveley, 2003; Scott et al., 2007).

One alternative to GAL4/UAS-based systems is to use the DNA-binding domain from the bacterial repressor LexA coupled with the specific operator DNA fragment/s. Since the structure of LexA DBD does not resemble those of eukaryotic transcription factors (Oertel-Buchheit et al., 1992), it is less likely to bind to the cis-elements of endogenous promoters. It was previously utilized in estradiol-inducible gene expression systems, developed for use in transgenic plants, since plants lack endogenous estrogen hormones (Guo et al., 2003; Zuo et al., 2000). This expression system caused no apparent toxicity in transgenic plants.

Although several chemical-inducible systems have been developed for use in mammals and mammalian cells, there has been only one recent publication in zebrafish. In this report, a tebufenozide-inducible system was tested in transient assay (Esengil et al., 2007). It utilized a chimeric transcription factor containing GAL4 DNA-binding and dimerization domains, VP16 activation domain and ecdysone receptor (EcR) ligand-binding domain. However, this chemical-inducible system has not been used yet for generation of true transgenic animals or for generating driver/effector lines, so the efficacy of this system is not clear.

Thus, there is still a need for new genetic systems that would make it possible to effectively control transgene expression by switching it on or off when required and to drive the expression only in the desired tissues or cells.

SUMMARY OF THE INVENTION

The present invention generally provides a chemical-inducible system and to methods of use in transgenic animals or in animal cells. More specifically, the present invention provides a chimeric transcription factor that binds to a ligand and functions in ligand-dependent manner to induce expression of genes of interest under the control of a synthetic operator-promoter sequence. The expression of genes of interest can be tightly controlled by adding or removing the ligand.

Thus, in a first aspect, the present invention provides a chimeric transcription factor (also referred to herein as a transactivator) that comprises a DNA binding domain of the bacterial LexA repressor protein, a ligand binding domain of the human progesterone receptor and an activation domain. In one embodiment, the ligand binding domain is a truncated ligand binding domain of the human progesterone receptor. Truncated ligand binding domain corresponds to amino acids 640-914 of the native hPR protein. "Truncated" refers to C-terminal deletion of the 19 amino acid of the hPR-LBD (Wang et al., 1997b). In one embodiment, the activation domain is the activation domain of the p65 subunit of human NF-κB (Burcin et al., 1999). In another embodiment, the activation domain is the transactivation domain of the HSV virion protein VP16. Other examples of activation domains that may be used include, but are not limited to, activation domains of adenovirus E1A, Epstein-Barr virus EBNA 2, yeast Gal4, mammalian Sp1, Oct1 and Oct2, and the like. The chimeric transcription factor binds to a ligand, and functions in a ligand-dependent manner to induce expression of a gene of interest placed under the control of a synthetic operator-promoter sequence that harbors LexA binding sites. In one embodiment, the ligand is the synthetic steroid mifepristone (RU 486).

In a second aspect, the present invention provides, a transactivation construct containing the chimeric transcription factor operatively linked to a promoter or to a splice acceptor sequence. In one embodiment, the transactivation construct containing the chimeric transcription factor is operatively linked to a promoter. In one embodiment, the promoter is one which drives expression of the transactivator and is an enhancer trap promoter. In one embodiment, the enhancer trap promoter is zebrafish keratin8 promoter (Parinov et al., 2004). In another embodiment, the enhancer trap promoter is any other eukaryotic promoter that produces desirable trapping. Practically any eukaryotic promoter is capable of responding to enhancers (although with varying efficiency) and therefore can be used as enhancer trap promoter. Examples of promoters include, but are not limited to, EF1α promoter, hsp, and the like (Balciunas et al., 2004; Scott et al., 2007). In one embodiment, the promoter is an organ specific promoter, or a tissue specific promoter or a cell specific promoter (e.g. GFAP, Flk-1, GATA-1, Rag2, and the like). In one embodiment, the promoter is a developmentally regulated promoter. Thus, in accordance with the present invention any promoter can be used. The choice of promoter depends on the experimental goal. In another embodiment, the transactivation construct containing the chimeric transcription factor is operatively linked a splice acceptor sequence. Splice acceptor sequences are well known to skilled artisans.

In a third aspect, the present invention provides expression constructs for use in expressing genes in transgenic animals or in cells of animals. In one embodiment, the construct comprises a synthetic operator-promoter operably linked to a gene (also sometimes referred to as a coding sequence). In one embodiment, the operator is a synthetic LexA operator operatively linked to a promoter. In one embodiment, the synthetic LexA operator is a ColE1 operator. In another embodiment, the LexA operator is a ColE1 operator that is modified or changed to a different sequence containing LexA binding sites (e.g., lexA, recA operator sequences or consensus). In one embodiment, the synthetic LexA operator contains one or more, preferably two or more LexA binding sites. In another embodiment, the number of the operator sequences or LexA binding sites can be changed to optimize the performance. In one embodiment, the promoter is a minimal promoter. The minimal promoter is used to minimize the background expression in the absence of the transactivator. However, the use of alternative promoters in the expression construct is contemplated. In one embodiment, the gene is a marker gene or a reporter gene. In another embodiment, the gene is a gene of interest, i.e., a gene which is desired to express in a transgenic animal. In one embodiment, the transgenic animal is a non-human transgenic animal. In another embodiment, the transgenic animal is a transgenic fish. In one embodiment, the animal cells are non-human animal cells. In another embodiment, the animal cells are human cells. In another embodiment, this system can potentially be applied in non-animal cells and organisms, for example plant cells.

In a fourth aspect, the present invention provides a system for expressing genes in transgenic animals or in cells of animals. In one embodiment, the system comprises a LexA driver construct and an effector (also referred to herein as target) construct. The LexA driver construct comprises the transactivation construct. In another embodiment, the LexA driver construct also includes a reporter and this construct is also referred to herein as a LexA driver-reporter construct. The LexA driver-reporter construct comprises the transactivation construct and expression construct in which the gene is a marker gene or a reporter gene. In one embodiment, the effector construct comprises the expression construct in which the gene is a gene of interest. In one embodiment, the LexA driver construct and the effector construct are in separate nucleic acid molecules. In another embodiment, the LexA driver construct and the effector construct are in the same nucleic acid molecule.

In a fifth aspect, the present invention provides a method of expressing genes in transgenic animals or in cells of animals. In one embodiment, the method comprises preparing transgenic animals that contain the LexA driver construct and the effector construct. In one embodiment, a first transgenic animal is prepared to contain the LexA driver construct and a second transgenic animal is prepared to contain the effector construct. Crossing the first and second transgenic animals or their progeny create a third transgenic animal containing both the LexA driver construct and the effector construct. In another embodiment, a transgenic animal is prepared that contains the LexA driver construct and the effector construct using a nucleic acid molecule that contains both constructs. In another embodiment, the method comprises preparing cells of animals that contain the LexA driver construct and the effector construct. In accordance with this aspect of the invention, the expression of the gene in the transgenic animal or animal cell is controlled by the addition of a ligand for the human progesterone receptor. Expression of the gene can be switched on and off by adding or removing the ligand.

BRIEF DESCRIPTION OF THE FIGURES

FIG. 1A: A modular expression system utilizing separate driver and effector cassettes. In double transgenic fish carrying both cassettes, expression of the gene of interest is activated in trans by the LexPR transactivator produced from the driver (driver-reporter) construct. FIG. 1B: One cassette system. The LexPR transactivator gene and a gene of interest are cloned into the same Ds transposon vector (driver-effector). Although, this binary cassette lacks a reporter gene, it can be introduced directly into the transgenic fish homozygous for a separate reporter cassette. It is preferable to use a different transposon system (e.g. Tol2, indicated by white arrowheads) for the reporter cassette to avoid the unwanted activation by Ac transposase.

FIG. 4A: Strong expression in the cell layer at the bottom of the ear (possibly sensory patches), at the olfactory bulb region (ob) and in discrete cells of midbrain (head, dorsal view). FIG. 4B: Strong expression in the diencephalon (d) and cerebellum (c), lens and in discrete cells of the tectum (t) and hindbrain (hb) (head, dorsal view). FIG. 4C: Expression in the olfactory bulbs (head, ventral view). FIG. 4D: Specific expression in a subset of muscle cells in the somites (lateral view above yolk extension).

FIG. 6A: Expression pattern of the LexPR transactivator RNA at 48 hpf. The strongest expression is found in the cell layer at the bottom of the otic capsule (possibly sensory patches) and at the olfactory bulb region. The diffused expression in the dorsal brain appears quite strong on the lateral view due to specimen thickness, the expression is actually weak as seen on the dorsal view. The 72 hpf LexPR expression pattern is similar (image not shown). FIGS. 6C-6G: EGFP reporter transcript 1 (FIG. 6C), 3 (FIG. 6D), 6 (FIG. 6E), 9 (FIG. 6F) and 24 (FIG. 6G) hours after induction with 1 µM mifepristone (RU486) at 48 hpf stage onwards. No background EGFP transcript was observed without mifepristone (FIG. 6B). The EGFP fluorescence pattern of the transgenic driver-reporter line used for this experiment is shown on FIG. 4A.

FIG. 8A (lateral view) and FIG. 8C (dorsal view) shows several F2 fish from an offspring of the driver line #4 female and the effector line #1 male. FIG. 8B is a progeny of the independent Driver line #6 crossed with the same Effector line #1. There is strong expression in the forebrain (arrowhead) and in the a few segments of the hindbrain (large arrows).

FIG. 9A: shows three different F2 fish randomly taken from an offspring of the Driver line #26 female and the Effector line #2 male. FIG. 9B: progeny of the same Driver line #26 crossed with the different Effector line #1.

FIG. 10A: Assembled image of the whole fish produced by stitching several overlapped exposures.

FIG. 11A: Strong expression is in the cell layer at the bottom of the ear (possibly sensory patches), at the olfactory bulb region and in various neurons (head, dorsal view). FIG. 11B: Expression is detected in the specific subtype of muscle cells (lateral view). Bottom panel is a combined image showing both reporters EGFP and mCherry: green indicates excess of EGFP fluorescence, red—excess of mCherry fluorescence, yellow—similar levels of mCherry and EGFP fluorescence (Notice that these colors do not constitute true molar ratios between the reporters). Although, most positive cells express both reporters, there are cells that yield brighter mCherry fluorescence than the EGFP and vice-versa. mCherry fluorescence is not detected in the effector lines containing only the effector cassette upon treatment with mifepristone. No background EGFP/mCherry fluorescence was detected in the control populations of double transgenic fish that were not treated with mifepristone (not shown). Images were captured at 96 hours post fertilization.

FIG. 12a: 24 hpf, no induction. FIG. 12b-12c: 24 hpf; 1 µM mifepristone treatment from 10 hpf onwards. GFP fluorescence can be observed in the skin epithelia, the notochord sheath (lateral view, FIG. 12b), in the forebrain (ventral view, FIG. 12c), all of these organs are abnormal. FIG. 12d: 4 dpf, 1 µM mifepristone treatment 10 hpf onward, lateral view. Notochord, brain and cranial skeleton are severally affected by the EGFP-Kras$^{V12}$ expression. Skin epithelial cells lost epithelial cell shape, became globular, formed clusters. FIG. 12e: Transformation of the sheath cells surrounding the notochord. The top and the middle panel shows the notochord of 4 dpf fish treated with 1 µM mifepristone from 10 hpf onwards. Bottom panel shows notochord of the untreated control. FIG. 12f: Transgenic fish harboring the unmodified driver-reporter construct pDs(krt8:LPR-LOP:G4) containing EGFP gene under control of the LexOP. 24 dpf, 1 µM mifepristone treatment starting at 10 hpf, showing EGFP expression in the skin epithelia. The skin cells have typical epithelial shape and uniformly cover the entire body. FIG. 12g: 4 dpf, 1 µM mifepristone treatment 1 dpf onward. Due to later induction there is much less developmental abnormalities, but the phenotype of the epithelial skin cells is pronounced.

FIG. 13a: Strong expression of non-inducible Gal4/UAS system in true transgenic fish at early developmental stages (less than 24 hpf) caused serious abnormalities that became evident later in development. FIGS. 13d-13f: Mifepristone-induced Gal4/UAS expression caused less pronounced developmental abnormalities compared to the non-inducible system when induced before 24 hpf. In some transgenic fish the phenotypes were subtle (FIG. 13g) and some survived to maturity. Induction after 24 hpf did not cause serious effects although sometimes affected individual cell morphology. For both non-inducible and inducible Gal4/UAS-based systems severity of the phenotypes strongly correlated with the intensity of reporter expression. FIG. 13a: Developmental abnormalities in transgenic $F_3$ fish carrying a genomic insertion of the non-inducible EF-GVP-UG cassette (Koster and Fraser, 2001), which included 150-bp *Xenopus* EF-1α-promoter driving Gal-4-VP16 and the EGFP ORF under control of the 14-mer of UAS Gal-4-binding sites fused to the fish basal promoter E1b. The cassette was cloned into the Tol2 transposable element (Kawakami et al., 2000) to enhance the transgenesis. Transgenic $F_1$ offspring from 8 positive founders harboring independent Tol2 insertions was produced and analyzed, all showing very strong EGFP expression and developmental abnormalities. The extent of the abnormalities correlated with the intensity of EGFP expression. In the weakest expressing line the abnormalities became visible only at 3 dpf, however none of the fish survived to adulthood. FIGS. 13b-13f: Treatment with 1 µM mifepristone in the growth water 10 hpf onwards. FIG. 13b: Control wild type fish. FIG. 13c: Transgenic $F_2$ embryos harboring the LexPR driver-reporter cassette described in this manuscript. Expression of LexA transactivator does not affect embryo development and morphology of the EGFP-positive cells. FIGS. 13d-13g: Transgenic $F_2$ fish (line SWD-G4) carrying the Gal4/UAS-based mifepristoneinducible system described by (Burcin et al., 1999). The cassette harbored a gene for chimeric transcription factor consisting of Gal4 DNA binding domain, a truncated ligand binding domain from the human progesterone receptor and an activation domain of the human NF-κB protein under control of the 0.5 krt8 promoter (identical to the promoter used in LexPR system described in this manuscript); and EGFP gene under control of 6×Gal4 upstream activating sequences fused to the minimal adenovirus E1b promoter. The cassette was packed into the Ds transposon vector to induce effective transgenesis. FIG. 13f: Typical phenotype developed in transgenic $F_2$ fish (SWD-G4 line) following the induction with 1 µM mifepristone at 10 hpf onwards. FIG. 13g: Transgenic $F_2$ fish (SWD-G4 line), which was induced early but showed weak phenotype. Transgenic fish harboring Gal4/UAS-based mifepristone-inducible system exhibited developmental phenotypes only upon induction, suggesting that inducible Gal4-based transactivator require mifepristone binding to cause side effects.

DETAILED DESCRIPTION OF THE INVENTION

Figure 1:
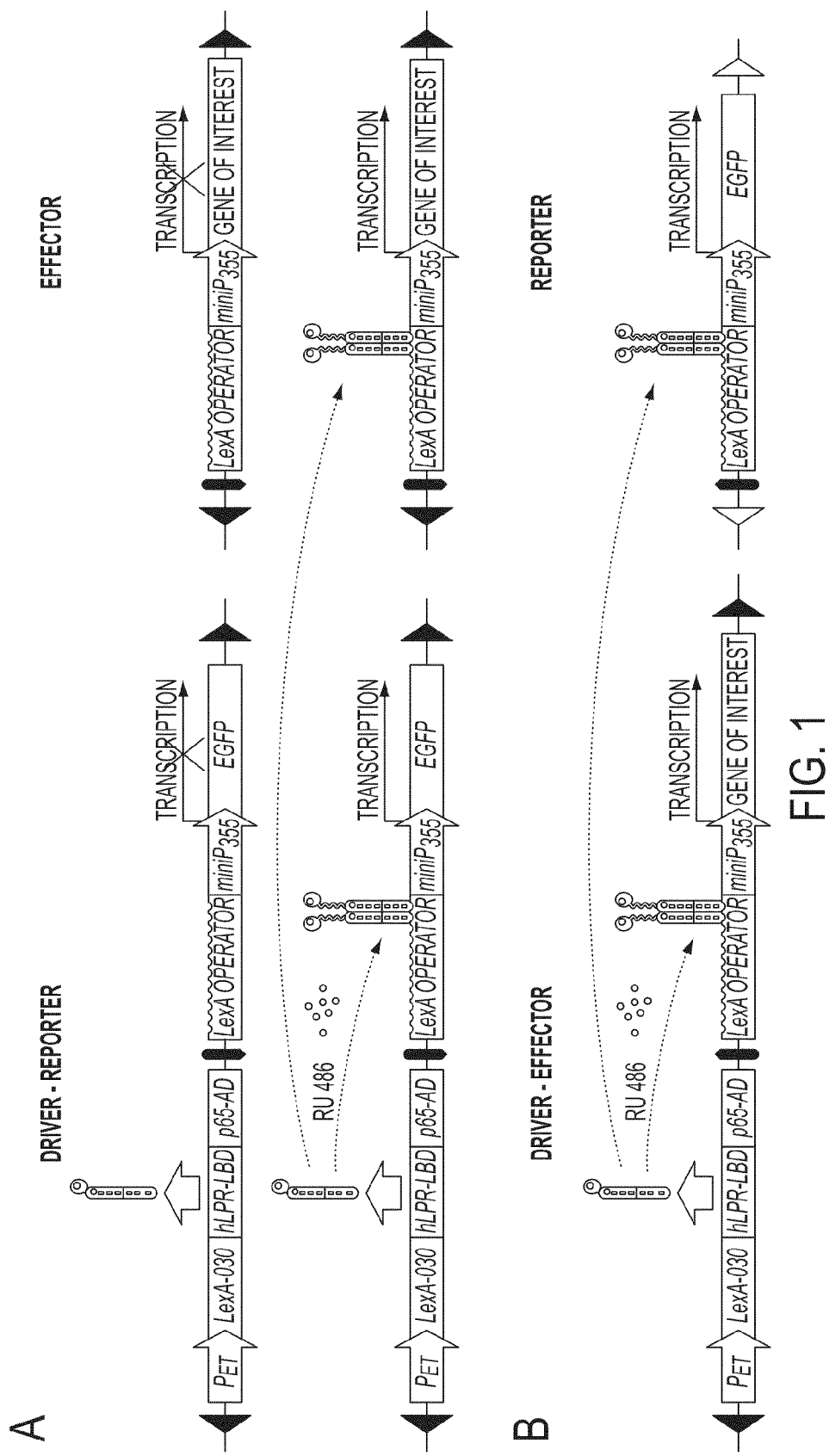
FIGS. 1A and 1B show a schematic representation of the mifepristone-inducible LexA-based gene expression system. The LexPR driver-reporter binary cassette contains two transcription units: the gene encoding a chimeric LexPR transactivator ($Lex^{DBD}$-$PR^{LBD\Delta}$-$p65^{AD}$) under the control of an enhancer-trap promoter ($P_{ET}$) and the EGFP reporter gene under the control of a minimal promoter (mini$P_{35S}$) fused to a synthetic LexA operator. The effector cassette harbors a gene of interest under the control of the minimal 35S promoter fused to the synthetic LexA operator. To activate transcription of the gene of interest the LexPR transactivator has to be produced from a separate driver cassette. The LexPR transactivator binds to the LexA operator sequence to activate the transcription of the downstream genes only in the presence of mifepristone (RU 486). The cassettes are flanked by cis-required sequences of Ds transposon (black arrowheads) to facilitate generation of transgenic lines.

The present invention relates generally to chemical-inducible system and to methods of use in transgenic animals or in animal cells. More specifically, the present invention relates to a chimeric transcription factor that binds to a ligand and functions in ligand-dependent manner to induce expression of genes of interest under the control of a synthetic operator-promoter sequence. The expression of genes of interest can be tightly controlled by adding or removing the ligand.

In the description which follows, the aspects of the invention may be described with reference to zebrafish for convenience only. It is understood that other fish and other animals can be used in place of zebrafish.

Although GAL4-based expression systems have been described in the art, we have tested GAL4-based expression systems in transgenic zebrafish and found that these systems suffer from several side effects. Specifically, we have tested a non-inducible (modified from Koster and Fraser, 2001) GAL4-based expression system and a chemical-inducible (modified from Burcin et al., 1999) GAL4-based expression system in transgenic zebrafish. We identified several side effects using these systems including developmental abnormalities, irregular expression levels and background expression. In view of these side effects, it was desired to develop an inducible system that did not suffer from such effects.

Thus, in one aspect, the present invention provides an inducible system for chemically regulated expression of genes in transgenic animals or in cells of animals, including, but not limited to fish such as zebrafish. The key element of this system is a hybrid transcription factor (transactivator) that represents a protein fusion of a DNA binding domain from the bacterial LexA protein, a ligand binding domain from the human progesterone receptor and an activation domain. In the presence of a ligand for the progesterone receptor, the transactivator activates the transcription of target genes controlled by a synthetic operator-promoter that contains LexA binding sites. The expression of the target gene can be tightly controlled by adding or removing the ligand. In one embodiment, the ligand binding domain is a truncated ligand binding domain of the human progesterone receptor. In another embodiment, the ligand is mifepristone (RU 486), a progesterone antagonist. This hybrid transcription factor (LexPR transactivator) binds to the synthetic steroid, mifepristone (RU-486), and functions in a ligand-dependent manner to induce expression of the gene(s) placed under the control of a synthetic operator-promoter sequence that harbors LexA binding sites. Transgene expression is strictly controlled and can be induced at any stage of the life cycle through administration of mifepristone. Thus, the present invention provides a controlled reversible (i.e., switch on and off) expression of target genes in a transgenic animal or in a cell of an animal.

The activation domain is selected to activate the transcription from the target promoter. Any activation domain, which permits activation of gene transcription through protein-protein interactions with the components of the RNA polymerase II transcription complex or with the other proteins involved in initiation and stimulation of transcription, can be used in the present invention. In one embodiment, the activation domain is from the human p65 protein, a component of the NF-κB, also referred to herein as the NF-κB/p65 protein. In a second embodiment, the activation domain is the transactivation domain of the HSV virion protein VP16. Other examples of activation domains that may be used include, but are not limited to, activation domains of adenovirus E1A, Epstein-Barr virus EBNA 2, yeast Gal4, mammalian Sp1, Oct1 and Oct2, and the like.

In a second aspect, the present invention provides, a transactivation construct containing the chimeric transcription factor operatively linked to a promoter or to a splice acceptor sequence. As defined herein, a nucleotide sequence is "operably linked" to another nucleotide sequence when it is placed in a functional relationship with another nucleotide sequence. For example, if a coding sequence is operably linked to a promoter sequence, this generally means that the promoter may promote transcription of the coding sequence. Operably linked means that the DNA sequences being linked are typically contiguous and, where necessary join two protein coding regions, contiguous and in reading frame. Since enhancers may function when separated from the promoter by several kilobases and intron sequences may be of variable lengths, some nucleotide sequences may be operably linked but not contiguous.

In one embodiment, the transactivation construct containing the chimeric transcription factor is operatively linked to a promoter. In one embodiment, the promoter is one which drives expression of the transactivator and is an enhancer trap promoter. In one embodiment, the enhancer trap promoter is zebrafish keratin8 promoter (Parinov et al., 2004). In another embodiment, the enhancer trap promoter is any other eukaryotic promoter that produces desirable trapping. Practically any eukaryotic promoter is capable of responding to enhancers with varying efficiency and therefore can be used as enhancer trap promoter. Examples of promoters include, but are not limited to, EF1α promoter, hsp, and the like (Balciunas et al., 2004; Scott et al., 2007). In another embodiment, the promoter is an organ specific promoter, or a tissue specific promoter or a cell specific promoter (e.g. GFAP, Flk-1, GATA-1, Rag2, and the like), ubiquitous, constitutive or developmentally regulated promoter. Thus, in accordance with the present invention any promoter can be used. The choice of promoter depends on the experimental goal and is readily selected by a skilled artisan.

In another embodiment, the transactivation construct containing the chimeric transcription factor is operatively linked to a splice acceptor sequence. This produces so called gene trap systems (Stanford et al., 2001; Skarnes et al., 1992). Splice acceptor sequences are well known to the skilled artisan, and any suitable splice acceptor sequence can be used in accordance with the present invention.

In a third aspect, the present invention provides expression constructs for use in expressing genes in transgenic animals or in cells of animals. In one embodiment, the construct comprises a synthetic operator-promoter operably linked to a gene (also sometimes referred to as a coding sequence). In one embodiment, the operator is a synthetic LexA operator operatively linked to a promoter. In one embodiment, the synthetic LexA operator is a ColE1 operator. In another embodiment, the LexA operator is a ColE1 operator that is modified or changed to a different sequence containing LexA binding sites (e.g., lexA, recA operator sequences or consensus). In one embodiment, the synthetic LexA operator contains one or more, preferably two or more LexA binding sites. In another embodiment, the number of the operator sequences or LexA binding sites can be changed to optimize the performance.

In the expression construct, the promoter may be any promoter that can be used in combination with the operator to drive controlled expression of the gene. In one embodiment, the promoter is a minimal promoter. Any minimal promoter from any source can be used in accordance with the present invention, including minimal promoters from viruses, bacteria, yeast, fungi, animals and plants. Minimal promoters are well known in the art and several are described in U.S. patent application publication numbers 2007/0009487 and 2006/0242717. Examples of minimal promoters that can be used in accordance with the present invention include, but are not limited to E1b minimal promoter, CMV minimal promoter, SV40 minimal promoter, Hsp70 minimal promoter, human alkaline phosphatases minimal promoter and the like. The minimal promoter is used to minimize the background expression in the absence of the transactivator. However, the use of alternative promoters in the expression construct is contemplated and its choice is within the skill in the art.

The gene in the expression construct may be any gene that is desired to be expressed in the transgenic animal or in a cell of an animal. In one embodiment, the gene is a marker gene or a reporter gene. As used herein, a reporter protein is any protein that can be specifically detected when expressed. Many reporter proteins are known and have been used for similar purposes in other organisms. These include enzymes, such as $\beta$-galactosidase, luciferase, and alkaline phosphatase, that can produce specific detectable products, and proteins that can be directly detected. Virtually any protein can be directly detected by using, for example, specific antibodies to the protein.

The use of reporter proteins that are directly detectable without requiring the addition of exogenous factors are preferred for detecting or assessing gene expression during zebrafish embryonic development. A transgenic zebrafish embryo, carrying a construct encoding a reporter protein and a tissue-specific expression sequences, can provide a rapid real time in vivo system for analyzing spatial and temporal expression patterns of developmentally regulated genes.

In a preferred embodiment, the reporter gene is a fluorescent protein gene (e.g., EGFP, GFP, RFP, BFP, YFP, or dsRED2) or a luciferase protein gene. In a most preferred embodiment, the marker is enhanced green fluorescent protein (EGFP) (Zhang et al., 1996). EGFP is preferred because of the high sensitivity of the reporter protein. The present invention is in no way limited to the preferred markers or reporters. Many additional reporter proteins are known and have been used for similar purposes. These include enzymes, such as $\beta$-galactosidase, luciferase, chloramphenicol acyltransferase, $\beta$-glucuronidase and alkaline phosphatase, that can produce specific detectable products, and proteins that can be directly detected. Virtually any protein can be directly detected by using, for example, specific antibodies to the protein. Any reporter which can be readily detected may be used in place of the EGFP. Additional markers (and associated antibiotics) that are suitable for either positive or negative selection of eukaryotic cells are disclosed, inter alia, in Sambrook and Russell (2001), *Molecular Cloning*, $3^{rd}$ Ed., Cold Spring Harbor Laboratory Press, Cold Spring Harbor, N.Y., and Ausubel et al. (1992), *Current Protocols in Molecular Biology*, John Wiley & Sons, including periodic updates. Any of the disclosed markers, as well as others known in the art, may be used to practice the present invention.

In another embodiment, the gene is a "gene of interest," i.e., a gene which is desired to express in a transgenic animal. Absolutely any gene can be chosen depending on experimental goals and is well within the skill in the art. For example, in cancer research, oncogenes such as Ras, Myc and the like can be selected. The "gene of interest" is not limited to the natural genes or coding sequences. It can be any nucleic acid sequence coding or noncoding which is desired to express in transgenic animal. For example, the RNA transcribed from the "gene of interest" can regulate expression of the target genes through antisense suppression, RNA interference (RNAi) or microRNAs (miRNAs) (Hannon and Rossi J, 2004; Ruvkun, 2001).

Although an expression construct can be made up of any nucleic acid sequences, for use in the disclosed transgenic animals it is preferred that the expression constructs combine expression sequences operably linked to a sequence encoding an expression product. The expression construct also preferably includes other components that aid expression, stability or integration of the construct into the genome of an animal. As used herein, components of an expression construct referred to as being operably linked or operatively linked refer to components being so connected as to allow them to function together for their intended purpose. For example, a promoter and a coding region are operably linked if the promoter can function to result in transcription of the coding region.

In one aspect, an expression construct containing the gene is prepared to include expression sequences. The expression sequences are used to mediate expression of an expression product encoded by the construct. As used herein, expression sequences include the synthetic operator-promoter described herein, upstream elements, enhancers, and response elements. It is preferred that the expression sequences used in the disclosed constructs be homologous expression sequences. As used herein, in reference to components of expression constructs used in a transgenic animal, homologous indicates that the component is native to or derived from the species or type of animal involved. Conversely, heterologous indicates that the component is neither native to nor derived from the species or type of animal involved.

As used herein, expression sequences are divided into two main classes, promoters and enhancers. A promoter is generally a sequence or sequences of DNA that function when in a relatively fixed location in regard to the transcription start site. A promoter contains core elements required for basic interaction of RNA polymerase and transcription factors, and may contain upstream elements and response elements. Enhancer generally refers to a sequence of DNA that functions at no fixed distance from the transcription start site and can be in either orientation. Enhancers function to increase transcription from nearby promoters. Enhancers also often contain response elements that mediate the regulation of transcription. Promoters can also contain response elements that mediate the regulation of transcription.

The disclosed expression constructs preferably include other sequences which improve expression from, or stability of, the construct. For example, including a polyadenylation signal on the constructs encoding a protein ensures that transcripts from the transgene is processed and transported as mRNA. The identification and use of polyadenylation signals in expression constructs is well established. It is preferred that homologous polyadenylation signals be used in the transgene constructs. However, heterologous polyadenylation signals or terminators, including polyadenylation signals and terminators from plants, can be used in making the expression constructs for use in animals.

The disclosed constructs and methods can be used with any type of animal or animal cell. In one embodiment, the transgenic animal is a non-human transgenic animal. In another embodiment, the transgenic animal is a transgenic fish. In one embodiment, the animal cells are non-human animal cells. In another embodiment, the animal cells are human cells. As used herein, fish refers to any member of the classes collectively referred to as Pisces. It is preferred that fish belonging to species and varieties of fish of commercial or scientific interest be used. Such fish include, but are not limited to, salmon, trout, tuna, halibut, catfish, zebrafish, medaka, carp, tilapia, goldfish, and loach. Furthermore, most elements of these constructs have been previously applied in very distant hosts: bacterial LexA DNA binding domain and operator were utilized in plants, invertebrates and in vertebrate cell cultures (Nettelbeck et al., 1998; Szuts and Bienz, 2000; Zuo et al., 2000); the hormone binding domain of human progesterone receptor (hPR-LBD) was explored in yeast (Vegeto et al., 1992); NF-κB/p65 activation domain was shown to activate transcription in yeast (Moore et al. 1993); maize Ac/Ds transposable elements performed well in plants, fungi and animal kingdoms (Emelyanov et al., 2006); 35S CaMV plant virus minimal promoter and *Agrobacterium* Nos terminator were used in plants (Zuo et al., 2000); EGFP, mCherry and ECFP performed well in all tested organisms; zebrafish krt8 promoter was active in human and mouse cell cultures. These results implicate the use of these systems and constructs in a wider range of hosts (from amphibians to mammals, and possibly in invertebrates, fungi and plants).

The most preferred fish for use with the disclosed constructs and methods is zebrafish, *Danio rerio*. Zebrafish are an increasingly popular experimental animal since they have many of the advantages of popular invertebrate experimental organisms, and include the additional advantage that they are vertebrates. Another significant advantage of zebrafish is that, like *Caenorhabditis*, they are largely transparent (Kimmel, 1989). General zebrafish care and maintenance are described by Streisinger (1984) and Westerfield (2000).

Zebrafish embryos are easily accessible and nearly transparent. Given these characteristics, a transgenic zebrafish embryo, carrying a construct encoding a reporter protein and tissue-specific expression sequences, can provide a rapid real time in vivo system for analyzing spatial and temporal expression patterns of developmentally regulated genes. In addition, embryonic development of the zebrafish is extremely rapid. In 24 hours an embryo develops rudiments of all the major organs, including a functional heart and circulating blood cells (Kimmel, 1989). Other fish with some or all of the same desirable characteristics are also preferred.

In addition to fish, the disclosed constructs and methods can be used with other animals such as mice, rats, pigs, goats, livestock, birds, amphibians and insects. Techniques for preparing transgenic animals are well known in the art as illustrated herein.

Figure 2:
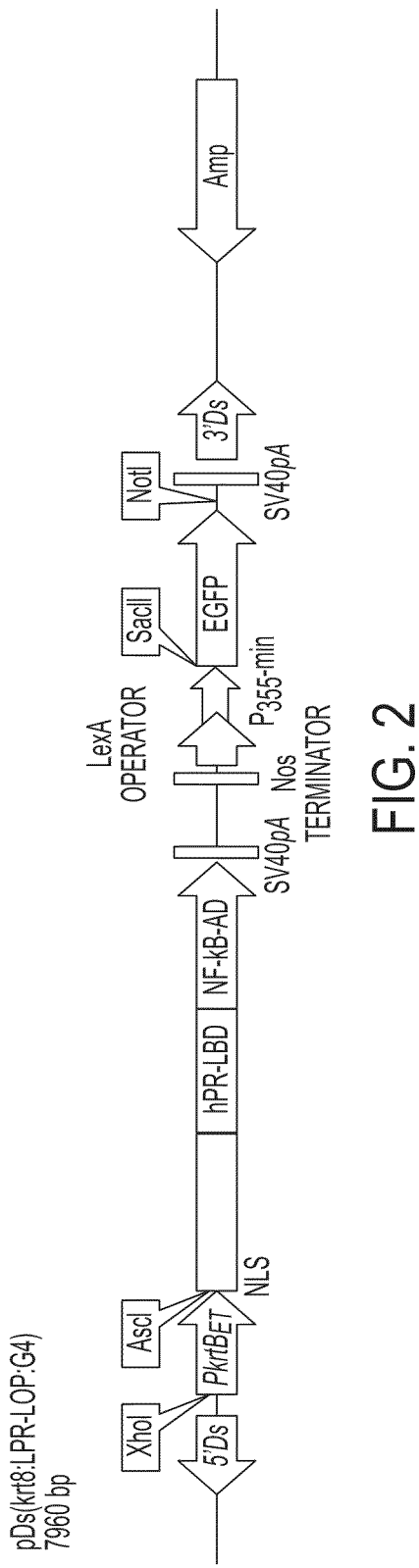
FIG. 2 shows a LexA-based mifepristone-inducible gene expression system (LexPR-driver and reporter construct). The DNA construct carries an open reading frame for an artificial transcription factor representing the fusion of a DNA binding domain from the bacterial LexA protein, a truncated ligand binding domain from the human progesterone receptor and an activation domain from the human NF-κB/p65 protein under short zebrafish keratin8 promoter; SV40 early polyadenilation sequences; nopaline synthase terminator; synthetic LexA operator and EGFP under minimal Cauliflower Mosaic Virus 35S promoter, cloned in pBluescript SK(+) vector containing terminal cis-required elements of the Ds transposon from maize (Emelyanov et al., 2006). The keratin8 promoter and the EGFP coding sequence are flanked by unique restriction sites to allow single-step replacement with a promoter of choice and a gene of interest respectively.
Figure 3:
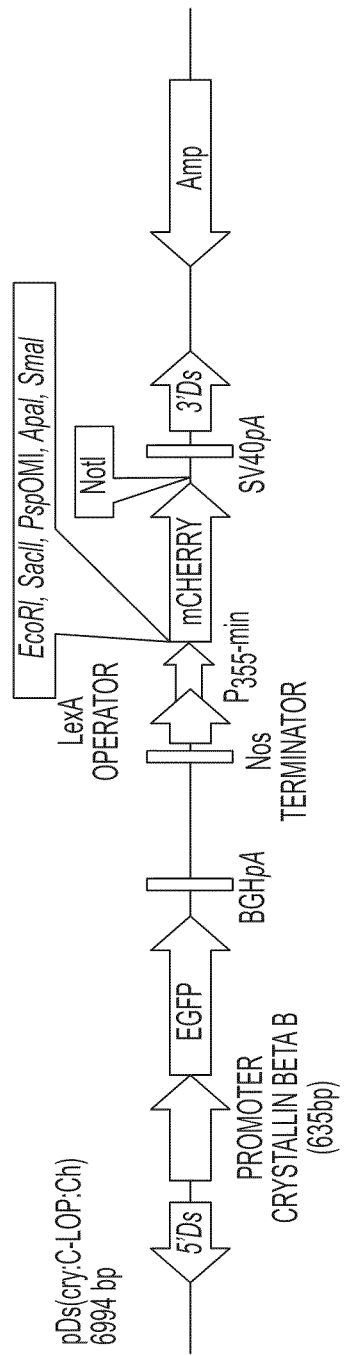
FIG. 3 shows a LexA-Effector construct (target construct). A DNA construct carries the ECFP gene under the control of the zebrafish Crystallin beta B promoter followed by the BGH polyadenilation sequence, nopaline synthase terminator, synthetic LexA operator and mCherry ORF under minimal Cauliflower Mosaic Virus 35S promoter, SV40 early polyadenilation sequence, cloned into pBluescript SK(+) vector containing terminal cis-required sequences of the Ds transposon from maize (Emelyanov et al., 2006). ECFP is a noninducible selection marker for transgenesis ("blue eyes"). The expression of mCherry is not induced by mifepristone in transgenic lines carrying this construct alone but can be induced in double lines carrying the additional driver construct. The mCherry coding sequence can be replaced with a sequence of interest using flanking unique restriction sites.
Figure 4:
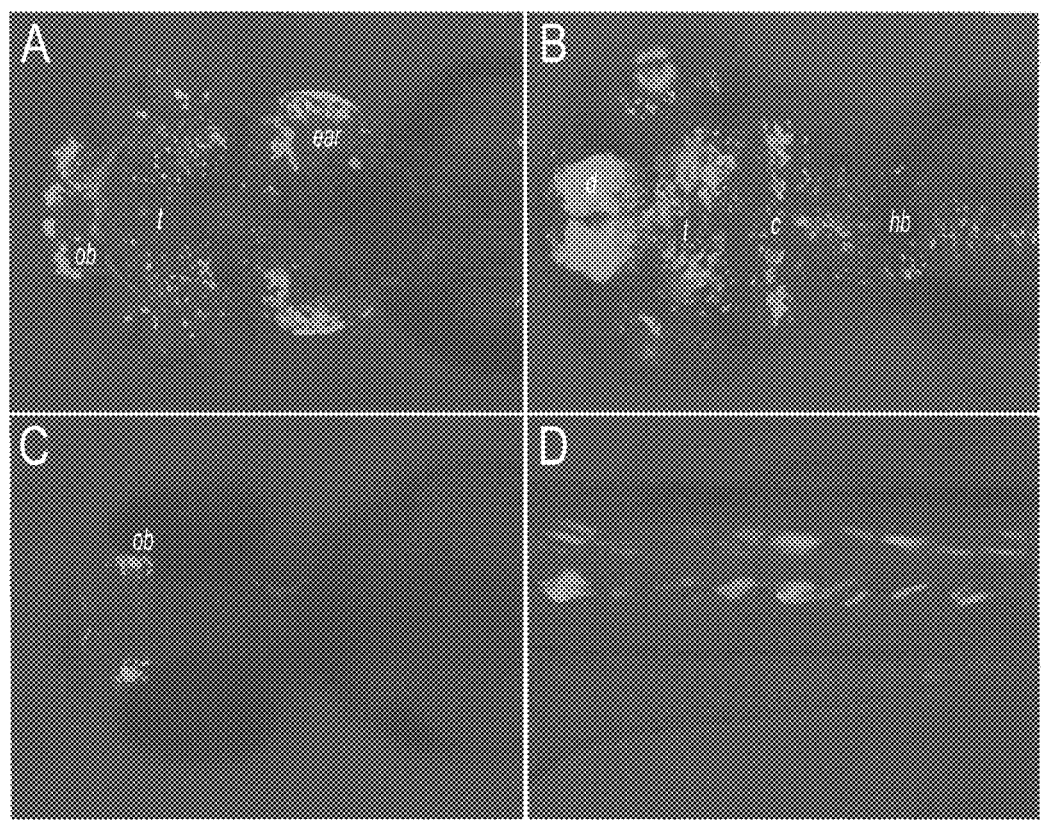
FIGS. 4A-4D show EGFP expression patterns in four independent LexPR driver-reporter lines showing different enhancer trap events. Expression of EGFP reporter was induced in transgenic $F_2$ embryos by adding mifepristone to the egg water at 1 µM final concentration at 24 hours post fertilization onwards. Images were captured at 96 hours post fertilization. No EGFP fluorescence was detected in the control populations of fish that were not treated with mifepristone (not shown).

As described in more detail herein, the present invention is directed to a system for chemically regulated transcription. In one embodiment, this system consists of two basic elements: a chimeric transcription factor and a cis-acting operator-promoter sequence containing binding sites for this transcription factor (FIGS. 1A and 1B). The transcription factor (LexPR transactivator) is a fusion of the DNA binding domain of the bacterial LexA protein (residues 1-87) (Horii et al., 1981; Mild et al., 1981), the truncated ligand binding domain of the human progesterone receptor (residues 640-914) and the activation domain of the human p65 (residues 283-551) (Burcin et al., 1999) (Lex$^{DBD}$-PR$^{LBD\Delta}$-p65$^{AD}$; FIG. 2 and the Examples herein). The operator-promoter sequence (LexOP) consists of a synthetic LexA operator (containing four ColE1 operator sequences (Ebina et al., 1983)) fused to a minimal 35S promoter from Cauliflower Mosaic Virus (Zuo et al., 2000) (FIGS. 1A, 1B, 2 and 3). The LexPR transactivator binds to the operator and induces the transcription of the gene of interest placed under control of LexOP only upon binding of the progesterone antagonist, mifepristone (commonly known as RU-486), to the progesterone receptor LBD. The actual sequence of events leading to transcription activation is unclear.

Two strategies for using this system are outlined on FIGS. 1A and 1B. The most versatile scheme involves generation of two separate transgenic lines: a driver line expressing the LexPR transactivator and an "effector" or "target" line carrying a gene of interest under the control of the LexOP (FIG. 1A). Crossing a driver with an effector line generates double transgenic offspring capable of expressing the gene of interest in specific tissues upon stimulation by mifepristone. This strategy allows combinational experiments: the same driver line can be used to express various genes into the same cells and conversely, the same effector line can be crossed to various drivers to express gene of interest in different cell or tissue types. Furthermore, large number of driver lines with various expression patterns can be easily generated using enhancer- or gene-trap strategies (Parinov et al., 2004; Scott et al., 2007). The effector cassette (LexOP:gene of interest) can also be placed together with the LexPR transactivator gene into the same vector construct (FIG. 1B). This allows straightforward generation of F$_1$ transgenic fish capable of inducible expression of a gene of interest in just one generation. This strategy is particularly appropriate when working with a single gene of interest and a suitable promoter. It is also easier to manipulate and maintain the fish carrying the transgene in a single locus.

As described in further detail herein, in order to test the LexPR expression system, a "driver-reporter" construct pDs (krt8:LPR-LOP:G4) was generated. This construct contained two components: the LexPR transactivator coding sequence under the 0.5-kb keratin8 promoter and an EGFP reporter gene under the control of the LexOP sequence (FIG. 1A, Example 2). The 0.5-kb keratin8 promoter drives expression in skin epithelia but it frequently generates various enhancer-trap expression patterns depending on the surrounding genomic environment (Parinov et al., 2004). This allows screening for enhancer-trap driver lines expressing LexPR transactivator in different cells and tissues. The pDs(krt8:LPR-LOP:G4) also contains the Ds cis-required sequences to facilitate generation of transgenic lines and random insertion screenings (Emelyanov et al., 2006).

Thus, in accordance with the present invention, a system for expressing genes in transgenic animals or in cells of animals is provided. In one embodiment, the system comprises a LexA driver construct and an effector (also referred to herein as target) construct. The LexA driver construct comprises the transactivation construct. In another embodiment, the LexA driver construct also includes a reporter and this construct is also referred to herein as a LexA driver-reporter construct. The LexA driver-reporter construct comprises the transactivation construct and expression construct in which the gene is a marker gene or a reporter gene. In one embodiment, the effector construct comprises the expression construct in which the gene is a gene of interest. In one embodiment, the LexA driver construct and the effector construct are in separate nucleic acid molecules. In another embodiment, the LexA driver construct and the effector construct are in the same nucleic acid molecule.

In a further aspect, the present invention provides a method of expressing genes in transgenic animals or in cells of animals. In one embodiment, the method comprises preparing transgenic animals that contain the LexA driver construct and the effector construct. In one embodiment, a first transgenic animal is prepared to contain the LexA driver construct and a second transgenic animal is prepared to contain the effector construct. Crossing the first and second transgenic animals or their progeny create a third transgenic animal containing both the LexA driver construct and the effector construct. In another embodiment, a transgenic animal is prepared that contains the LexA driver construct and the effector construct using a nucleic acid molecule that contains both constructs. In another embodiment, the method comprises preparing cells of animals that contain the LexA driver construct and the effector construct. In accordance with this aspect of the invention, the expression of the gene in the transgenic animal or animal cell is controlled by the addition of a ligand for the human progesterone receptor. Expression of the gene can be switched on and off by adding or removing the ligand. In a preferred embodiment, the ligand is mifepristone.

Transgenic fish are prepared using the constructs described herein. In one embodiment, a method includes introducing the nucleic acid, i.e., construct or vector described herein, into a fertilized fish egg (i.e., including a fish embryo) or an unfertilized fish egg nucleic acid. When a fertilized fish egg is used, the method includes developing the fish embryo into a transgenic fish. When the nucleic acid is introduced into a non-fertilized egg, the method includes fertilizing the egg and developing the fish embryo into a transgenic fish. The nucleic acid may be introduced into the egg by a variety of methods known to the art, including mechanical methods, chemical methods, lipophilic methods, retroviral infection methods, and electroporation. Exemplary mechanical methods include, for example, microinjection. Exemplary chemical methods include, for example, use of calcium phosphate or DEAE-Dextran. Exemplary lipophilic methods include use of liposomes and other cationic agents for lipid-mediated transfection. Such methods are generally well known to the art and many of such methods are described in, for example, *Gene Transfer Methods: Introducing DNA into Living Cells and Organisms*, (P. A. Norton and L. F. Steel, eds., Biotechniques Press, 2000); and *Current Protocols in Molecular Biology* (Ausubel et al., eds., John Wiley & Sons). Microinjection techniques involving fish are further more fully described in, for example, Chen and Powers (1990) and Fletcher and Davis (1991). Electroporation techniques involving fish are further more fully described in, for example, Powers et al. (1992) and Lu et al. (1992). Techniques for introducing DNA into fish eggs or embryos by infection with retroviral vectors, such as pantropic retroviral vectors, are further described in, for example, Burns et al. (1993).

The vector or other nucleic acid comprising the transgene may be introduced into an unfertilized egg or a fertilized egg at a desired stage of development. Multiple vectors, each encoding different transgenes as described herein may be used. When using a fertilized egg, or embryo, it is preferred to introduce the nucleic acid into the embryo (i.e., at the one-cell stage of development). However, the nucleic acid may also be administered at later stages of development, including the two-cell stage, four-cell stage, etc. Therefore, the nucleic acid may be introduced into the morula, blastula, etc. At least one isolated nucleic acid molecule incorporating the above-described transgenic construct is introduced into the zygote. Additionally, when the nucleic acid is introduced into an egg at later stages of development, at least one isolated nucleic acid molecule incorporating the above-described transgenic construct is introduced into at least one cell of the, for example, morula, blastula, etc.

Fish eggs may be obtained from the appropriate fish by standard methods. Many of the fish may be purchased commercially from, for example, pet stores. Fertilized eggs may be obtained by methods known to the art. For example, a desired number of appropriately aged fish, such as about three to about twelve month old fish, with a desired ratio of females to males (such as about 2:1) may be placed in an appropriately sized container, such as a tank. Eggs may be collected by, for example, placing the fish in a nuptial chamber in the tank for an appropriate time after mating, such as about 10 to 60 minutes. Such methods are described in, for example, Culp et al. (1991). Alternatively, fish eggs may be artificially fertilized by methods known to the skilled artisan. One skilled in the art is familiar with other methods of obtaining such fertilized fish eggs.

After introducing the nucleic acid construct into the fish egg or embryo, the fish egg or embryo is provided with an environment conducive to development into an adult fish. Such an environment may include, for example, growth at 28.5° C. in E3 egg water for 15 days followed by introduction into circulating system water by day 16 (Westerfield, 2000).

Fish harboring a transgene can be identified by any suitable means. The use of reporter proteins that, like fluorescent proteins (such as EGFP, GFP, RFP, BFP, YFP, or dsRED2), are directly detectable without requiring the addition of exogenous factors are preferred for detecting or assessing gene expression during zebrafish embryonic development. A transgenic zebrafish embryo, carrying a construct encoding a reporter protein can provide a rapid real time in vivo system for analyzing spatial and temporal expression patterns of developmentally regulated genes. Alternatively, the genome of potential transgenic fish can be probed for the presence of construct sequences. To identify transgenic fish actually expressing the transgene, the presence of an expression product can be assayed. Several techniques for such identification are known and used for transgenic animals and most can be applied to transgenic fish. Probing of potential or actual transgenic fish for nucleic acid sequences present in or characteristic of a transgene construct is preferably accomplished by Southern or Northern blotting. Also preferred is detection using polymerase chain reaction (PCR) or other sequence-specific nucleic acid amplification techniques.

The transgene may be included in a vector for delivery. A vector, as used herein and as known in the art, refers to a nucleic acid construct that includes genetic material designed to direct transformation (i.e., the process whereby genetic material of an individual cell is altered by incorporation of exogenous DNA into its genome) of a targeted cell. A vector may contain multiple genetic elements positionally and sequentially oriented, i.e., operably linked with other necessary or desired elements such that the nucleic acid in a cassette can be transcribed and, if desired, translated in the microinjected, single-cell fertilized embryo.

Recombinant expression vectors may be constructed by incorporating the above-recited nucleotide sequences within a vector according to methods well known to the skilled artisan and as described, for example, in references cited herein. A wide variety of vectors are known that have use in the invention. Suitable vectors include plasmid vectors, viral vectors, including retrovirus vectors (e.g., see Miller et al., 1993), adenovirus vectors (e.g., see Erzurum et al., 1993; Zabner et al., 1994; Davidson et al., 1993) adeno-associated virus vectors (e.g., see Flotte et al., 1993), herpesvirus vectors (e.g., see Anderson et al., 1993), and lentivirus vectors (e.g., see Lever, 2000).

Identifying the pattern of expression in the disclosed transgenic fish can be accomplished by measuring or identifying expression of the transgene in different tissues (tissue-specific expression), at different times during development (developmentally regulated expression or developmental stage-specific expression), in different cell lineages (cell lineage-specific expression). These assessments can also be combined by, for example, measuring expression (and observing changes, if any) in a cell lineage during development. The nature of the expression product to be detected can have an effect on the suitability of some of these analyses. On one level, different tissues of a fish can be dissected and expression can be assayed in the separate tissue samples. Such an assessment can be performed when using almost any expression product. This technique is commonly used in transgenic animals and is useful for assessing tissue-specific expression. Expression can be determined biochemically, enzymatically, phenotypically or in a model fish.

Although the preparation of transgenic animals has been illustrated by transgenic zebrafish, techniques are well known in the art for preparing transgenic animals of other species. These include, but are not limited to, animals (U.S. Pat. Nos. 7,138,562 and 6,872,868), mice (U.S. Pat. Nos. 7,220,892 and 7,041,869 and U.S. patent application publication No. 2007/0118915), rats (U.S. Pat. No. 6,576,811 and U.S. patent application publication No. 2007/0044162), pigs (U.S. Pat. Nos. 7,115,796 and 6,639,122 and U.S. patent application publication No. 2005/0268347), livestock (U.S. Pat. No. 7,199,281), birds (U.S. patent application publication Nos. 2007/0113299 and 2004/0172666), amphibian (U.S. patent application publication No. 2007/0107072), (*drosophila* (U.S. Pat. No. 6,943,278) and flies (U.S. patent application publication No. 2005/0132423). A general methods for preparing transgenic animals is also disclosed in U.S. patent application publication No. 2006/0031952.

To illustrate the present invention, we have generated constructs carrying driver and effector cassettes. Both constructs contain the Ds cis-required sequences to facilitate generation of transgenic lines carrying these functional cassettes in their genome. The use of the Ds cis-required sequences has been described in Emelyanov et al., 2006 and in PCT published application No. WO 2006/124001. The driver ("driver-reporter") cassette consists of two components: the gene for a transactivator under a short keratin8 promoter and an EGFP reporter gene under control of a minimal promoter fused with synthetic LexA operator (FIGS. 1A-1B and 3A-3C). The short keratin8 promoter is an efficient enhancer trap promoter that can produce various tissue-specific expression patterns depending on the genomic environment (Parinov et al., 2004). The EGFP reporter is expressed only in the cells that express transactivator and conveniently marks these cells. The reporter expression can be used to screen for driver lines with distinct transactivator expression patterns created due to enhancer trap effect on the keratin8 promoter. The effector construct DNA construct harbors an ORF for red fluorescent protein mCherry under a minimal Cauliflower Mosaic Virus 35S promoter fused to a LexA operator. It also harbors ECFP under the control of the zebrafish Crystallin beta B promoter used as an additional marker to select transgenic lines (Example 3).

We have experimentally demonstrated several important capabilities of this system. Using this system gene expression can be switched on and off by adding and removing the ligand, e.g., adding or removing mifepristone in the growth water for transgenic zebrafish. The system allows stringent control of expression: no reporter gene expression was detected without treatment with the ligand, e.g., mifepristone. Inducible expression of the chimeric transactivator causes no side effects in transgenic animals, e.g., zebrafish, even when the ligand, e.g., mifepristone, is added at early developmental stages. Only small amounts of the ligand, e.g., mifepristone, is required for induction. This system allows generating driver lines capable of transactivating the expression of the effector/target carrying a gene of interest.

Modifications can be made to the system in accordance with the present invention. For example, transgenic animals with various patterns of expression of the chimeric transcription factor ("driver" lines) can be generated using various promoters, and promoter-, gene- and enhancer-trap strategies, and the like (Parinov et al., 2004; Stanford et al., 2001). For example, in case of gene-trap strategy a splice acceptor sequence instead of a promoter is used to drive the transcription of the hybrid transcription factor (Stanford et al., 2001). In addition, the sequence of the hybrid transcription factor can be further modified in order to improve the efficiency or for special purposes. For example: activation domain from the human NF-κB can be replaces with alternative domains (e.g. the transactivation domain of the HSV virion protein VP16). Also, the CaMV 35S basic promoter that is used in the Examples can be modified or changed to a different promoter. Furthermore, the sequence of ColE1 operator that we used can be modified or changed to a different sequence containing LexA binding sites (e.g. lexA, recA operator sequences or consensus). The number of the operator sequences or LexA binding sites can also be changed in order to optimize the performance. Finally, different promoters can be used instead of keratin8 promoter to drive tissue expression of transactivator and for enhancer trapping.

As described herein, the present invention provides a genetic system that can be used to control transgene expression by switching it on or off when required, i.e., the present invention provides a controlled reversible expression of genes. Moreover, the present invention provides a genetic system that can be used to drive the expression only in the desired tissues or cells. Thus, the present invention can be used to produce transgenic animals with tightly controlled and inducible expression of genes which can be tissue- or cell-specific. Also, the present invention can be used to induce the expression of genes in transgenic animals or in specific tissues or cells of transgenic animals or cells of animals. In addition, the present invention can be used to generate transgenic driver lines for inducible expression of genes, including tissue- or cell-specific expression, in transgenic animals. The transgenic animals prepared in accordance with the present invention have the constructs described herein stably incorporated into their genome.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Hogan et al., *Manipulating the Mouse Embryo*, (Cold Spring Harbor Laboratory Press, Cold Spring Harbor, N.Y., 1986); Westerfield, M., *The zebrafish book. A guide for the laboratory use of zebrafish* (*Danio rerio*), (4th Ed., Univ. of Oregon Press, Eugene, 2000).

EXAMPLES

The present invention is described by reference to the following Examples, which are offered by way of illustration and are not intended to limit the invention in any manner. Standard techniques well known in the art or the techniques specifically described below were utilized.

Example 1

Materials and Methods

Fish: Zebrafish were maintained according to established protocols (Westerfield, 1995).

Generating transgenic fish using Ac/Ds transposon system: Transgenic fish carrying insertions of the driver and effector constructs containing Ds cis-required sequences (as described herein) were generated as previously described (Emelyanov et al., 2006). 5-10 pg of plasmid DNA was co-injected into zebrafish embryos (yolk center) with 25-50 pg of in vitro synthesized transposase mRNA at the 1-2-cell stage. The injected fish were raised and out-crossed to the wild type, and the resulting embryos were screened for the mifepristone-induced EGFP expression (driver-reporter lines) or for stable ECFP expression in the lens (effector lines). For screening of the driver lines, mifepristone was added to the growth water at 1 µM final concentration at 24 hpf, and GFP expressing $F_1$ embryos were selected and raised. Only the lines that segregated as a single locus (produced 1:1 ratio when outcrossed to nontransgenic fish) were selected. Similarly, the effector lines which showed 1:1 segregation of cry:ECFP marker (cyan expression in the lens) were selected. We did not ascertain copy number but only used the lines that segregated as a single locus. These lines may contain several closely linked copies of the constructs, however, it does not complicate line maintenance or expression analysis.

RT-PCR: RNA was isolated with RNAEasy Kit (Quiagen). cDNA was synthesized from 0.5 µg DNA free RNA with 0.5 µg/µl random hexanucleotide and 20u SuperScript™ Reverse Transcriptase (Invitrogen) in 20 µl. cDNA mix was inactivated at 70° C. for 15 min and diluted 5 times with water. 2 µl of the mix was used for PCR with specific primers: for LoxPR transactivator aaatcattgccaggttttcg (SEQ ID NO:42) and agccttccaaaggaattgt (SEQ ID NO:43); for EGFP reporter acgtaaacggccacaagttc (SEQ ID NO:44) and gtcctccttgaagtcgatgc (SEQ ID NO:45). PCR was performed with Taq polymerase (Quiagen) in 20 µl. The PCR cycling conditions: 35 cycles (94° C. for 30 sec; 55° C. for 10 sec; 72° C. for 10 sec).

RNA in situ hybridization: Whole mount in situ hybridization using antisense RNA probes for full length LexPR transactivator and EGFP labeled with digoxigenin (Roche, USA) was carried out as previously described (Oxtoby and Jowett, 1993). After in situ hybridization stained embryos were mounted in PBS-glycerol and viewed using Nikon SMZ1600 stereomicroscope. Images were taken with Nikon DXM1200F digital camera with the Nikon ACT-1 software and processed using Adobe Photoshop 7.0.1 software.

Example 2

LexA-Based Mifepristone-Inducible Gene Expression System (LexPR-Driver and Reporter Construct)

A DNA construct (FIG. 2) carrying an open reading frame for an artificial transcription factor representing the fusion of a DNA binding domain from the bacterial LexA protein, a truncated ligand binding domain from the human progesterone receptor and an activation domain from the human NF-κB/p65 protein under short zebrafish keratin8 promoter; SV40 early polyadenilation sequences; nopaline synthase terminator; synthetic LexA operator and EGFP under minimal Cauliflower Mosaic Virus 35S promoter, was prepared by combining the elements by sequential cloning of PCR fragments in pBluescript SK(+) vector containing terminal cis-required elements of the Ds transposon from maize (Emelyanov et al., 2006). The keratin8 promoter and the EGFP coding sequence are flanked by unique restriction sites to allow single-step replacement with a promoter of choice and a gene of interest respectively. The sequence details are shown in Table 1. The primer sequences are shown in Table 2. The pDs(krt8:Lpr-LOP:G4) full sequence is set forth in SEQ ID NO:46.

TABLE 1

Components of LexA-Driver and Reporter Construct

| Nucleotides | Source | SEQ ID NO: |
|---|---|---|
| 1-662 | pBluescript SK(+) vector DNA (X52325.1 GI: 58067). | 1 |
| 663-898 | Ds 5'-end cis-required sequence. | 2 |
| 899-922 | Synthetic polylinker sequence. | 3 |
| 923-1487 | PCR fragment *Danio rerio* Keratin 8 promoter region with partial 5' UTR. Derived from zebrafish genomic DNA. PCR-amplified fragment cloned using Xho/Pme and primers Krt8ETF1Xho and KRT8ET-RPme. | 4 |
| 1488-1507 | Synthetic filler DNA sequence. | 5 |
| 1508-1804 | 1-87 aa LexA repressor DNA binding domain sequence containing SV40 nuclear localization sequence (SEQ ID NO: 7). The sequence is amplified using pER10 plasmid as template and the primers nlsLBDFAsc and LexDBDRKpn, and cloned using AscI/KpnI. | 6 |
| 1805-1828 | Synthetic filler DNA sequence. | 8 |
| 1829-3469 | PCR fragment containing truncated human progesterone receptor binding domain fused with activation domain of p65 subunit of human NF-kB derived from pSwitch plasmid (Invitrogen) using primers PRLBDFKpn and PRADRNot. | 9 |
| 3470-3716 | plasmid fragment containing SV40 early polyadenylation signal (SEQ ID NO: 11) derived from pEGFPN1 (Clontech). | 10 |
| 3717-3746 | Synthetic filler DNA sequence. | 12 |
| 3747-4364 | PCR fragment that includes nopaline synthase terminator from *Agrobacterium tumefaciens* (NOS terminator; SEQ ID NO: 14), synthetic Lex A operator (SEQ ID NO: 15) derived from ColE1 operator (Ebina et al., 1983)) containing LexA binding sites, and Cauliflower Mosaic Virus 35S minimal promoter (SEQ ID NO: 16) derived from pER10. The sequence is amplified from pER10 plasmid using the primers LexOPFSwa and LexOPREco, and cloned using SwaI/EcoRI. | 13 |
| 4365-5376 | Plasmid fragment containig EGFP coding sequence (SEQ ID NO: 18) and SV40 early polyadenylation signal (SEQ ID NO: 11) derived from pEGFPN1 (Clontech). | 17 |
| 5377-5750 | Ds 3'-end cis-required sequence | 19 |
| 5751-7960 | pBluescript SK(+) vector DNA (X52325.1 GI: 58067) | 20 |

TABLE 2

Primers

| Primer Name | Forward (F) or Reverse (R) | SEQ ID NO: |
|---|---|---|
| Krt8ETF1Xho | F | 21 |
| Krt8ET-RPme | R | 22 |
| nlsLBDFAsc | F | 23 |
| LexDBDRKpn | R | 24 |
| PRLBDFKpn | F | 25 |
| PRADRNot | R | 26 |
| LexOPFSwa | F | 27 |
| LexOPREco | R | 28 |
| CbBFA | F | 29 |
| CbBR | R | 30 |

Example 3

LexA-Effector Construct (Target Construct)

A DNA construct (FIG. 3) carrying the ECFP gene under the control of the zebrafish Crystallin beta B promoter followed by the BGH polyadenilation sequence, nopaline synthase terminator, synthetic LexA operator and mCherry ORF under minimal Cauliflower Mosaic Virus 35S promoter, SV40 early polyadenilation sequence, was prepared by cloning into pBluescript SK(+) vector containing terminal cis-required sequences of the Ds transposon from maize (Emelyanov et al., 2006). ECFP is a noninducible selection marker for transgenesis ("blue eyes"). The expression of mCherry is not induced by mifepristone in transgenic lines carrying this construct alone but can be induced in double lines carrying the additional driver construct. The mCherry coding sequence can be replaced with a sequence of interest using flanking unique restriction sites. The sequence details are shown in Table 3. The primer sequences are shown in Table 2. The pDs(cry:C-LOP:Ch) full length sequence is set forth in SEQ ID NO:47.

TABLE 3

Components of LexA-Effector Construct

| Nucleotides | Source | SEQ ID NO: |
|---|---|---|
| 1-662 | pBluescript SK(+) vector DNA (X52325.1 GI: 58067) | 1 |
| 663-898 | Ds 5'-end cis-required sequence | 2 |
| 899-916 | Synthetic filler DNA sequence. | 31 |
| 917-1551 | Zebrafish Crystallin beta B promoter. PCR-amplified fragment cloned using Xho/Pme and primers CbBFA and CbBR. | 32 |

TABLE 3-continued

Components of LexA-Effector Construct

| Nucleotides | Source | SEQ ID NO: |
|---|---|---|
| 1552-1605 | Synthetic sequence containing Lox2272 site for Cre recombinase. | 33 |
| 1606-1748 | Fragment containing synthetic intron IVS8 derived from pGene/V5-HisA (Invitrogen). | 34 |
| 1749-2475 | Fragment containig ECFP sequence derived from pECFP1 (Clontech). | 35 |
| 2476-2490 | Synthetic filler DNA sequence. | 36 |
| 2491-2756 | Fragment containing BGH (bovine growth hormone) polyadenylation sequence derived from pGene/V5-HisA (Invitrogen). | 37 |
| 2757-2795 | Synthetic filler DNA sequence. | 38 |
| 2796-3413 | PCR fragment containing nopaline synthase terminator from *Agrobacterium tumefaciens* (NOS terminator; SEQ ID NO: 14), synthetic Lex operator (4 LexA binding sites) (SEQ ID NO: 15), and Cauliflower Mosaic Virus 35S minimal promoter (SEQ ID NO: 16) derived from pER10. The sequence is amplified from pER10 plasmid using the primers LexOPFSwa and LexOPREco, and cloned using SwaI/EcoRI. | 13 |
| 3414-3444 | Synthetic filler DNA sequence. | 39 |
| 3445-4177 | Fragment containing mCherry fluorescence protein sequence derived from pCS2 + mCherry (gift from Dr. S. Jesuthasan). | 40 |
| 4178-4410 | Plasmid fragment containing SV40 early polyadenylation signal derived from pEGFPN1 (Clontech). | 41 |
| 4411-4784 | Ds 3'-end cis-required sequence | 19 |
| 4785-6994 | pBluescript SK(+) vector DNA (X52325.1 GI: 58067) | 20 |

Example 4

Generating Transgenic Fish

Transgenic fish carrying insertions of the driver and effector constructs (described in Examples 2 and 3) were generated as previously described (Emelyanov et al., 2006; WO 2006/124001). Basically, 5-10 pg of plasmid DNA with 25-50 pg of in vitro synthesized transposase mRNA was co-injected into zebrafish embryos (yolk center) at the 1-2-cell stage. The injected fish were raised and out-crossed to wild type. F or screening purposes mifepristone was added to the growth water at 1 μM final concentration at 24 hpf and GFP fluorescent $F_1$ embryos were selected and raised.

Example 5

Figure 5:
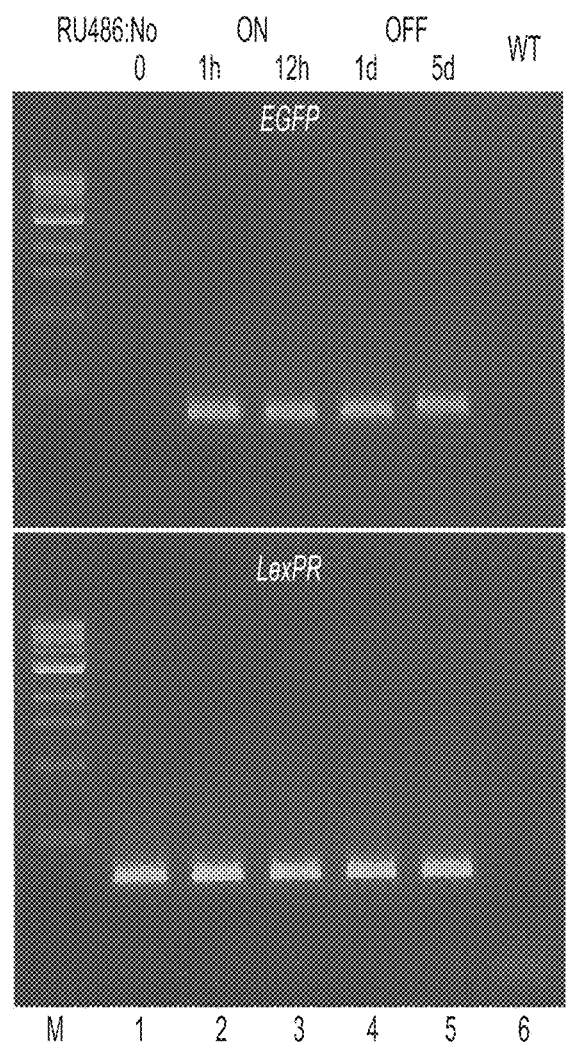
FIG. 5 shows the testing of the LexPR transcription control using RT-PCR. RT-PCR was performed on RNA extracted from transgenic F2 embryos carrying the driver-reporter construct using two pairs of primers to detect EGFP (top panel) and LexPR transactivator (bottom panel) RNA products. Embryos (36 hpf) were treated with 1 µM mifepristone for 12 hours (48 hpf). After that, the embryos were rinsed and transferred into larger tanks without mifepristone. Six mRNA samples were prepared and tested: 1) before induction (36 hpf); 2) after 1-hour induction; 3) after 12-hours induction; 4) 1 day after mifepristone withdrawal; 5) 5 days after mifepristone withdrawal; 6 wild type—negative control. The PCR-conditions (number of cycles) were optimized for detection of low quantities of RNA target, not for quantitative comparison between samples. Thus, there is in no visible product downregulation at the lane 5 (5 days post withdrawal).
Figure 6:
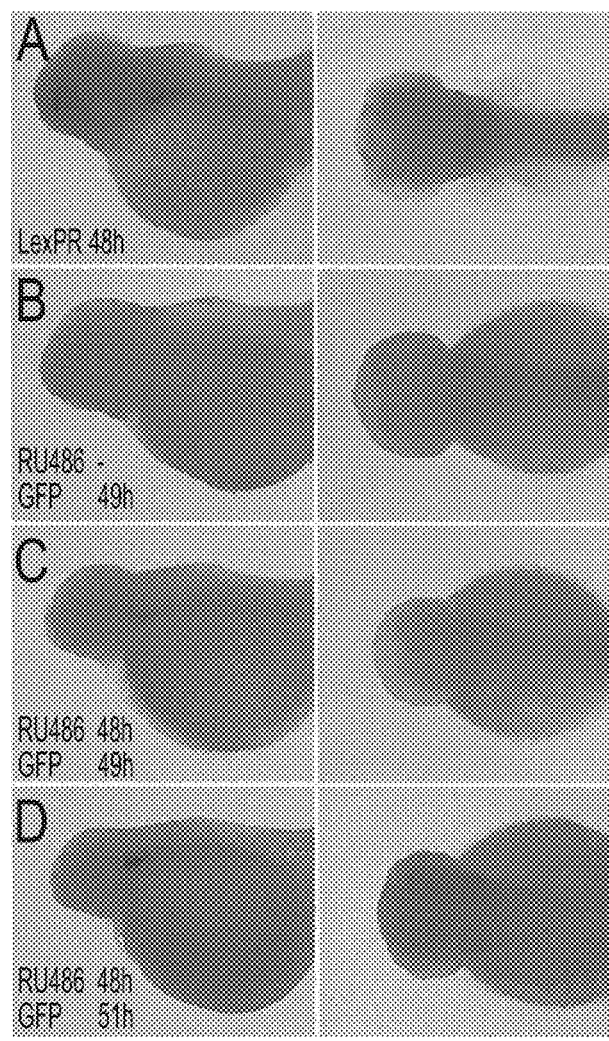
FIGS. 6A-6G show the rate of mifepristone-induced activation of transcription. In situ hybridization to detect LexPR RNA (FIG. 6A) and EGFP RNA (FIGS. 6B-6G).
Figure 6:
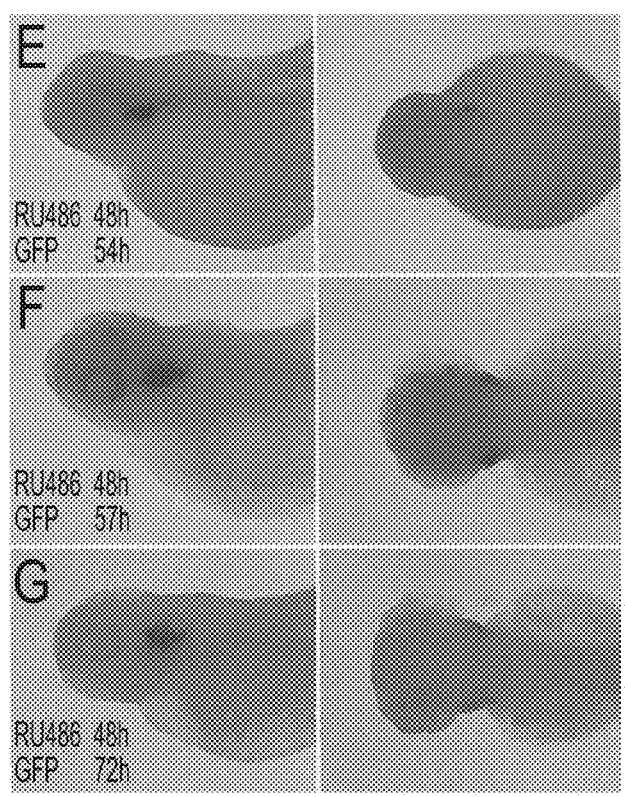

Reporter Expression in Transgenic Driver Lines is Induced and Tightly Controlled by Mifepristone Transgenic driver lines that carried LexPR driver-reporter cassette inserts in the genome were generated and produced various reporter expression patterns activated in presence of mifepristone (FIGS. 4A-4D). EGFP fluorescence was observed in the transgenic fish approximately 6-9 hours after adding mifepristone to the growth water at 1 μM and 100 nM final concentration. Strong EGFP expression could also be induced at 10 nM after 24 hours of incubation. The lowest inducible 1 nM concentration generated significantly weaker reporter expression. Importantly, in the absence of mifepristone, neither EGFP fluorescence nor EGFP transcript were detected in transgenic embryos (FIG. 5/lane 1; FIG. 6B and data not shown). Therefore, this expression system allows tight transcriptional control of the transgene with no detectable background.

Figure 7:
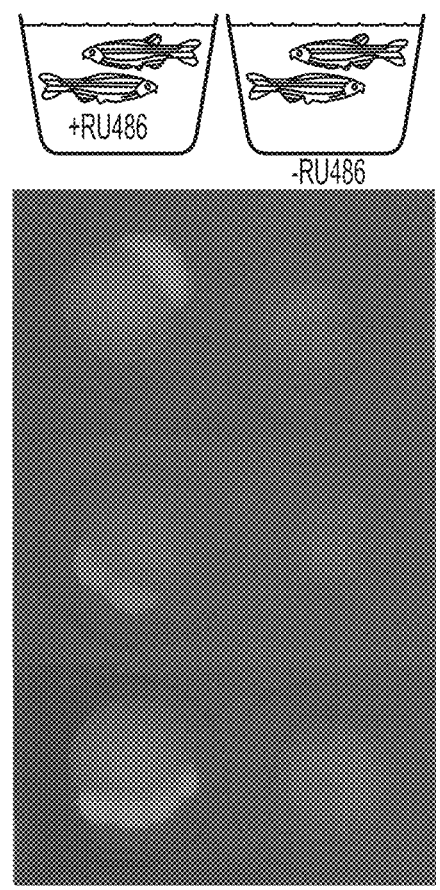
FIG. 7 shows that control of maternal expression in the transgenic fish that harbor an enhancer trap insertion of krt8:LexPR/LexOP:EGFP construct drives maternal expression of LexPR transactivator. A transgenic $F_2$ female and a WT male were placed in the crossing tank containing 1 µM mifepristone approximately 12 hours before the fertilization. All the $F_3$ embryos showed maternal EGFP expression (left panel). In contrast, the offspring of the transgenic females untreated with mifepristone did not express EGFP at the early stages (right panel). The embryos are shown at 1, 4 and 8-cell stages.
Figure 8:
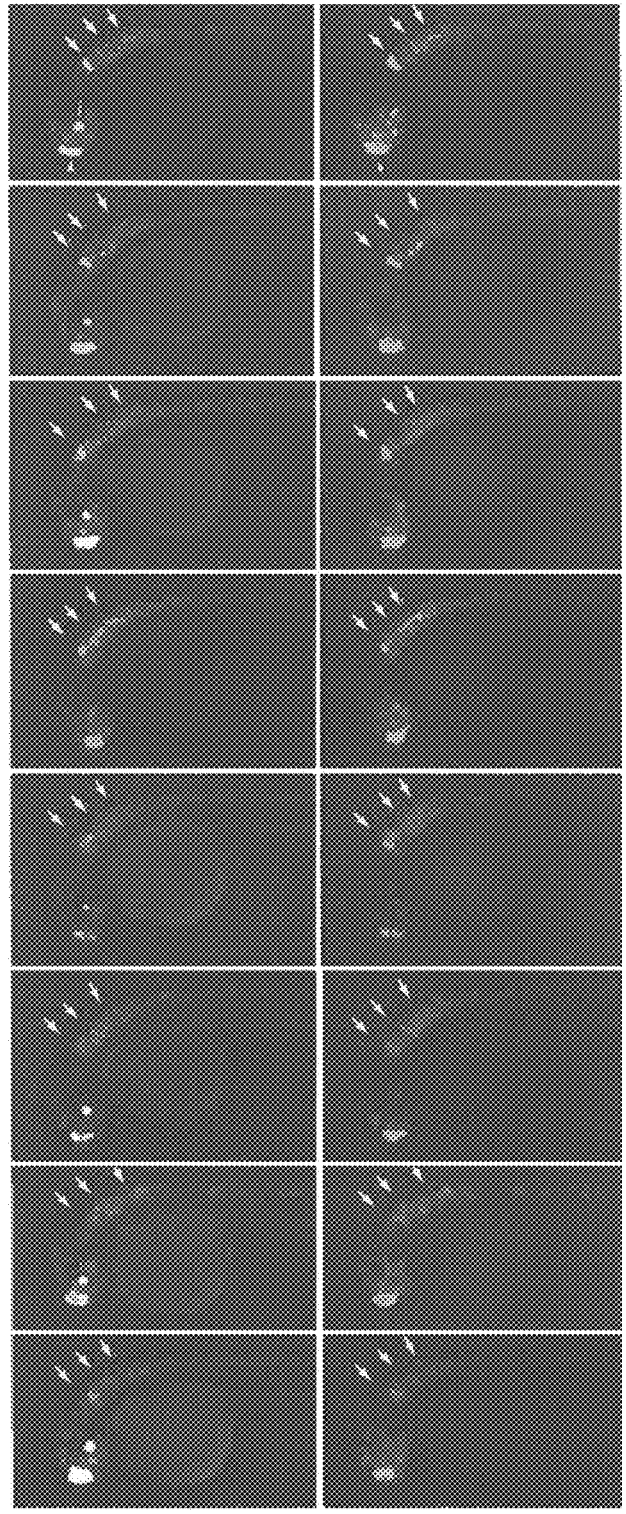
FIGS. 8A-8C show the uniformity and consistency of expression in double transgenic fish that harbor a driver-reporter promoter:LexPR/LexOP:EGFP and an effector LexOP:mCherry/cry:ECFP constructs. Effector construct contains permanent selection marker crystallin:ECFP which produces cyan expression in the lens (thin arrow) visible through the GFP filter set but not through the mCherry filter set. For these figures, two different driver-reporter lines with the same promoter were crossed to the same effector line. The gfap:LexPR/LexOP:EGFP driver-reporter construct harbors the LexPR transactivator sequence under control of the gfap (glial fibrillary acidic protein) promoter that results in expression of the EGFP reporter in the central nervous system.
Figure 8:
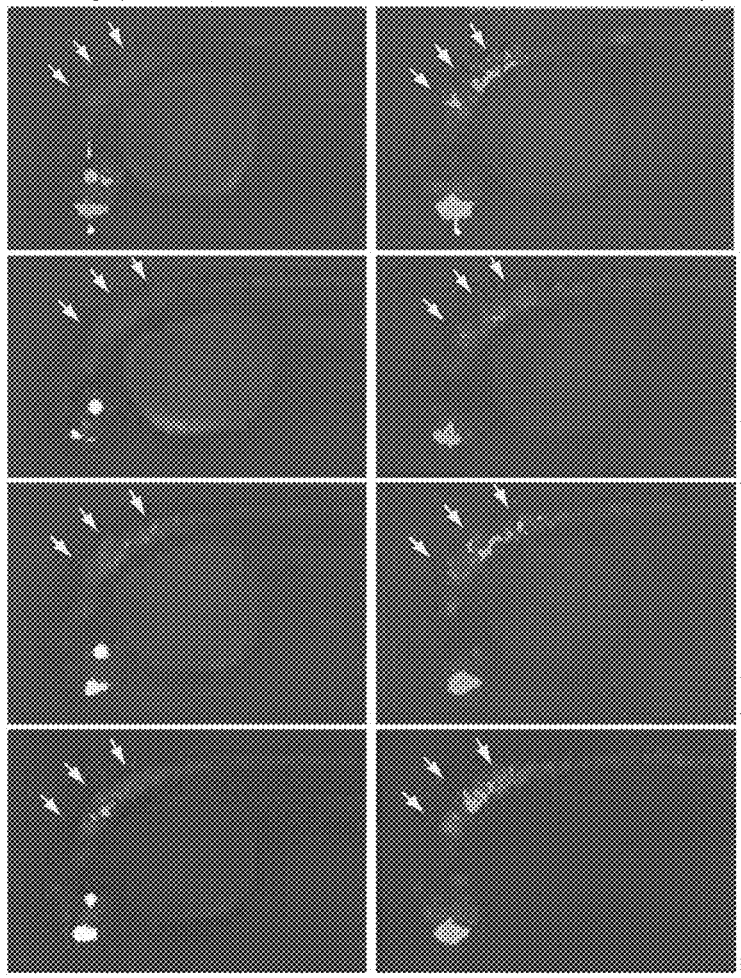
Figure 8:
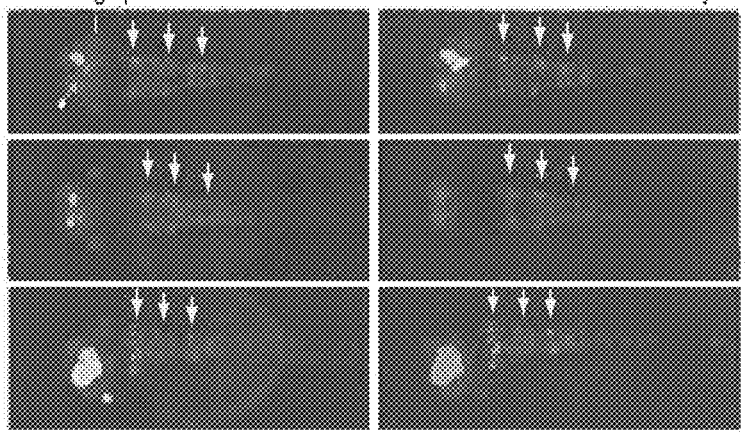

Although, krt8 promoter does not turn on until 4.5 hpf (Gong et al., 2002), we generated transgenic fish with maternal expression from this promoter via enhancer-trapping (Parinov et al., 2004), and tested the ability of this system to regulate maternal expression of transgenes. Transgenic $F_2$ females harboring the driver-EGFP construct in their genomes were treated with 1 μM mifepristone for 12 hours before crossing to the wild type males and their offspring was screened for EGFP fluorescence before midblastula transition. We have isolated females from two families that produced GFP-positive eggs following such treatment (FIG. 7). Therefore, LexPR gene expression system can be used to regulate maternal expression of transgenes.

We did not observe obvious side effects on zebrafish development using this system even upon induction with high concentration of mifepristone (10 μM) at 1-cell stage (data not shown). Although in one line induction of strong expression during early development occasionally caused developmental delay in some embryos, they later recovered and did not exhibit morphological abnormalities.

Example 6

Rate of the Transcription Induction

To accurately estimate the rate of induction, it is more appropriate to measure the transcript rather than the protein product, especially if the gene of interest contains sequences for RNAi, microRNA or other non-coding RNAs. Hence, we examined the spatiotemporal transcription response to mifepristone induction using whole mount in situ hybridization to detect EGFP transcripts (FIGS. 6B-6G). For this purpose, we used a transgenic driver line with an enhancer trap EGFP expression pattern shown in FIG. 4A. The $F_2$ embryos from this line were treated with 1 μM mifepristone from 48 hpf onwards and aliquots of 20 embryos were collected at various times after induction. No reporter transcript expression was observed without induction. The reporter transcript was first detected under the otic vesicle/ears 1 hour post-induction and its level increased gradually during first 9 hours of induction.

EGFP transcript was observed within a subset of the LexPR expression pattern (FIGS. 6A-6G), mostly in the areas of strong LexPR expression.

Example 7

Trans-Activation of Effector Expression in Double Transgenic Fish Harboring Driver and Effector Constructs

Figure 11:
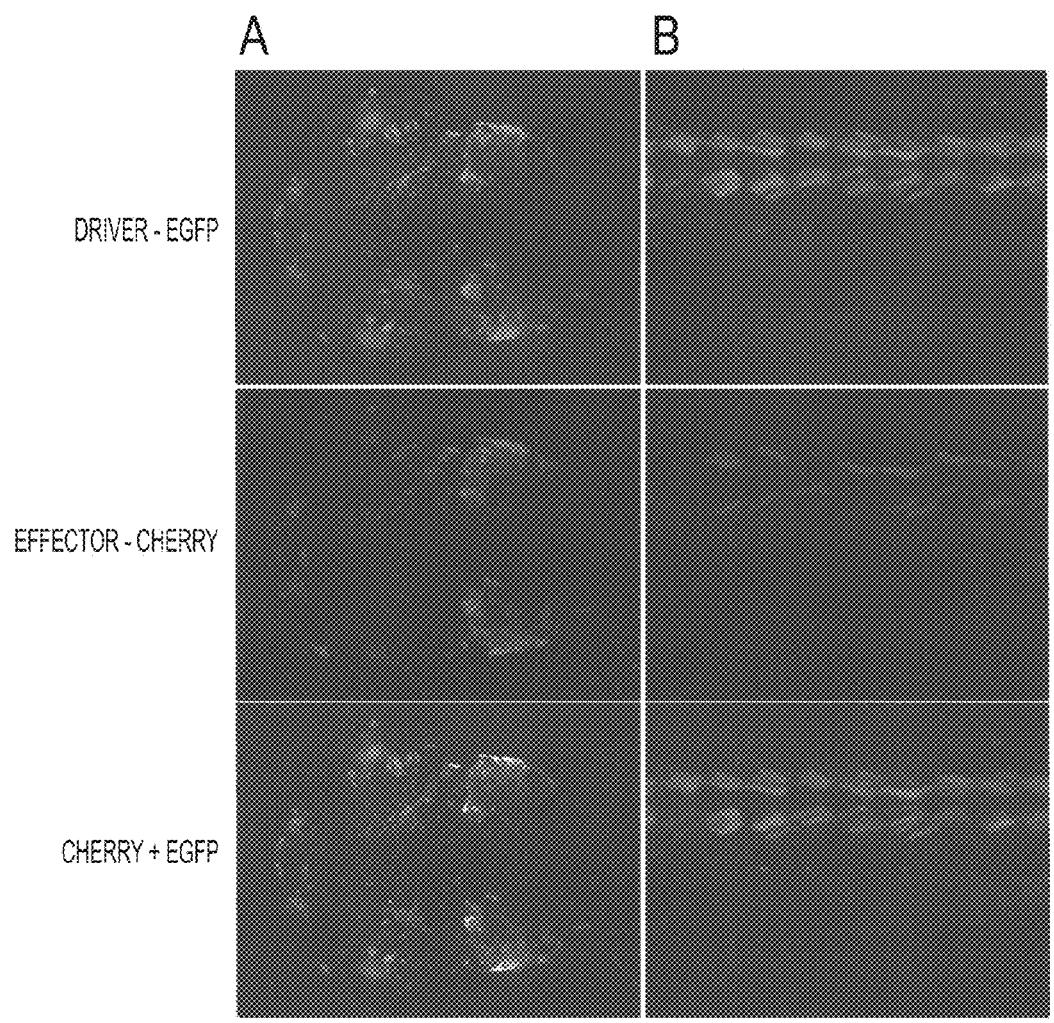
FIGS. 11A and 11B show driver-effector trans-activation. Two independent driver lines with different LexPR transactivator expression patterns (shown on FIGS. 4A, 4D) were crossed with two independent transgenic effector lines, which carried mCherry gene under control of the LexOP. The hybrid $F_3$ embryos that were double transgenic for the driver and effector cassettes were treated with 1 µM mifepristone from 24 hpf onwards.
Figure 12:
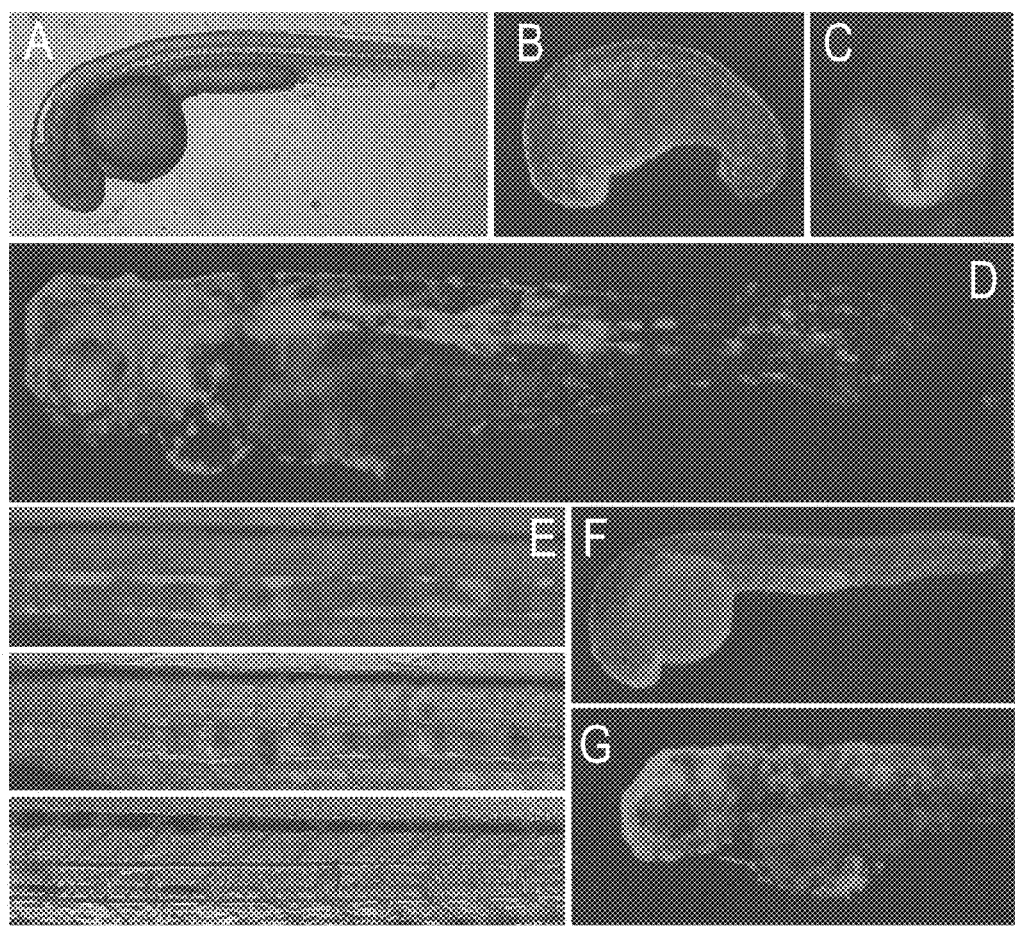
FIGS. 12a-12g show the inducible expression of EGFP-Kras$^{V12}$ in transgenic zebrafish. Transgenic zebrafish line harboring insertion of the binary driver construct Ds(krt8:LPR-LOP:EGFP-Kras$^{V12}$) containing EGFP-Kras$^{V12}$ under control of the LexOP, $F_2$ (FIG. 12a-12e, FIG. 12g).
Figure 13:
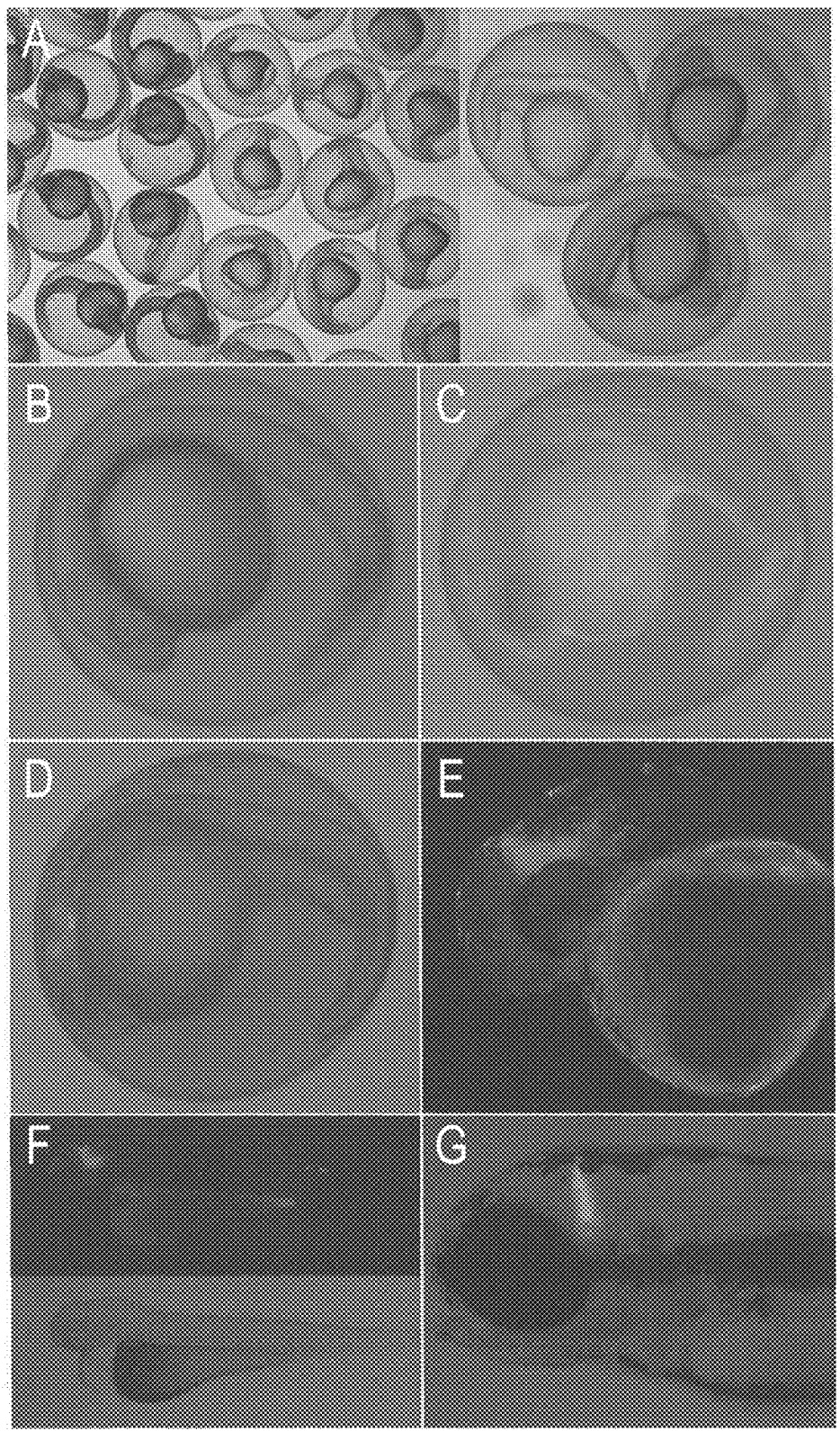
FIGS. 13a-13g show side effects caused by strong early expression of Gal4/UAS-based expression systems.

To demonstrate the feasibility of using LexPR driver lines to drive transgene expression in trans (FIGS. 1A-1B), we generated a LexA-effector construct pDs(cry:C-LOP:Ch). This effector cassette harbors a gene for red fluorescent protein "mCherry" under the control of the LexOP sequence (Example 3). It also contains Ds cis-required sequences to facilitate transposon-mediated integration into the genome and an extra selection marker, ECFP under the control of the zebrafish Crystallin beta B promoter, which generated cyan fluorescence in the lens (FIGS. 8A-8C, 9A, 9B and 10A-10D). The presence of the additional marker facilitates generation, selection and analysis of transgenic lines. Five stable transgenic lines carrying the LexA-effector inserts in their genome were generated. No background mCherry fluorescence was detected in any of the effector lines treated with 1 µM mifepristone. The effector lines were crossed with the driver-EGFP lines and the transgenic lines carrying both constructs in their genomes were obtained. No background EGFP and mCherry fluorescence was detected in the double transgenic fish prior to treatment with mifepristone. Upon treatment of the double transgenic embryos with 1 µM mifepristone, both reporters (EGFP/driver and mCherry/effector) were co-expressed in the same cells (FIGS. 11A and 11B). Thus, the driver lines can be used for trans-activation of the genes of interests cloned into the effector cassette.

Figure 9:
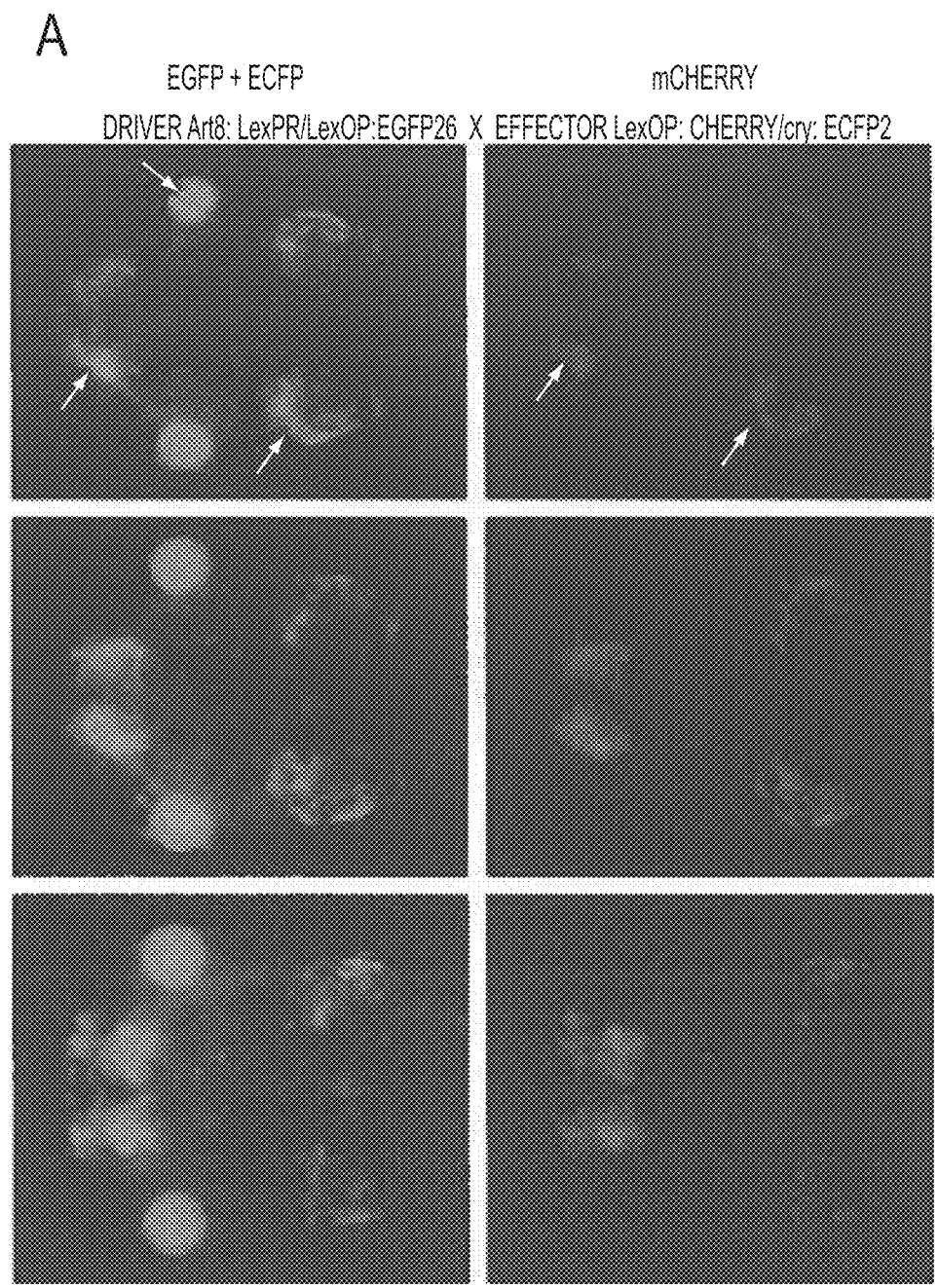
FIGS. 9A and 9B show the same driver line as in FIGS. 8A-8C crossed to two independent effector lines. The driver line contains an enhancer trap insertion of krt8:LexPR/LexOP:EGFP construct that results in expression of the EGFP reporter in the forebrain (arrowhead) and in the otic capsule (large arrow).
Figure 9:
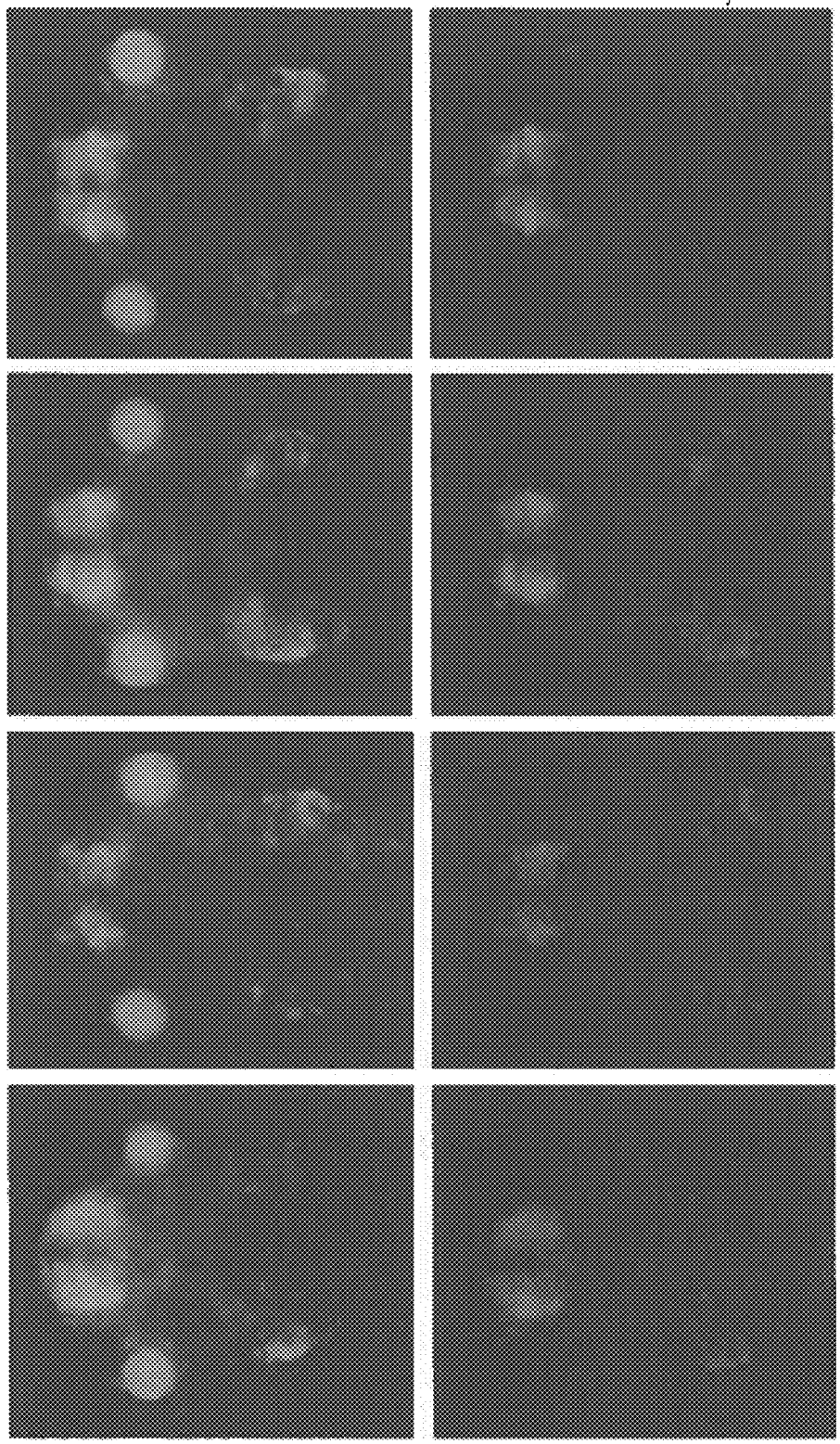
Figure 10:
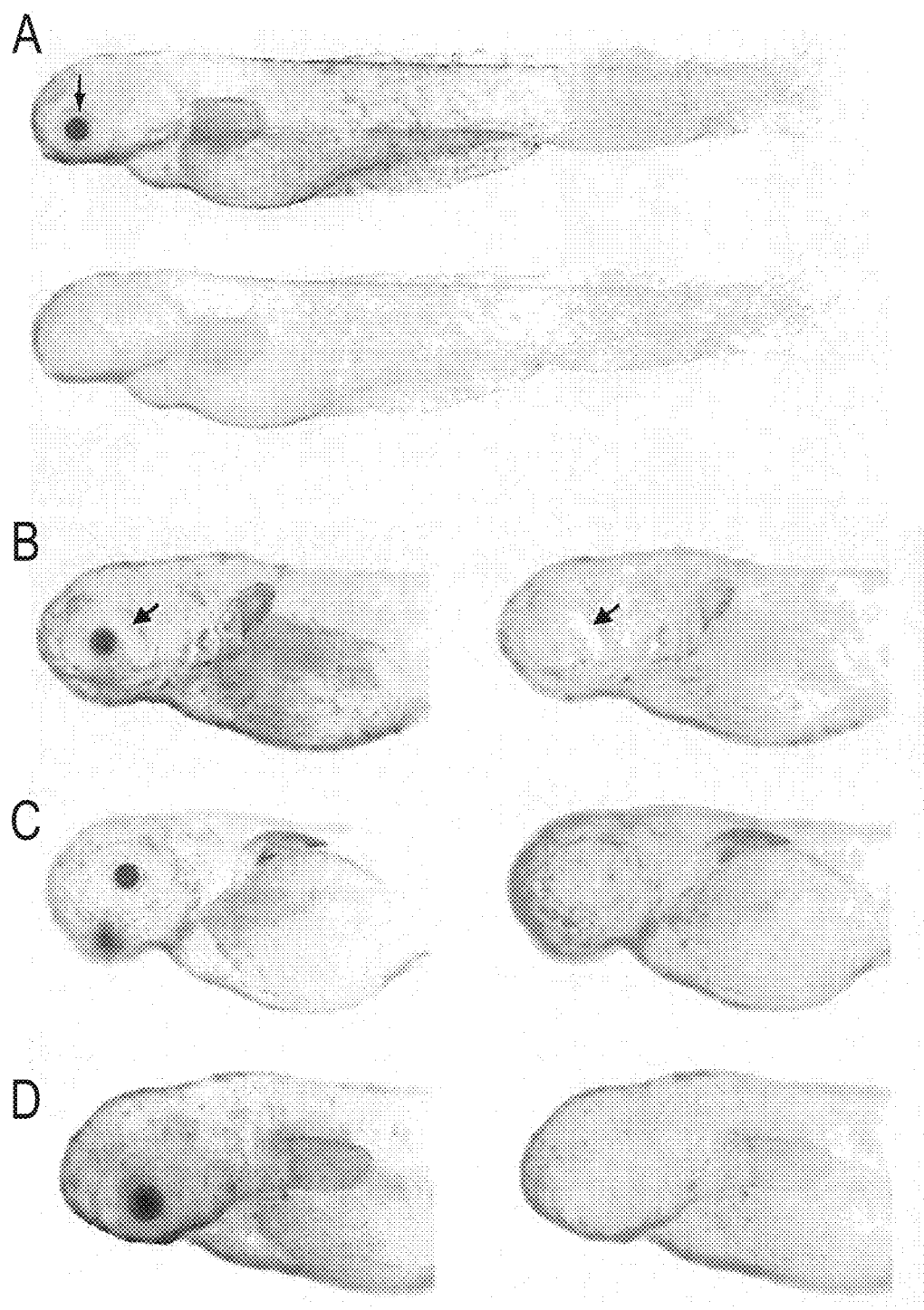
FIGS. 10A-10D show mosaic reporter expression in the skin epithelia. Double transgenic fish that harbor a driver krt8:LexPR/LexOP:EGFP and an effector LexOP:mCherry/cry:ECFP construct insertions are shown. The driver construct contains a promoter of the keratin8 (krt8) gene that drives expression of LexPR transactivator in the single layer of epithelial skin cells of the same type. Shown are four $F_2$ fish from the same offspring. Although most epithelial cells express both reporters, there is visible variation of intensity between cells. There are also patches of cells that express very week level of both reporters (large arrow), that may reflect positional effects at the driver insertion site or silencing of the LexPR gene, the difference in drug permeability among the cells of the same type or other difference between these cells (age, stress etc) at the time of induction.

Nevertheless, we observed variegation in the relative expression levels of both reporters (FIGS. 11A, 11B, 8A-8C, 9A, 9B and 10A-10D). Variegation was evident even among cells of the same type in the same fish (FIG. 11B). Most positive cells expressed both reporters, but the relative level of expression varied significantly: some cells showed brighter EGFP fluorescence than mCherry while in some others the mCherry fluorescence was brighter. Three different effector lines crossed to the same driver line produced slightly different general levels of reporter (mCherry) expression (data not shown), but the differences between the effector lines were not more significant than the variegation observed between different fish within each offspring (FIGS. 9A and 9B).

Example 8

Delayed Downregulation of the Reporter Gene Expression Following Mifepristone Withdrawal

To find out if removal of mifepristone allows switching off gene expression, and to determine the time needed for downregulation after mifepristone withdrawal, we performed the following experiment. Transgenic $F_2$ embryos carrying the driver-reporter construct were treated at 36 hpf with four different concentrations of mifepristone for 1 or 12 hours to induce the EGFP reporter expression. After 1 or 12 hours of mifepristone treatment, the embryos were rinsed and transferred into larger tanks of water without mifepristone. EGFP fluorescence was observed and recorded at different times after withdrawal of mifepristone. In parallel, we also observed embryos that were continuously treated with the drug. The results of the experiment are shown in Table 4 and summarized in Table 5. The data in Table 4 is aligned according to time after mifepristone withdrawal, that corresponds to different developmental timing (hpf) for the embryos treated for 1 hour and 12 hours 9 both treatments started at 36 hpf). To avoid confusion, the corresponding developmental times are indicated. A Nikon SMZ1600 fluorescent stereomicroscope was used for rough estimation of the EGFP fluorescence. Relative brightness between the experiment and the control embryos continuously treated with 1 µM mifepristone is arranged in three levels as indicated in Table 4. We observed EGFP fluorescence in the embryos for 5 days in mifepristone-free water following 12 hours treatment with 1 µM mifepristone (Table 4). EGFP transcript was also detected by RT-PCR 5 days after withdrawal of mifepristone from the water (FIG. 5, lane 5). By lowering the concentration to 10 nM and decreasing the length of exposure length to 1 hour, the switch off delay can be shortened (Tables 4 and 5), but the maximum expression level produced under these induction conditions is lower.

TABLE 4

Determining the Time Required to Switch Off Reporter Expression

| $C_{RU486}$ | RU486 incubation | | Reporter expression after RU486 withdrawal (time after RU486 withdrawal) | | | | | | |
|---|---|---|---|---|---|---|---|---|---|
| | 1 h | 12 h | 12 h | 24 h | 48 h | 72 h | 96 h | 120 h | 144 h |
| 1 hour RU486 incubation - withdrawal | | | | | | | | | |
| | 37hpf | | 49hpf | 61hpf | 85hpf | 109hpf | 133hpf | 157hpf | 181hpf |
| 1 µM | − | | + | + | + | ± | ± | − | − |
| 100 nM | − | | + | + | − | − | − | − | − |
| 10 nM | − | | ± | − | − | − | − | − | − |
| 1 nM | − | | − | − | − | − | − | − | − |
| 12 hours RU486 incubation - withdrawal | | | | | | | | | |
| | | 48hpf | 60hpf | 72hpf | 96hpf | 120hpf | 144hpf | 168hpf | 192hpf |
| 1 µM | | + | + | + | + | ± | ± | ± | − |
| 100 nM | | + | + | ± | ± | − | − | − | − |
| 10 nM | | ± | + | ± | − | − | − | − | − |
| 1 nM | | − | ± | − | − | − | − | − | − |

TABLE 4-continued

Determining the Time Required to Switch Off Reporter Expression

| | Continuous induction (time of RU486 incubation) | | | | |
|---|---|---|---|---|---|
| | 1 h | 12 h | 13 h 49hpf | 24 h 60hpf | 24-156 h 60-192 hpf |
| 1 µM | − | + | + | + | + |
| 100 nM | − | + | + | + | + |
| 10 nM | − | ± | ± | + | + |
| 1 nM | − | − | − | ± | ± |

+ Fluorescence signal is similar to the control.
± Fluorescence signal is obviously weaker that in control.
− No EGFP fluorescence (except autofluorescence)observed using the fluorescent stereomicroscope.

TABLE 5

Minimal Time After Mifepristone
Withdrawal Required to Switch Off Reporter Expression

| | Minimal time after RU486 withdrawal to turn off the reporter expression | |
|---|---|---|
| $C_{RU486}$ | 1 hour induction | 12 hours induction |
| 1 µM | 5 days | 6 days |
| 100 nM | 2 days | 3 days |
| 10 nM | 1 day | 2 days |
| 1 nM | — | 1 day |

Example 9

Inducible Expression of Activated K-ras$^{V12}$ in Transgenic Zebrafish Using a Single Driver-Reporter Vector To demonstrate practical application of the LexPR gene expression system we used it for generating transgenic zebrafish lines carrying the cell-toxic K-ras$^{V12}$ oncogene to test if it is possible to manipulate its expression during development.

We had previously attempted to generate enhancer trap lines that express a fusion protein of EGFP and activated K-ras2B(V12) (EGFP-Kras$^{V12}$ hereafter) using Ds(krt8: EGFP-Kras$^{V12}$) transgene (unpublished data). However, expression of EGFP-Kras$^{V12}$ drastically reduced germline penetrance and, despite the reported efficiency of this promoter for enhancer trapping (Parinov et al., 2004), we obtained very few lines that expressed EGFP-Kras$^{V12}$ exclusively in skin epithelia. The epithelial cells in these lines were severely abnormal, but it did not affect development or viability.

To overcome the toxicity of the EGFP-Kras$^{V12}$ transgene, we cloned it into a driver-reporter cassette (instead of the EGFP in Example 2) and used the resulting construct Ds(krt8: LPR-LOP:EGFP-Kras$^{V12}$) (SEQ ID NO:48; EGFP-Kras$^{V12}$ comprises nucleotides 4415-5710; the sequence comprising nucleotides 4396-5710, which contains EGFP-Kras$^{V12}$, has been previously described in PCT published application No. WO 2007/011312) to generate transgenic fish. We used short pulse of exposure to mifepristone (100 nM mifepristone for 1 hour) at the 24-hpf stage to screen $F_1$ embryos. This was done to ensure survival of transgenic fish.

The first result was restoration of germline penetrance of the transgene: we have obtained 7 out of 8 screened founders (88% transgenesis rate), which produced transgenic progeny with different GFP fluorescence patterns when induced with mifepristone. This transgenesis rate is similar to the transgenesis rate of the Ds(krt8:EGFP) transgene (Emelyanov et al., 2006), suggesting that Ds(krt8:LPR-LOP:EGFP-Kras$^{V12}$) cassette did not affect germline penetrance. In one of these lines, expression of the transgene could be induced in the developing forebrain, notochord sheath cells, as well as in the epithelial skin cells attributed to the basic krt8 promoter activity (FIGS. 12a-12g). To induce EGFP-Kras$^{V12}$ expression in this line, we treated $F_2$ embryos with 10 µM mifepristone at 10 hpf onwards. This caused specific effect on the shape of cells that express EGFP-Kras$^{V12}$: cells of the skin epithelia and notochord sheath were enlarged, did not form a continuous layer but instead, we observed clusters of cells. The affected skin epithelial cells lost contacts with the embryo and eventually shed to the outside environment. Embryos had shortened axis, abnormal brain, cranial structures, branchial arches and muscles (FIGS. 12a-12g). Thus, embryo development was severely affected by expression of Kras$^{V12}$.

This model demonstrates the ease and feasibility of generating and manipulating transgenic animals that harbor toxic transgenes. This strategy should be useful to study effects of not only Ras activity, but also other oncogenes/factors in the development of various organs and tissues in zebrafish and in cancer research.

Non-inducible gene expression systems utilizing the LexA DNA binding domain have been previously used only in invertebrates and in mammalian cell cultures (Hoshino et al., 2004; Lai and Lee, 2006; Nettelbeck et al., 1998; Szuts and Bienz, 2000). Here, we have demonstrated that a LexA-based transcription activation system can be used for inducible gene expression in vivo in true transgenic vertebrates and for generating transgenic driver lines.

The LexA-based mifepristone-inducible system provides stringent control of gene expression with no detectable basal expression of the reporter-gene in the absence of mifepristone. The induction of transcription is relatively fast since the transcript become detectable as early as one hour after induction with 1 µM mifepristone and achieve maximum level after approximately nine hours of induction.

Transgene expression can be induced at any developmental stages and throughout the adult life. Moreover, we were able to induce expression of maternal products in the egg by exposing females to mifepristone before fertilization. This is essential when studying the effects of a transgene on early development before activation of the zygotic genome at mid-blastula transition (Pelegri, 2003). It would also allow the control of expression in germ cells of true transgenic fish even when the transgene expression in these cells is detrimental.

The expression can also be switched off, but at a much slower rate as compared to induction. Even at five days after mifepristone withdrawal (following 12 hours induction with 1 µM mifepristone) the reporter transcript can be detected by RT-PCR. It is possible that mifepristone is stable and remains in the tissues long after washout or it may accumulate in the yolk due to its hydrophobicity. Other factors include stability of the LexPR and GFP transcripts/proteins. Lower concentrations of mifepristone and shorter induction time are more appropriate for switch-off experiments. Published data from mouse and Drosophila show that both the RU486- and the tetracycline-inducible systems require long time to turn off (Chikama et al., 2005; Roman et al., 2001). Thus, our system although very effective in switching on transgene expression, may need to be optimized further for switch-off experiments. Table 5 provides a rough guide for optimization of the concentration and induction time.

Transcription from the LexOP is activated only in a subset of cells expressing the LexPR transcription factor (FIGS. 6A-6G), mostly in the cells with relatively high concentration of the LexPR. However, some cells that expressed low levels of LexPR transactivator produced high levels of EGFP transcript, suggesting that activation is not simply dose dependent and may be subject to regulation by other factors. It was previously reported that transactivator concentration could be an important parameter in the activation of target genes for TetR-VP16/tetO inducible binary system (Boger and Gruss, 1999). Stronger promoters and enhancer trap events or the use of multiple insertion driver lines may produce broader expression of a target gene. Other possibilities that may explain this include cell-specific factors involved in $p65^{AD}$ transcriptional activation, or cell-specific drug impermeability. This must be taken into account when making an inducible driver line using a well-defined promoter or a transgenic line with uniform ubiquitous expression. Depending on the task, specific expression of the target gene in the smaller domain compared to the larger expression domain of the transactivator can be an advantage, since it may allow activating expression in specific cells vs a whole organ.

In the cells where EGFP expression was induced, there was much more EGFP than LexPR transcript, that shows that the LexPR/LexOP system efficiently amplifies the expression of the target genes.

Transgenic LexPR lines produce consistent expression from the LexOP: different animals belonging to the same line show similar expression pattern (FIGS. 8A-8C, 9A, 9B and 10A-D). Furthermore, two independent LexOPs within the same animal (driver and effector) also produce matching patterns of expression (FIGS. 11A, 11B, 8A-8C, 9A, 9B and 10A-D). Nevertheless, we observed variegation of reporter expression among the embryos from the same offspring (FIGS. 8A-8C, 9A, 9B and 10A-D), and mosaic activation of the reporters among the cells of the same type, which appeared visually similar to position-effect variegation (FIGS. 11B, 8A-8C, 9A, 9B and 10A-D). Mosaic activation of reporter expression was more apparent in double transgenic lines that harbored driver and effector constructs that allowed comparison of one reporter expression against another (FIG. 11B). Not only the relative brightness ratio of the different reporters but also individual expression from each LexOP varied independently among the cells of same type, suggestive of some variations in chromatin status around the same insertion site. Different effector lines produced similar degrees of mosaicism, suggesting that position effect variegation does not play a major role in the variegation. This is further supported by the facts that position effect variegation was rarely observed in the conventional enhancer trap lines carrying EGFP gene directly controlled by the krt8 promoter (Choo et al., 2006; Parinov et al., 2004) but most of the LexPR driver lines showed certain degrees of mosaicism. Published reports suggest that epigenetic silencing through DNA methylation and chromatin acetylation play important roles in activator-dependent transgene expression. (Boger and Gruss, 1999; Kues et al., 2006). The mosaic induction of gene expression may also reflect a stochastic mechanism of transactivator-dependent transcription activation (Boger and Gruss, 1999; Walters et al., 1995). Variability and mosaicism of transgene expression is a common problem of binary inducible systems and it has been observed with the tetracycline dependent activation systems in transgenic mice (Boger and Gruss, 1999; Furth et al., 1994; Gimenez et al., 2004; Kues et al., 2006; Yamamoto et al., 2001). Furthermore, similar variegation of reporter expression levels has been noticed in the non-inducible Gal4-VP16/UAS transgenic zebrafish lines (Davison et al., 2007; Scott et al., 2007)(data not shown), mifepristone-inducible Gal4-p65/UAS transgenic zebrafish lines (data not shown) and in the non-inducible GAL4/UAS Drosophila lines (Goentoro et al., 2006). Therefore, this problem may be inherent to all binary gene expression systems. Because of the mosaicism, concentration of the reporter gene expressed from one LexOP cannot be used as a quantitative indicator of the target gene expression from another LexOP. Thus, visualization of the transgene expression using independent live reporters, although very useful, must be interpreted with caution. Expression of the gene of interest in specific cells can be confirmed post experimentally by in situ hybridization.

We have previously tested the non-inducible (Koster and Fraser, 2001) and the chemical-inducible (Burcin et al., 1999) gene expression systems that utilized the DNA binding domain of the yeast GAL4 protein in germline-transgenic zebrafish (FIGS. 13a-13g and data not shown). These systems could drive expression (constitutive and inducible respectively) of the UAS-regulated transgenes, but caused non-specific developmental defects at a high frequency when expressed at early developmental stages (FIGS. 13a-13g). The mifepristone-inducible GAL4-system (Burcin et al., 1999) often produced irregular expression and the lines with background expression even without induction (data not shown). Contrary to the GAL4-based systems, the LexA-based system described here did not cause obvious adverse effects on zebrafish development even when mifepristone was added at early developmental stages, it generated more uniform expression and non of the LexPR driver and effector lines showed background expression. This may be not entirely attributable to the different properties of the GAL4 and LexA DNA binding domains and their basic recognition DNA sequences, but to the design of GAL4-based transactivators, number of UAS elements, promoters and to other important regulatory elements of the system. Nevertheless, several zebrafish laboratories began generating GAL4-based driver lines (Davison et al., 2007; Scott et al., 2007). Since LexA- and GAL4-based systems do not cross-react, it would be possible to use and control them together in the same animal independently, allowing more sophisticated experimental setups.

The concentration of mifepristone required for effective transcription induction (0.01-1 µM in the growth water) is significantly lower (20 to 2000-fold lower) than the anti-progestin dosage used to induce abortion (10 mg/kg, ~20 µM). This offers safety for the researchers and the environment. Since the deletion mutant of the human progesterone receptor LBD does not bind to progesterone, this may also be potentially useful for human gene therapy (Wang et al., 1994).

Although mifepristone is cheap and safe, in some cases prolonged exposure to the drug may be undesirable. Furthermore, due to strong transcript amplification, it might be difficult to control the level of the target gene expression by titration of mifepristone concentration. Combination of the inducible system with Cre/lox recombination system can provide a platform for improvements (Zuo et al., 2001). Indeed, inducible expression of Cre recombinase alone would be a significant improvement of the Cre/lox recombination system (Kellendonk et al., 1999).

The system of the present invention features all elements that are necessary for direct generation of transgenic lines carrying any gene of interest or for performing large-scale driver-line screenings, and subsequent application of these lines to drive controllable expression of genes of interest. The driver and the effector DNA cassettes are equipped with the Ds cis-required sequences to facilitate transgenesis. The constructs contain convenient restriction enzyme recognition sites that allow single-step replacement of the EGFP and mCherry coding sequences with a sequence of interest (Examples 2 and 3). The 0.5-kb krt8 promoter driving the transactivator expression can be used for enhancer trapping (Parinov et al., 2004), or can also be easily replaced with different promoters (Example 2).

Most elements of these constructs have been previously tested and used in very distant hosts: bacterial LexA DNA binding domain and operator were utilized in plants, invertebrates and in vertebrate cell cultures (Nettelbeck et al., 1998; Szuts and Bienz, 2000; Zuo et al., 2000); the hormone binding domain of human progesterone receptor (hPR-LBD) was explored in yeast (Vegeto et al., 1992); NF-κB/p65 activation domain was shown to activate transcription in yeast (Moore et al., 1993); maize Ac/Ds transposable elements performed well in plants, fungal and animal kingdoms (Emelyanov et al., 2006); 35S CaMV plant virus minimal promoter and *Agrobacterium* Nos terminator were used in plants (Zuo et al., 2000); EGFP, mCherry and ECFP perform well in all tested organisms and the zebrafish krt8 promoter is active in human and mouse cell cultures (Parinov and Emelyanov, unpublished data). Thus, this system and our constructs can be used in a wide range of hosts from amphibians to mammals, and possibly in invertebrates, fungi and plants.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Andersen, J. K. et al. (1993). "Herpesvirus-mediated gene delivery into the rat brain: specificity and efficiency of the neuron-specific enolase promoter." *Cell Mol Neurobiol* 13, 503-515.

Balciunas, D. et al. (2004). Enhancer trapping in zebrafish using the Sleeping Beauty transposon. *BMC Genomics* 5(1), 62.

Bajoghli, B. et al. (2004). An artificial promoter construct for heat-inducible misexpression during fish embryogenesis. *Dev Biol* 271, 416-30.

Boger, H. and Gruss, P. (1999). Functional determinants for the tetracycline-dependent transactivator tTA in transgenic mouse embryos. *Mech Dev* 83, 141-53.

Burns, J. C. et al. (1993). "Vesicular stomatitis virus G glycoprotein pseudotyped retroviral vectors: concentration to very high titer and efficient gene transfer into mammalian and nonmammalian cells." *Proc Natl Acad Sci USA* 90, 8033-8037.

Burcin, M. M. et al (1999). Adenovirus-mediated regulable target gene expression in vivo. *Proc Natl Acad Sci USA* 96, 355-360.

Chen, T. T. and Powers, D. A. (1990). "Transgenic fish." *Trends Biotechnol* 8, 209-215.

Chikama, T. et al. (2005). Characterization of tetracycline-inducible bitransgenic Krt12rtTA/+/tet-O-LacZ mice. *Invest Opthalmol Vis Sci* 46, 1966-72.

Choo, B. G. et al. (2006). Zebrafish transgenic Enhancer TRAP line database (ZETRAP). *BMC Dev Biol* 6, 5.

Culp, P. et al. (1991). "High-frequency germ-line transmission of plasmid DNA sequences injected into fertilized zebrafish eggs." *Proc Natl Acad Sci USA* 88, 7953-7957.

Das, B. and Brown, D. D. (2004). Controlling transgene expression to study *Xenopus laevis* metamorphosis. *Proc Natl Acad Sci USA* 101, 4839-4842.

Davidson, B. L. et al. (1993). "A model system for in vivo gene transfer into the central nervous system using an adenoviral vector." *Nature Genetics* 3, 219-223.

Davison, J. M. et al. (2007). Transactivation from Gal4-VP16 transgenic insertions for tissue-specific cell labeling and ablation in zebrafish. *Dev Biol* 304, 811-24.

Ebina, Y. et al. (1983). LexA protein is a repressor of the colicin E1 gene. *J Biol Chem* 258, 13258-13261.

Emelyanov, A. et al. (2006). Trans-kingdom transposition of the maize dissociation element. *Genetics* 174, 1095-1104.

Esengil, H. et al. (2007). Small-molecule regulation of zebrafish gene expression. *Nat Chem Biol* 3, 154-5.

Erzurum, S. C. et al. (1993). "Protection of human endothelial cells from oxidant injury by adenovirus-mediated transfer of the human catalase cDNA." *Nucleic Acids Res* 21, 1607-1612.

Fletcher, G. L., and Davis, P. L. (1991). "Transgenic fish for aquaculture." In *Genetic Engineering*, Setlow, J. K., ed., Plenum Press.

Furth, P. A. et al. (1994). Temporal control of gene expression in transgenic mice by a tetracycline-responsive promoter. *Proc Natl Aced Sci USA* 91, 9302-6.

Gimenez, E. et al. (2004). A transgenic mouse model with inducible Tyrosinase gene expression using the tetracycline (Tet-on) system allows regulated rescue of abnormal chiasmatic projections found in albinism. *Pigment Cell Res* 17, 363-70.

Goentoro, L. A. et al. (2006). Quantitative analysis of the GAL4/UAS system in *Drosophila* oogenesis. *Genesis* 44, 66-74.

Gong, Z. et al. (2002). Green fluorescent protein expression in germ-line transmitted transgenic zebrafish under a stratified epithelial promoter from keratin8. *Dev Dyn* 223, 204-215.

Guo, H. S. et al. (2003). A chemical-regulated inducible RNAi system in plants. *Plant J* 34, 383-392.

Habets, P. E. et al. (2003). Cardiac expression of Gal4 causes cardiomyopathy in a dose-dependent manner. *J Muscle Res Cell Motil* 24, 205-9.

Halloran, M. C. et al. (2000). Laser-induced gene expression in specific cells of transgenic zebrafish. *Development* 127, 1953-60.

Hannon, G. and Rossi, J. (2004). Unlocking the potential of the human genome with RNA interference. *Nature* 431, 371-378.

Horii, T. et al. (1981). Nucleotide sequence of the lexA gene of *E. coli*. *Cell* 23, 689-97.

Hoshino, A. et al. (2004). Inducible translocation trap: a system for detecting inducible nuclear translocation. *Mol Cell* 15, 153-159.

Kawakami, K. et al. (2000). Identification of a functional transposase of the Tol2 element, an Ac-like element from the Japanese medaka fish, and its transposition in the zebrafish germ lineage. *Proc Natl Acad Sci USA* 97, 11403-8.

Kellendonk, C. et al. (1999). Inducible site-specific recombination in the brain. *J Mol Biol* 285, 175-182.

Kimmel, C. B. (1989). "Genetics and Early Development of Zebrafish." *Trends Genet* 5, 283-288.

Koster, R. W. and Fraser, S. E. (2001). Tracing transgene expression in living zebrafish embryos. *Dev Biol* 233, 329-346.

Kotani, T. et al. (2006). Transposon-mediated gene trapping in zebrafish. *Methods* 39, 199-206.

Kramer, J. M. and Staveley, B. E. (2003). GAL4 causes developmental defects and apoptosis when expressed in the developing eye of *Drosophila melanogaster*. *Genet Mol Res* 2, 43-7.

Kues, W. A. et al. (2006). Epigenetic silencing and tissue independent expression of a novel tetracycline inducible system in double-transgenic pigs. *FASEB J* 20, 1200-2.

Lai, S. L. and Lee, T. (2006). Genetic mosaic with dual binary transcriptional systems in *Drosophila*. *Nat Neurosci* 9, 703-709.

Lee, Y. et al. (2005). Fgf signaling instructs position-dependent growth rate during zebrafish fin regeneration. *Development* 132, 5173-83.

Lepilina, A. et al. (2006). A dynamic epicardial injury response supports progenitor cell activity during zebrafish heart regeneration. *Cell* 127, 607-19.

Lever, A. M. (2000). "Lentiviral vectors: progress and potential." *Curr Opin Mol Ther* 2, 488-496.

Lu, J. K. et al. (1992). "Integration, expression and germ-line transmission of foreign growth hormone genes in medaka (*Oryzias latipes*)." *Molec Mar Biol Biotechnol* 1, 366-375.

Miki, T. et al. (1981). Organization of the lexA gene of *Escherichia coli* and nucleotide sequence of the regulatory region. *Nucleic Acids Res* 9, 529-43.

Miller, A. D. et al., (1993). "Use of retroviral vectors for gene transfer and expression." *Methods of Enzymology* 217, 581-599.

Moore, P. A. et al. (1993). Conservation of transcriptional activation functions of the NF-kappa B p50 and p65 subunits in mammalian cells and *Saccharomyces cerevisiae*. *Mol Cell Biol* 13, 1666-74.

Nettelbeck, D. M. et al. (1998). A strategy for enhancing the transcriptional activity of weak cell type-specific promoters. *Gene Ther* 5, 1656-1664.

Ngan, E. S. et al. (2002). Inducible expression of FGF-3 in mouse mammary gland. *Proc Natl Acad Sci USA* 99, 11187-92.

Nicholson, L. et al. (2008). Spatial and temporal control of gene expression in *Drosophila* using the inducible GeneSwitch GAL4 system. I. Screen for larval nervous system drivers. *Genetics* 178, 215-34.

Oertel-Buchheit, P. et al. (1992). Isolation and characterization of LexA mutant repressors with enhanced DNA binding affinity. *J Mol Biol* 225, 609-20.

Oxtoby, E. and Jowett, T. (1993). Cloning of the zebrafish krox-20 gene (krx-20) and its expression during hindbrain development. *Nucleic Acids Res* 21, 1087-95.

Parinov, S. et al. (2004). Tol2 transposon-mediated enhancer trap to identify developmentally regulated zebrafish genes in vivo. *Dev Dyn* 231, 449-459.

Pelegri, F. (2003). Maternal factors in zebrafish development. *Dev Dyn* 228, 535-54.

Pierson, T. M. et al. (2000). Regulable expression of inhibin A in wild-type and inhibin alpha null mice. *Mol Endocrinol* 14, 1075-1085.

Powers, D. A. et al. (1992). "Electroporation: a method for transferring genes into the gametes of zebrafish (*Brachydanio rerio*), channel catfish (*Ictalurua punctatus*), and common carp (*Cyprinus carpio*)." *Molec Mar Biol Biotechnol* 1, 301-308.

Roman, G. et al. (2001). P[Switch], a system for spatial and temporal control of gene expression in *Drosophila melanogaster*. *Proc Natl Acad Sci USA* 98, 12602-7.

Ruvkun, G. (2001). Molecular biology. Glimpses of a tiny RNA world. *Science* 294, 797-799.

Scott, E. K. et al. (2007). Targeting neural circuitry in zebrafish using GAL4 enhancer trapping. *Nat Methods* 4, 323-326.

Skarnes, W. C. et al. (1992). A gene trap approach in mouse embryonic stem cells: the lacZ reported is activated by splicing, reflects endogenous gene expression, and is mutagenic in mice. *Genes Dev* 6, 903-918.

Stanford, W. L. et al. (2001). Gene-trap mutagenesis: past, present and beyond. *Nat Rev Genet* 2, 756-768.

Streisinger (1984). Attainment of Minimal Biological Variability and Measurements of Genotoxicity: Production of Homozygous Diploid Zebra Fish. *Natl. Cancer Inst. Monogr* 65, 53-58.

Szuts, D. and Bienz, M. (2000). LexA chimeras reveal the function of *Drosophila* Fos as a context-dependent transcriptional activator. *Proc Natl Acad Sci USA* 97, 5351-6.

Vegeto, E. et al. (1992). The mechanism of RU486 antagonism is dependent on the conformation of the carboxy-terminal tail of the human progesterone receptor. *Cell* 69, 703-713.

Walters, M. C. et al. (1995). Enhancers increase the probability but not the level of gene expression. *Proc Natl Acad Sci USA* 92, 7125-9.

Wang, Y. et al. (1994). A regulatory system for use in gene transfer. *Proc Natl Acad Sci USA* 91, 8180-4.

Wang, Y. et al. (1997a). Ligand-inducible and liver-specific target gene expression in transgenic mice. *Nat Biotechnol* 15, 239-243.

Wang, Y. et al. (1997b). Positive and negative regulation of gene expression in eukaryotic cells with an inducible transcriptional regulator. *Gene Ther* 4, 432-441.

Westerfield, M. (1995). *The Zebrafish Book: A guide for the laboratory use of Zebrafish (Danio rerio)*, University of Oregon Press, Eugene.

Yamamoto, A. et al. (2001). The ons and offs of inducible transgenic technology: a review. *Neurobiol Dis* 8, 923-32.

Zabner, J. et al. (1994). "Safety and efficacy of repetitive adenovirus-mediated transfer of CFTR cDNA to airway epithelia of primates and cotton rats." *Nature Genetics* 6, 75-83.

Zhang, G. et al. (1996). "An enhanced green fluorescent protein allows sensitive detection of gene transfer in mammalian cells." *Biochem Biophys Res Commun* 227, 707-711.

Zhao, B. et al. (2001). Phenotypic consequences of lung-specific inducible expression of FGF-3. *Proc Natl Acad Sci USA* 98, 5898-903.

Zuo, J. et al. (2000). Technical advance: An estrogen receptor-based transactivator XVE mediates highly inducible gene expression in transgenic plants. *Plant J* 24, 265-273.

Zuo, J. et al. (2001). Chemical-regulated, site-specific DNA excision in transgenic plants. *Nat Biotechnol* 19, 157-161.

What is claimed is:

1. A system useful for preparing a non-human transgenic animal which comprises a first nucleic acid molecule comprising a first DNA construct and a second DNA construct, wherein:
    (a) the first DNA construct encoding a chimeric transcription factor and having the following elements: (i) a DNA encoding a DNA binding domain of a bacterial LexA protein, (ii) a DNA encoding a truncated ligand binding domain of a human progesterone receptor and (iii) a DNA encoding an activation domain of the p65 subunit of human NF-κB, wherein the DNA of (i) comprises the nucleotide sequence set forth in SEQ ID NO:6 and the DNA of (ii) and (iii) comprises the nucleotide sequence set forth in SEQ ID NO:9; and wherein
    (b) the second DNA construct has the following elements in the 5' to 3' direction: (i) a operator comprising LexA binding sites, (ii) a promoter and (iii) a gene, wherein the operator comprises the nucleotide sequence set forth in SEQ ID NO:15.

2. The system of claim 1, wherein a promoter is operatively linked to the first DNA construct encoding the chimeric transcription factor.

3. The system of claim 2, wherein the promoter is a eukaryotic promoter.

4. The system of claim 3, wherein the eukaryotic promoter is a tissue-specific or a cell-specific promoter or an enhancer trap promoter.

5. The system of claim 1, wherein a splice acceptor sequence is operatively linked to the first DNA construct encoding the chimeric transcription factor.

6. The system of claim 1, wherein the gene of the second DNA construct is selected from the group consisting of (i) a gene that is a marker or reporter gene, (ii) a gene that encodes a protein of interest and (iii) a gene that is transcribed into a noncoding RNA.

7. The system of claim 1, wherein the first nucleic acid molecule further comprises a third DNA construct having the following elements in the 5' to 3' direction: (i) a operator comprising LexA binding sites, (ii) a promoter and (iii) a gene, wherein the operator comprises the nucleotide sequence set forth in SEQ ID NO:15.

8. The system of claim 1, which further comprises a second nucleic acid molecule comprising a third DNA construct having the following elements in the 5' to 3' direction: (i) a operator comprising LexA binding sites, (ii) a promoter and (iii) a gene, wherein the operator comprises the nucleotide sequence set forth in SEQ ID NO:15.

9. The system of claim 1, wherein the first nucleic acid molecule further comprises a Dissociator (Ds) 5'-end cis-required sequence and a Ds 3'-end cis-required sequence.

10. The system of claim 8, wherein each of the first nucleic acid molecule and the second nucleic acid molecule further comprises a Dissociator (Ds) 5'-end cis-required sequence and a Ds 3'-end cis-required sequence.

11. The system of claim 7, wherein the first nucleic acid molecule further comprises a Dissociator (Ds) 5'-end cis-required sequence and a Ds 3'-end cis-required sequence.

12. The system of claim 7, wherein the gene of the third DNA construct is selected from the group consisting of (i) a gene that is a marker or reporter gene, (ii) a gene that encodes a protein of interest and (iii) a gene that is transcribed into a noncoding RNA.

13. The system of claim 12, wherein the gene of the second DNA construct is a gene that is a marker or reporter gene and the gene of the third DNA construct is a gene that encodes a protein of interest or a gene that is transcribed into a noncoding RNA.

14. The system of claim 12, wherein the gene of the third DNA construct is a gene that is a marker or reporter gene and the gene of the second DNA construct is a gene that encodes a protein of interest or a gene that is transcribed into a noncoding RNA.

15. The system of claim 8, wherein the gene of the third DNA construct is selected from the group consisting of (i) a gene that is a marker or reporter gene, (ii) a gene that encodes a protein of interest and (iii) a gene that is transcribed into a noncoding RNA.

16. The system of claim 15, wherein the gene of the second DNA construct is a gene that is a marker or reporter gene and the gene of the third DNA construct is a gene that encodes a protein of interest or a gene that is transcribed into a noncoding RNA.

17. The system of claim 15, wherein the gene of the third DNA construct is a gene that is a marker or reporter gene and the gene of the second DNA construct is a gene that encodes a protein of interest or a gene that is transcribed into a noncoding RNA.

* * * * *

SEQUENCE LISTING

```
<160> NUMBER OF SEQ ID NOS: 48

<210> SEQ ID NO 1
<211> LENGTH: 662
<212> TYPE: DNA
<213> ORGANISM: Artificial
<220> FEATURE:
<223> OTHER INFORMATION: pBluescript SK(+) vector DNA

<400> SEQUENCE: 1
cacctaaatt gtaagcgtta atattttgtt aaaattcgcg ttaaattttt gttaaatcag      60 ctcattttt aaccaatagg ccgaaatcgg caaaatccct tataaatcaa aagaatagac      120
cgagataggg ttgagtgttg ttccagtttg gaacaagagt ccactattaa agaacgtgga      180
ctccaacgtc aaagggcgaa aaaccgtcta tcagggcgat ggcccactac gtgaaccatc      240
accctaatca gtttttttgg ggtcgaggtg ccgtaaagca ctaaatcgga accctaaagg      300
gagcccccga tttagagctt gacggggaaa gccggcgaac gtggcgagaa aggaagggaa      360
gaaagcgaaa ggagcgggcg ctagggcgct ggcaagtgta gcggtcacgc tgcgcgtaac      420
caccacaccc gccgcgctta atgcgccgct acagggcgcg tcccattcgc cattcaggct      480
gcgcaactgt tgggaagggc gatcggtgcg ggcctcttcg ctattacgcc agctggcgaa      540 aggggggatgt gctgcaaggc gattaagttg ggtaacgcca gggttttccc agtcacgacg      600
ttgtaaaacg acggccagtg aattgtaata cgactcacta tagggcgaat tgggtacccg      660
ac                                                                    662

<210> SEQ ID NO 2
<211> LENGTH: 236
<212> TYPE: DNA
<213> ORGANISM: Zea mays

<400> SEQUENCE: 2
cagggatgaa agtaggatgg gaaaatcccg taccgaccgt tatcgtataa ccgattttgt      60
tagttttatc ccgatcgatt tcgaacccga ggtaaaaaac gaaaacggaa cggaaacggg      120
atatacaaaa cggtaaacgg aaacggaaac ggtagagcta gtttcccgac cgtttcaccg      180
ggatcccgtt tttaatcggg atgatcccgt ttcgttaccg tattttctaa ttcggc         236

<210> SEQ ID NO 3
<211> LENGTH: 24
<212> TYPE: DNA
<213> ORGANISM: artificial
<220> FEATURE:
<223> OTHER INFORMATION: Synthetic polylinker sequence
```

<400> SEQUENCE: 3

```
gatgactgca acagatccct cgag                                           24
```

<210> SEQ ID NO 4
<211> LENGTH: 565
<212> TYPE: DNA
<213> ORGANISM: Danio rerio

<400> SEQUENCE: 4

```
acaatgcaac tgttcagctc aggggggaaaa atgccctgcc agatccaaac ggctggcaaa    60
agtgaatgga aaaaagcctt tcattaatgt gaaagttgct gcgcgcccca cccagataaa   120
aagagcagag gttaacatgc tctctacggc tgtccagcca accagatact gaggcagaaa   180
cacacccgct ggcagatggt gagagctaca ctgtctttc cagagtttct actggaatgc    240
ctgtcctcaa gtctcaagcc tctccttgca ttctctcatt ccacctgggg caaagcccca   300
ggctgggtgt gacaacattt atcttaccac tttctctctg tacctgtcta acaggtaggg   360
tgtgtgtgag agtgcgtatg tgtgcaagtg cgtgtgtgtg tgagagcagt cagctccacc   420
ctctcaagag tgtgtataaa attggtcagc cagctgctga gagacacgca gagggacttt   480
gactctcctt tgtgagcaac ctcctccact cactcctctc tcagagagca ctctcgtacc   540
tccttctcag caactcaaag acaca                                         565
```

<210> SEQ ID NO 5
<211> LENGTH: 20
<212> TYPE: DNA
<213> ORGANISM: artificial
<220> FEATURE:
<223> OTHER INFORMATION: Synthetic filler DNA sequence

<400> SEQUENCE: 5

```
gggtttatcg gcgcgccacc                                                20
```

<210> SEQ ID NO 6
<211> LENGTH: 297
<212> TYPE: DNA
<213> ORGANISM: Escherichia coli

<400> SEQUENCE: 6

```
atggcaccca agaagaagag gaagatgaaa gcgttaacgg ccaggcaaca agaggtgttt    60
gatctcatcc gtgatcacat cagccagaca ggtatgccgc cgacgcgtgc ggaaatcgcg   120
cagcgtttgg ggttccgttc cccaaacgcg gctgaagaac atctgaaggc gctggcacgc   180
aaaggcgtta ttgaaattgt tccggcgcaa tcacgcggga ttcgtctgtt gcaggaagag   240
gaagaagggt tgccgctggt aggtcgtgtg gctgccggtg aaccgtcgag cgccggt      297
```

<210> SEQ ID NO 7
<211> LENGTH: 24
<212> TYPE: DNA
<213> ORGANISM: Simian virus 40

<400> SEQUENCE: 7

```
atggcaccca agaagaagag gaag                                           24
```

<210> SEQ ID NO 8
<211> LENGTH: 24
<212> TYPE: DNA
<213> ORGANISM: artificial
<220> FEATURE:
<223> OTHER INFORMATION: Synthetic filler DNA sequence

<400> SEQUENCE: 8

```
accgaattcc cgggtgtcga ccag                                          24
```

<210> SEQ ID NO 9
<211> LENGTH: 1641
<212> TYPE: DNA
<213> ORGANISM: Homo sapiens

<400> SEQUENCE: 9

```
aaaaagttca ataaagtcag agttgtgaga gcactggatg ctgttgctct cccacagcca    60
gtgggcgttc caaatgaaag ccaagcccta agccagagat tcactttttc accaggtcaa   120
gacatacagt tgattccacc actgatcaac ctgttaatga gcattgaacc agatgtgatc   180
tatgcaggac atgacaacac aaaacctgac acctccagtt ctttgctgac aagtcttaat   240
caactaggcg agaggcaact tctttcagta gtcaagtggt ctaaatcatt gccaggtttt   300
cgaaacttac atattgatga ccagataact ctcattcagt attcttggat gagcttaatg   360
gtgtttggtc taggatggag atcctacaaa cacgtcagtg ggcagatgct gtattttgca   420
cctgatctaa tactaaatga acagcggatg aaagaatcat cattctattc attatgcctt   480
accatgtggc agatcccaca ggagtttgtc aagcttcaag ttagccaaga agagttcctc   540
tgtatgaaag tattgttact tcttaataca attcctttgg aagggctacg aagtcaaacc   600
cagtttgagg agatgaggtc aagctacatt agagagctca tcaaggcaat tggtttgagg   660
caaaaaggag ttgtgtcgag ctcacagcgt ttctatcaac ttacaaaact tcttgataac   720
ttgcatgatc ttgtcaaaca acttcatctg tactgcttga atacatttat ccagtcccgg   780
gcactgagtg ttgaatttcc agaaatgatg tctgaagtta ttgctgggtc gacgcccatg   840
gaattccagt acctgccaga tacagacgat cgtcaccgga ttgaggagaa acgtaaaagg   900
acatatgaga ccttcaagag catcatgaag aagagtcctt tcagcggacc caccgacccc   960
cggcctccac ctcgacgcat tgctgtgcct tcccgcagct cagcttctgt ccccaagcca  1020
gcacccagc cctatccctt tacgtcatcc ctgagcacca tcaactatga tgagtttccc  1080
accatggtgt ttccttctgg gcagatcagc caggcctcgg ccttggcccc ggcccctccc  1140
caagtcctgc cccaggctcc agccctgcc cctgctccag ccatggtatc agctctggcc  1200
caggccccag cccctgtccc agtcctagcc caggccctc tcaggctgt ggccccacct  1260
gcccccaagc ccacccaggc tggggaagga acgctgtcag aggccctgct gcagctgcag  1320
tttgatgatg aagacctggg ggccttgctt ggcaacagca cagacccagc tgtgttcaca  1380
gacctggcat ccgtcgacaa ctccgagttt cagcagctgc tgaaccaggg catacctgtg  1440
gcccccaca caactgagcc catgctgatg gagtaccctg aggctataac tcgcctagtg  1500
acagggccc agaggccccc cgacccagct cctgctccac tgggggcccc ggggctcccc  1560
aatggcctcc tttcaggaga tgaagacttc tcctccattg cggacatgga cttctcagcc  1620
ctgctgagtc agatcagctc c                                             1641
```

<210> SEQ ID NO 10
<211> LENGTH: 244
<212> TYPE: DNA
<213> ORGANISM: artificial
<220> FEATURE:
<223> OTHER INFORMATION: Simian virus 40 and plasmid pEGFPN1 DNA

<400> SEQUENCE: 10

```
ggcggccggc cgcgactcta gatcataatc agccatacca catttgtaga ggttttactt      60
gctttaaaaa acctcccaca cctccccctg aacctgaaac ataaaatgaa tgcaattgtt     120
gttgttaact tgtttattgc agcttataat ggttacaaat aaagcaatag catcacaaat     180
ttcacaaata aagcattttt ttcactgcat tctagttgtg gtttgtccaa actcatcaat     240
gtat                                                                  244

<210> SEQ ID NO 11
<211> LENGTH: 51
<212> TYPE: DNA
<213> ORGANISM: Simian virus 40

<400> SEQUENCE: 11
aataaagcaa tagcatcaca aatttcacaa ataaagcatt tttttcactg c               51

<210> SEQ ID NO 12
<211> LENGTH: 30
<212> TYPE: DNA
<213> ORGANISM: artificial
<220> FEATURE:
<223> OTHER INFORMATION: Synthetic filler DNA sequence

<400> SEQUENCE: 12
cttaagttta aacgcgttaa caattggaaa                                       30

<210> SEQ ID NO 13
<211> LENGTH: 618
<212> TYPE: DNA
<213> ORGANISM: artificial
<220> FEATURE:
<223> OTHER INFORMATION: Sequence derived from pER10 plasmid

<400> SEQUENCE: 13
ttaagattga atcctgttgc cggtcttgcg atgattatca tataatttct gttgaattac      60
gttaagcatg taataattaa catgtaatgc atgacgttat ttatgagatg ggtttttatg     120
attagagtcc cgcaattata catttaatac gcgatagaaa acaaaatata gcgcgcaaac     180
taggataaat tatcgcgcgc ggtgtcatct atgttactag atcgggaatt gatcccccct     240
cgacagcttg catgccgctt gggctgcagg tcgaggctaa aaaactaatc gcattatcat     300
cccctcgacg tactgtacat ataaccactg gttttatata cagcagtact gtacatataa     360
ccactggttt tatatacagc agtcgacgta ctgtacatat aaccactggt tttatataca     420
gcagtactgt acatataacc actggtttta tatacagcag tcgaggtaag attagatatg     480
gatatgtata tggatatgta tatggtggta atgccatgta atatgctcga ctctaggatc     540
ttcgcaagac ccttcctcta tataaggaag ttcatttcat ttggagagga cacgctgaag     600
ctagtcgact ctagcctc                                                  618

<210> SEQ ID NO 14
<211> LENGTH: 247
<212> TYPE: DNA
<213> ORGANISM: Agrobacterium tumefaciens

<400> SEQUENCE: 14
ttaagattga atcctgttgc cggtcttgcg atgattatca tataatttct gttgaattac      60
gttaagcatg taataattaa catgtaatgc atgacgttat ttatgagatg ggtttttatg     120
attagagtcc cgcaattata catttaatac gcgatagaaa acaaaatata gcgcgcaaac     180
taggataaat tatcgcgcgc ggtgtcatct atgttactag atcgggaatt gatcccccct     240
``` cgacagc                                                                  247

<210> SEQ ID NO 15
<211> LENGTH: 152
<212> TYPE: DNA
<213> ORGANISM: Escherichia coli

<400> SEQUENCE: 15
tactgtacat ataaccactg gttttatata cagcagtact gtacatataa ccactggttt    60
tatatacagc agtcgacgta ctgtacatat aaccactggt tttatataca gcagtactgt   120
acatataacc actggtttta tatacagcag tc                                  152

<210> SEQ ID NO 16
<211> LENGTH: 60
<212> TYPE: DNA
<213> ORGANISM: Cauliflower mosaic virus

<400> SEQUENCE: 16
cttcgcaaga cccttcctct atataaggaa gttcatttca tttggagagg acacgctgaa    60

<210> SEQ ID NO 17
<211> LENGTH: 1012
<212> TYPE: DNA
<213> ORGANISM: artificial
<220> FEATURE:
<223> OTHER INFORMATION: Sequence derived from pEGFPN1

<400> SEQUENCE: 17
gaattctgca gtcgacggta ccgcgggccc gggatccacc ggtcgccacc atggtgagca    60
agggcgagga gctgttcacc ggggtggtgc ccatcctggt cgagctggac ggcgacgtaa   120
acggccacaa gttcagcgtg tccggcgagg gcgagggcga tgccacctac ggcaagctga   180
ccctgaagtt catctgcacc accggcaagc tgcccgtgcc ctggcccacc ctcgtgacca   240
ccctgaccta cggcgtgcag tgcttcagcc gctaccccga ccacatgaag cagcacgact   300
tcttcaagtc cgccatgccc gaaggctacg tccaggagcg caccatcttc ttcaaggacg   360
acggcaacta caagacccgc gccgaggtga agttcgaggg cgacaccctg gtgaaccgca   420
tcgagctgaa gggcatcgac ttcaaggagg acggcaacat cctggggcac aagctggagt   480
acaactacaa cagccacaac gtctatatca tggccgacaa gcagaagaac ggcatcaagg   540
tgaacttcaa gatccgccac aacatcgagg acggcagcgt gcagctcgcc gaccactacc   600
agcagaacac ccccatcggc gacggccccg tgctgctgcc cgacaaccac tacctgagca   660
cccagtccgc cctgagcaaa gaccccaacg agaagcgcga tcacatggtc ctgctggagt   720
tcgtgaccgc cgccgggatc actctcggca tggacgagct gtacaagtaa agcggccgcg   780
actctagatc ataatcagcc ataccacatt tgtagaggtt ttacttgctt taaaaaacct   840
cccacacctc cccctgaacc tgaaacataa aatgaatgca attgttgttg ttaacttgtt   900
tattgcagct tataatggtt acaaataaag caatagcatc acaaatttca caaataaagc   960
atttttttca ctgcattcta gttgtggttt gtccaaactc atcaatacgt ag          1012

<210> SEQ ID NO 18
<211> LENGTH: 717
<212> TYPE: DNA
<213> ORGANISM: artificial
<220> FEATURE:
<223> OTHER INFORMATION: Coding sequence for EGFP derived from pEGFPN1

<400> SEQUENCE: 18

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccctgaccta cggcgtgcag tgcttcagcc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cagccacaac gtctatatca tggccgacaa gcagaagaac   480
ggcatcaagg tgaacttcaa gatccgccac aacatcgagg acggcagcgt gcagctcgcc   540
gaccactacc agcagaacac ccccatcggc gacggccccg tgctgctgcc cgacaaccac   600
tacctgagca cccagtccgc cctgagcaaa gaccccaacg agaagcgcga tcacatggtc   660
ctgctggagt tcgtgaccgc cgccgggatc actctcggca tggacgagct gtacaag     717
```

<210> SEQ ID NO 19
<211> LENGTH: 374
<212> TYPE: DNA
<213> ORGANISM: Zea mays

<400> SEQUENCE: 19

```
agtagactta tatggcttct tatgttagcc aagagcccaa gacttatcac ttatgtgcta    60
cattaaacta tgtgtgctcc agatttatat ggattttatc tatgtttaat taagacttgt   120
gtttacaatt ttttatattt gttttttaagt tttgaatata tgttttcatg tgtgattttta  180
ccgaacaaaa ataccggttc ccgtccgatt tcgactttaa cccgaccgga tcgtatcggt   240
tttcgattac cgtatttatc ccgttcgttt tcgttaccgg tatatcccgt tttcgtttcc   300
gtcccgcaag ttaaatatga aaatgaaaac ggtagaggta ttttaccgac cgttaccgac   360
cgttttcatc ccta                                                     374
```

<210> SEQ ID NO 20
<211> LENGTH: 2210
<212> TYPE: DNA
<213> ORGANISM: artificial
<220> FEATURE:
<223> OTHER INFORMATION: pBluescript SK(+) vector DNA

<400> SEQUENCE: 20

```
gtcggggagc tccagctttt gttcccttta gtgagggtta atttcgagct tggcgtaatc    60
atggtcatag ctgtttcctg tgtgaaattg ttatccgctc acaattccac acaacatacg   120
agccggaagc ataaagtgta aagcctgggg tgcctaatga gtgagctaac tcacattaat   180
tgcgttgcgc tcactgcccg ctttccagtc gggaaacctg tcgtgccagc tgcattaatg   240
aatcggccaa cgcgcgggga gaggcggttt gcgtattggg cgctcttccg cttcctcgct   300
cactgactcg ctgcgctcgg tcgttcggct gcggcgagcg gtatcagctc actcaaaggc   360
ggtaatacgg ttatccacag aatcagggga taacgcagga agaacatgt gagcaaaagg   420
ccagcaaaag gccaggaacc gtaaaaaggc cgcgttgctg gcgttttttcc ataggctccg   480
ccccccctgac gagcatcaca aaaatcgacg ctcaagtcag aggtggcgaa acccgacagg   540
actataaaga taccaggcgt ttccccctgg aagctccctc gtgcgctctc ctgttccgac   600
cctgccgctt accggatacc tgtccgcctt tctcccttcg ggaagcgtgg cgctttctca   660
```

```
tagctcacgc tgtaggtatc tcagttcggt gtaggtcgtt cgctccaagc tgggctgtgt    720
gcacgaaccc cccgttcagc ccgaccgctg cgccttatcc ggtaactatc gtcttgagtc    780
caacccggta agacacgact tatcgccact ggcagcagcc actggtaaca ggattagcag    840
agcgaggtat gtaggcggtg ctacagagtt cttgaagtgg tggcctaact acggctacac    900
tagaaggaca gtatttggta tctgcgctct gctgaagcca gttaccttcg aaaaagagt     960 tggtagctct tgatccggca aacaaaccac cgctggtagc ggtggttttt ttgtttgcaa    1020
gcagcagatt acgcgcagaa aaaaggatc tcaagaagat cctttgatct tttctacggg     1080
gtctgacgct cagtggaacg aaaactcacg ttaagggatt ttggtcatga gattatcaaa    1140
aaggatcttc acctagatcc ttttaaatta aaaatgaagt tttaaatcaa tctaaagtat    1200
atatgagtaa acttggtctg acagttacca atgcttaatc agtgaggcac ctatctcagc    1260
gatctgtcta tttcgttcat ccatagttgc ctgactcccc gtcgtgtaga taactacgat    1320
acgggagggc ttaccatctg gccccagtgc tgcaatgata ccgcgagacc cacgctcacc    1380
ggctccagat ttatcagcaa taaaccagcc agccggaagg gccgagcgca gaagtggtcc    1440
tgcaacttta tccgcctcca tccagtctat taattgttgc cgggaagcta gagtaagtag    1500
ttcgccagtt aatagtttgc gcaacgttgt tgccattgct acaggcatcg tggtgtcacg    1560
ctcgtcgttt ggtatggctt cattcagctc cggttcccaa cgatcaaggc gagttacatg    1620
atcccccatg ttgtgcaaaa aagcggttag ctccttcggt cctccgatcg ttgtcagaag    1680
taagttggcc gcagtgttat cactcatggt tatggcagca ctgcataatt ctcttactgt    1740
catgccatcc gtaagatgct tttctgtgac tggtgagtac tcaaccaagt cattctgaga    1800
atagtgtatg cggcgaccga gttgctcttg cccggcgtca atacgggata ataccgcgcc    1860
acatagcaga actttaaaag tgctcatcat tggaaaacgt tcttcggggc gaaaactctc    1920
aaggatctta ccgctgttga gatccagttc gatgtaaccc actcgtgcac ccaactgatc    1980
ttcagcatct tttactttca ccagcgtttc tgggtgagca aaaacaggaa ggcaaaatgc    2040
cgcaaaaaag ggaataaggg cgacacggaa atgttgaata ctcatactct tcctttttca    2100
atattattga agcatttatc agggttattg tctcatgagc ggatacatat ttgaatgtat    2160
ttagaaaaat aaacaaatag gggttccgcg cacatttccc cgaaaagtgc                2210
```

```
<210> SEQ ID NO 21
<211> LENGTH: 25
<212> TYPE: DNA
<213> ORGANISM: artificial
<220> FEATURE:
<223> OTHER INFORMATION: PCR primer

<400> SEQUENCE: 21
cgcgactcga gcattccacc tgggg                                             25

<210> SEQ ID NO 22
<211> LENGTH: 45
<212> TYPE: DNA
<213> ORGANISM: artificial
<220> FEATURE:
<223> OTHER INFORMATION: PCR primer

<400> SEQUENCE: 22
ggcaacgcgt ttaaaccctg tgtctttgag ttgctgagaa ggagg                       45

<210> SEQ ID NO 23
```

```
<211> LENGTH: 60
<212> TYPE: DNA
<213> ORGANISM: artificial
<220> FEATURE:
<223> OTHER INFORMATION: PCR primer

<400> SEQUENCE: 23
agagggcgcg ccaccatggc acccaagaag aagaggaaga tgaaagcgtt aacggccagg       60

<210> SEQ ID NO 24
<211> LENGTH: 30
<212> TYPE: DNA
<213> ORGANISM: artificial
<220> FEATURE:
<223> OTHER INFORMATION: PCR primer

<400> SEQUENCE: 24
agagggtacc ggcgctcgac ggttcaccgg                                        30

<210> SEQ ID NO 25
<211> LENGTH: 34
<212> TYPE: DNA
<213> ORGANISM: artificial
<220> FEATURE:
<223> OTHER INFORMATION: PCR primer

<400> SEQUENCE: 25
gagaggtacc gaattcccgg gtgtcgacca gaaa                                   34

<210> SEQ ID NO 26
<211> LENGTH: 38
<212> TYPE: DNA
<213> ORGANISM: Artificial
<220> FEATURE:
<223> OTHER INFORMATION: PCR primer

<400> SEQUENCE: 26
gagagcggcc gccttaggag ctgatctgac tcagcagg                               38

<210> SEQ ID NO 27
<211> LENGTH: 36
<212> TYPE: DNA
<213> ORGANISM: Artificial
<220> FEATURE:
<223> OTHER INFORMATION: PCR primer

<400> SEQUENCE: 27
agagagattt aaattaagat tgaatcctgt tgccgg                                 36

<210> SEQ ID NO 28
<211> LENGTH: 37
<212> TYPE: DNA
<213> ORGANISM: Artificial
<220> FEATURE:
<223> OTHER INFORMATION: PCR primer

<400> SEQUENCE: 28
agagagaatt cgaggctaga gtcgactagc ttcagcg                                37

<210> SEQ ID NO 29
<211> LENGTH: 38
<212> TYPE: DNA
<213> ORGANISM: Artificial
<220> FEATURE:
<223> OTHER INFORMATION: PCR primer

<400> SEQUENCE: 29
```

```
agagctcgag caattggtgc tatcatcatg acaaagag                                 38

<210> SEQ ID NO 30
<211> LENGTH: 36
<212> TYPE: DNA
<213> ORGANISM: Artificial
<220> FEATURE:
<223> OTHER INFORMATION: PCR primer

<400> SEQUENCE: 30
agagagttta aactacagct gtgctgggaa ggctgg                                  36

<210> SEQ ID NO 31
<211> LENGTH: 18
<212> TYPE: DNA
<213> ORGANISM: Artificial
<220> FEATURE:
<223> OTHER INFORMATION: Synthetic filler DNA sequence

<400> SEQUENCE: 31
atgactgcaa cagatccc                                                      18

<210> SEQ ID NO 32
<211> LENGTH: 635
<212> TYPE: DNA
<213> ORGANISM: Danio rerio

<400> SEQUENCE: 32
tcgagcaatt ggtgctatca tcatgacaaa gagaaaagaa atcagttatt agaaatgagt        60
tattaaaact attatgatta gaaatatgtt tctttctctt aaacaggatt taaggggaaa       120
atatacaggg agcgaaaaat tttgacttca tctgtatata catataataa ataatacatc       180
aataaattcc atctaaatac gctaccatat atatatatat atgtatatac acacacacac       240
acacaccatc taatatatgt catgctacat tattaacttc agtatgaaat ctactctgct       300
ctggagtgta tcagcgagcg actcctctgc tcggattatc atcacgtgac ctctgacctg       360
aacacagacc tctcttagcc ataggtatac agcctatagc atagagctcg ggctgagagg       420
gaaagtgccg ccgtcagggc tttccattga cagtaaaatg cttacggcct tctgggcgat       480
gcgatgaccc tgcgcttcgg cacggctgaa ctctgatgac ggcgtgtttc tattgtccgc       540
cgcgcgccgc tgtgctgccc ttgccagcgt ataaaagctg cggcagtggt gaggaaggcc       600
agagcgagcc agccttccca gcacagctgt agttt                                  635

<210> SEQ ID NO 33
<211> LENGTH: 54
<212> TYPE: DNA
<213> ORGANISM: artificial
<220> FEATURE:
<223> OTHER INFORMATION: Synthetic sequence containing site for Cre
      recombinase

<400> SEQUENCE: 33
aaacgcgttg ccataacttc gtataggata ctttatacga agttatctgc atgc             54

<210> SEQ ID NO 34
<211> LENGTH: 143
<212> TYPE: DNA
<213> ORGANISM: artificial
<220> FEATURE:
<223> OTHER INFORMATION: Synthetic intron IV8 derived from pGene/V5-HisA

<400> SEQUENCE: 34
```

```
taggttgccg ggaacggtgc attggaacgc gcattcccccg tgttaattaa caggtaagtg      60
tcttcctcct gtttccttcc cctgctattc tgctcaacct tcctatcaga aactgcagta     120
tctgtatttt tgctagggga tcc                                             143
```

<210> SEQ ID NO 35
<211> LENGTH: 727
<212> TYPE: DNA
<213> ORGANISM: artificial
<220> FEATURE:
<223> OTHER INFORMATION: Sequence coding ECFP derived from pECFP1

<400> SEQUENCE: 35

```
cgccaccatg gtgagcaagg gcgaggagct gttcaccggg gtggtgccca tcctggtcga      60
gctggacggc gacgtaaacg ccacaagtt cagcgtgtcc ggcgagggcg agggcgatgc     120
cacctacggc aagctgaccc tgaagttcat ctgcaccacc ggcaagctgc ccgtgccctg     180
gcccaccctc gtgaccaccc tgacctgggg cgtgcagtgc ttcagccgct accccgacca     240
catgaagcag cacgacttct tcaagtccgc catgcccgaa ggctacgtcc aggagcgcac     300
catcttcttc aaggacgacg gcaactacaa gacccgcgcc gaggtgaagt tcgagggcga     360
caccctggtg aaccgcatcg agctgaaggg catcgacttc aaggaggacg gcaacatcct     420
ggggcacaag ctggagtaca actacatcag ccacaacgtc tatatcaccg ccgacaagca     480
gaagaacggc atcaaggcca acttcaagat ccgccacaac atcgaggacg gcagcgtgca     540
gctcgccgac cactaccagc agaacacccc catcggcgac ggccccgtgc tgctgcccga     600
caaccactac ctgagcaccc agtccgccct gagcaaagac cccaacgaga agcgcgatca     660
catggtcctg ctggagttcg tgaccgccgc cgggatcact ctcggcatgg acgagctgta     720
caagtaa                                                              727
```

<210> SEQ ID NO 36
<211> LENGTH: 15
<212> TYPE: DNA
<213> ORGANISM: artificial
<220> FEATURE:
<223> OTHER INFORMATION: Synthetic filler DNA sequence

<400> SEQUENCE: 36

```
agcggccaaa cccgc                                                       15
```

<210> SEQ ID NO 37
<211> LENGTH: 266
<212> TYPE: DNA
<213> ORGANISM: artificial
<220> FEATURE:
<223> OTHER INFORMATION: Sequence coding BGH polyadenylation signal
      derived from pGene/V5-HisA

<400> SEQUENCE: 37

```
tgatcagcct cgactgtgcc ttctagttgc cagccatctg ttgtttgccc ctccccgtg       60 ccttccttga ccctggaagg tgccactccc actgtccttt cctaataaaa tgaggaaatt     120
gcatcgcatt gtctgagtag gtgtcattct attctggggg gtggggtggg gcaggacagc     180 aaggggggagg attgggaaga caatagcagg catgctgggg atgcggtggg ctctatggct     240
tctgaggcgg aaagaaccag cacgtg                                          266
```

<210> SEQ ID NO 38
<211> LENGTH: 39

```
<212> TYPE: DNA
<213> ORGANISM: artificial
<220> FEATURE:
<223> OTHER INFORMATION: Synthetic filler DNA sequence

<400> SEQUENCE: 38
gcgcctaggc cgccgatcgt cgactagtta taatttaaa                           39

<210> SEQ ID NO 39
<211> LENGTH: 31
<212> TYPE: DNA
<213> ORGANISM: artificial
<220> FEATURE:
<223> OTHER INFORMATION: Synthetic filler DNA sequence

<400> SEQUENCE: 39
gaattctgca gtcgacggta ccgcgggccc g                                   31

<210> SEQ ID NO 40
<211> LENGTH: 733
<212> TYPE: DNA
<213> ORGANISM: artificial
<220> FEATURE:
<223> OTHER INFORMATION: Sequence coding mCherry fluorescence protein
      derived from pCS2+mCherry

<400> SEQUENCE: 40
ggatcccgcc accatggtga gcaagggcga ggaggataac atggccatca tcaaggagtt    60
catgcgcttc aaggtgcaca tggagggctc cgtgaacggc cacgagttcg agatcgaggg   120
cgagggcgag ggccgcccct acgagggcac ccagaccgcc aagctgaagg tgaccaaggg   180
tggccccctg cccttcgcct gggacatcct gtcccctcag ttcatgtacg gctccaaggc   240
ctacgtgaag caccccgccg acatccccga ctacttgaag ctgtccttcc ccgagggctt   300
caagtgggag cgcgtgatga acttcgagga cggcggcgtg gtgaccgtga cccaggactc   360
ctccctgcag gacggcgagt tcatctacaa ggtgaagctg cgcggcacca acttcccctc   420
cgacggcccc gtaatgcaga gaagaccat gggctgggag gcctcctccg agcggatgta   480
ccccgaggac ggcgccctga agggcgagat caagcagagg ctgaagctga aggacggcgg   540
ccactacgac gctgaggtca agaccaccta caaggccaag aagcccgtgc agctgcccgg   600
cgcctacaac gtcaacatca gttggacat cacctcccac aacgaggact acaccatcgt   660
ggaacagtac gaacgcgccg agggccgcca ctccaccggc ggcatggacg agctgtacaa   720
gtaaagcggc cgc                                                      733

<210> SEQ ID NO 41
<211> LENGTH: 233
<212> TYPE: DNA
<213> ORGANISM: artificial
<220> FEATURE:
<223> OTHER INFORMATION: Sequence containing SV40 polyadenylation signal
      derived from pEGFPN1

<400> SEQUENCE: 41
gactctagat cataatcagc cataccacat ttgtagaggt tttacttgct ttaaaaaacc    60
tcccacacct ccccctgaac ctgaaacata aaatgaatgc aattgttgtt gttaacttgt   120
ttattgcagc ttataatggt tacaaataaa gcaatagcat cacaaatttc acaaataaag   180
catttttttc actgcattct agttgtggtt tgtccaaact catcaatacg tag          233

<210> SEQ ID NO 42
```

```
<211> LENGTH: 20
<212> TYPE: DNA
<213> ORGANISM: Artificial
<220> FEATURE:
<223> OTHER INFORMATION: oligonucleotide primer

<400> SEQUENCE: 42
aaatcattgc caggttttcg                                              20

<210> SEQ ID NO 43
<211> LENGTH: 20
<212> TYPE: DNA
<213> ORGANISM: Artificial
<220> FEATURE:
<223> OTHER INFORMATION: oligonucleotide primer

<400> SEQUENCE: 43
agcccttcca aaggaattgt                                              20

<210> SEQ ID NO 44
<211> LENGTH: 20
<212> TYPE: DNA
<213> ORGANISM: Artificial
<220> FEATURE:
<223> OTHER INFORMATION: oligonucleotide primer

<400> SEQUENCE: 44
acgtaaacgg ccacaagttc                                              20

<210> SEQ ID NO 45
<211> LENGTH: 20
<212> TYPE: DNA
<213> ORGANISM: Artificial
<220> FEATURE:
<223> OTHER INFORMATION: oligonucleotide primer

<400> SEQUENCE: 45
gtcctccttg aagtcgatgc                                              20

<210> SEQ ID NO 46
<211> LENGTH: 7960
<212> TYPE: DNA
<213> ORGANISM: Artificial
<220> FEATURE:
<223> OTHER INFORMATION: vector construct

<400> SEQUENCE: 46
cacctaaatt gtaagcgtta atattttgtt aaaattcgcg ttaaattttt gttaaatcag     60
ctcatttttt aaccaatagg ccgaaatcgg caaaatccct tataaatcaa agaatagac     120 cgagataggg ttgagtgttg ttccagtttg gaacaagagt ccactattaa agaacgtgga    180
ctccaacgtc aaagggcgaa aaaccgtcta tcagggcgat ggcccactac gtgaaccatc    240
accctaatca agttttttgg ggtcgaggtg ccgtaaagca ctaaatcgga acctaaagg     300 gagcccccga tttagagctt gacggggaaa gccggcgaac gtggcgagaa aggaagggaa    360
gaaagcgaaa ggagcgggcg ctagggcgct ggcaagtgta gcggtcacgc tgcgcgtaac    420
caccacaccc gccgcgctta atgcgccgct acagggcgcg tcccattcgc cattcaggct    480
gcgcaactgt tgggaagggc gatcggtgcg ggcctcttcg ctattacgcc agctggcgaa    540
agggggatgt gctgcaaggc gattaagttg ggtaacgcca gggttttccc agtcacgacg    600
ttgtaaaacg acggccagtg aattgtaata cgactcacta tagggcgaat tgggtacccg    660
accagggatg aaagtaggat gggaaaatcc cgtaccgacc gttatcgtat aaccgatttt    720
```

```
gttagttttta tcccgatcga tttcgaaccc gaggtaaaaa acgaaaacgg aacggaaacg    780
ggatatacaa aacggtaaac ggaaacggaa acggtagagc tagtttcccg accgtttcac    840
cgggatcccg ttttaatcg ggatgatccc gtttcgttac cgtattttct aattcggcga     900
tgactgcaac agatccctcg agacaatgca actgttcagc tcaggggaa aaatgccctg     960
ccagatccaa acggctggca aaagtgaatg gaaaaaagcc tttcattaat gtgaaagttg   1020
ctgcgcgccc cacccagata aaagagcag aggttaacat gctctctacg gctgtccagc   1080
caaccagata ctgaggcaga acacacccg ctggcagatg gtgagagcta cactgtcttt   1140
tccagagttt ctactggaat gcctgtcctc aagtctcaag cctctccttg cattctctca   1200
ttccacctgg ggcaaagccc caggctgggt gtgacaacat ttatcttacc actttctctc   1260
tgtacctgtc taacaggtag ggtgtgtgtg agagtgcgta tgtgtgcaag tgcgtgtgtg   1320
tgtgagagca gtcagctcca ccctctcaag agtgtgtata aaattggtca gccagctgct   1380
gagagacacg cagagggact ttgactctcc tttgtgagca acctcctcca ctcactcctc   1440
tctcagagag cactctcgta cctccttctc agcaactcaa agacacaggg tttatcggcg   1500
cgccaccatg gcacccaaga agaagaggaa gatgaaagcg ttaacggcca ggcaacaaga   1560
ggtgtttgat ctcatccgtg atcacatcag ccagacaggt atgccgccga cgcgtgcgga   1620
aatcgcgcag cgtttggggt tccgttcccc aaacgcggct gaagaacatc tgaaggcgct   1680
ggcacgcaaa ggcgttattg aaattgtttc cggcgcatca cgcgggattc gtctgttgca   1740
ggaagaggaa gaagggttgc cgctggtagg tcgtgtggct gccggtgaac cgtcgagcgc   1800
cggtaccgaa ttcccggtgt cgaccagaa aaagttcaat aaagtcagag ttgtgagagc   1860
actggatgct gttgctctcc cacagccagt gggcgttcca aatgaaagcc aagccctaag   1920
ccagagattc acttttcac caggtcaaga catacagttg attccaccac tgatcaacct   1980
gttaatgagc attgaaccag atgtgatcta tgcaggacat gacaacacaa aacctgacac   2040
ctccagttct ttgctgacaa gtcttaatca actaggcgag aggcaacttc tttcagtagt   2100
caagtggtct aaatcattgc caggtttttcg aaacttacat attgatgacc agataactct   2160
cattcagtat tcttggatga gcttaatggt gtttggtcta ggatggagat cctacaaaca   2220
cgtcagtggg cagatgctgt attttgcacc tgatctaata ctaaatgaac agcggatgaa   2280
agaatcatca ttctattcat tatgccttac catgtggcag atcccacagg agtttgtcaa   2340
gcttcaagtt agccaagaag agttcctctg tatgaaagta ttgttacttc ttaatacaat   2400
tccttttggaa gggctacgaa gtcaaaccca gtttgaggag atgaggtcaa gctacattag   2460
agagctcatc aaggcaattg gtttgaggca aaaggagtt gtgtcgagct cacagcgttt   2520
ctatcaactt acaaaacttc ttgataactt gcatgatctt gtcaaacaac ttcatctgta   2580
ctgcttgaat acatttatcc agtcccgggc actgagtgtt gaatttccag aaatgatgtc   2640
tgaagttatt gctgggtcga cgcccatgga attccagtac tgccagata cagacgatcg   2700
tcaccggatt gaggagaaac gtaaaaggac atatgagacc ttcaagagca tcatgaagaa   2760
gagtcctttc agcggaccca ccgaccccg gcctccacct cgacgcattg ctgtgccttc   2820
ccgcagctca gcttctgtcc ccaagccagc accccagccc tatccctta cgtcatccct   2880
gagcaccatc aactatgatg agtttcccac catggtgttt ccttctgggc agatcagcca   2940
ggcctcgggc ttggccccgg cccctcccca gtcctgccc caggctccag ccctgcccc    3000
tgctccagcc atggtatcag ctctggccca ggccccagcc cctgtcccag tcctagcccc   3060
```

```
aggccctcct caggctgtgg ccccacctgc ccccaagccc acccaggctg ggaaggaac    3120 gctgtcagag gccctgctgc agctgcagtt tgatgatgaa gacctggggg ccttgcttgg   3180
caacagcaca gacccagctg tgttcacaga cctggcatcc gtcgacaact ccgagtttca   3240
gcagctgctg aaccagggca tacctgtggc cccccacaca actgagccca tgctgatgga   3300
gtaccctgag gctataactc gcctagtgac agggcccag  aggcccccg  acccagctcc    3360 tgctccactg ggggcccgg  ggctccccaa tggcctcctt tcaggagatg aagacttctc   3420
ctccattgcg gacatggact tctcagccct gctgagtcag atcagctcct aaggcggccg   3480
gccgcgactc tagatcataa tcagccatac acatttgta gaggttttac ttgctttaaa    3540
aaacctccca cacctccccc tgaacctgaa acataaaatg aatgcaattg ttgttgttaa   3600
cttgtttatt gcagcttata atggttacaa ataaagcaat agcatcacaa atttcacaaa   3660
taaagcattt ttttcactgc attctagttg tggtttgtcc aaactcatca atgtatctta   3720
agtttaaacg cgttaacaat tggaaattaa gattgaatcc tgttgccggt cttgcgatga   3780
ttatcatata atttctgttg aattacgtta agcatgtaat aattaacatg taatgcatga   3840
cgttatttat gagatgggtt tttatgatta gagtcccgca attatacatt taatacgcga   3900
tagaaaacaa aatatagcgc gcaaactagg ataaattatc gcgcgcggtg tcatctatgt   3960
tactagatcg ggaattgatc cccctcgac  agcttgcatg ccgcttgggc tgcaggtcga   4020
ggctaaaaaa ctaatcgcat tatcatcccc tcgacgtact gtacatataa ccactggttt   4080
tatatacagc agtactgtac atataaccac tggttttata tacagcagtc gacgtactgt   4140
acatataacc actggtttta tatacagcag tactgtacat ataaccactg gttttatata   4200
cagcagtcga ggtaagatta gatatggata tgtatatgga tatgtatatg gtggtaatgc   4260
catgtaatat gctcgactct aggatcttcg caagacccct cctctatata aggaagttca   4320
tttcatttgg agaggacacg ctgaagctag tcgactctag cctcgaattc tgcagtcgac   4380
ggtaccgcgg gccgggatc  caccggtcgc caccatggtg agcaagggcg aggagctgtt   4440
caccggggtg gtgcccatcc tggtcgagct ggacggcgac gtaaacggcc acaagttcag   4500
cgtgtccggc gagggcgagg gcgatgccac ctacggcaag ctgaccctga agttcatctg   4560
caccaccggc aagctgcccg tgccctggcc caccctcgtg accaccctga cctacggcgt   4620
gcagtgcttc agccgctacc ccgaccacat gaagcagcac gacttcttca gtccgccat    4680 gcccgaaggc tacgtccagg agcgcaccat cttcttcaag gacgacggca actacaagac   4740
ccgcgccgag gtgaagttcg agggcgacac cctggtgaac cgcatcgagc tgaagggcat   4800
cgacttcaag gaggacggca acatcctggg gcacaagctg gagtacaact acaacagcca   4860
caacgtctat atcatggccg acaagcagaa gaacggcatc aaggtgaact tcaagatccg   4920
ccacaacatc gaggacggca gcgtgcagct cgccgaccac taccagcaga cacccccat    4980 cggcgacggc cccgtgctgc tgcccgacaa ccactacctg agcacccagt ccgccctgag   5040
caaagacccc aacgagaagc gcgatcacat ggtcctgctg gagttcgtga ccgccgccgg   5100
gatcactctc ggcatggacg agctgtacaa gtaaagcggc cgcgactcta gatcataatc   5160
agccatacca catttgtaga ggttttactt gctttaaaaa acctcccaca cctcccctg    5220 aacctgaaac ataaaatgaa tgcaattgtt gttgttaact tgtttattgc agcttataat   5280
ggttacaaat aaagcaatag catcacaaat ttcacaaata aagcattttt ttcactgcat   5340
tctagttgtg gtttgtccaa actcatcaat acgtagagta gacttatatg gcttcttatg   5400
ttagccaaga gcccaagact tatcacttat gtgctacatt aaactatgtg tgctccagat   5460
```

```
ttatatggat tttatctatg tttaattaag acttgtgttt acaatttttt atatttgttt    5520
ttaagttttg aatatatgtt ttcatgtgtg attttaccga acaaaaatac cggttcccgt    5580
ccgatttcga ctttaacccg accggatcgt atcggttttc gattaccgta tttatcccgt    5640
tcgttttcgt taccggtata tcccgttttc gtttccgtcc cgcaagttaa atatgaaaat    5700
gaaaacggta gaggtatttt accgaccgtt accgaccgtt ttcatcccta gtcggggagc    5760
tccagctttt gttcccttta gtgagggtta atttcgagct tggcgtaatc atggtcatag    5820
ctgtttcctg tgtgaaattg ttatccgctc acaattccac acaacatacg agccggaagc    5880
ataaagtgta aagcctgggg tgcctaatga gtgagctaac tcacattaat tgcgttgcgc    5940
tcactgcccg ctttccagtc gggaaacctg tcgtgccagc tgcattaatg aatcggccaa    6000
cgcgcgggga gaggcggttt gcgtattggg cgctcttccg cttcctcgct cactgactcg    6060
ctgcgctcgg tcgttcggct gcggcgagcg gtatcagctc actcaaaggc ggtaatacgg    6120
ttatccacag aatcagggga taacgcagga aagaacatgt gagcaaaagg ccagcaaaag    6180
gccaggaacc gtaaaaaggc cgcgttgctg gcgtttttcc ataggctccg ccccccctgac   6240
gagcatcaca aaaatcgacg ctcaagtcag aggtggcgaa acccgacagg actataaaga    6300
taccaggcgt ttccccctgg aagctccctc gtgcgctctc ctgttccgac cctgccgctt    6360
accggatacc tgtccgcctt tctcccttcg ggaagcgtgg cgctttctca tagctcacgc    6420
tgtaggtatc tcagttcggt gtaggtcgtt cgctccaagc tgggctgtgt gcacgaaccc    6480
cccgttcagc ccgaccgctg cgccttatcc ggtaactatc gtcttgagtc aacccggta    6540
agacacgact tatcgccact ggcagcagcc actggtaaca ggattagcag agcgaggtat    6600
gtaggcggtg ctacagagtt cttgaagtgg tggcctaact acggctacac tagaaggaca    6660
gtatttggta tctgcgctct gctgaagcca gttaccttcg gaaaaagagt tggtagctct    6720
tgatccggca acaaaccac cgctggtagc ggtggttttt ttgtttgcaa gcagcagatt     6780
acgcgcagaa aaaaaggatc tcaagaagat cctttgatct tttctacggg gtctgacgct    6840
cagtggaacg aaaactcacg ttaagggatt ttggtcatga gattatcaaa aaggatcttc    6900
acctagatcc ttttaaatta aaaatgaagt tttaaatcaa tctaaagtat atatgagtaa    6960
acttggtctg acagttacca atgcttaatc agtgaggcac ctatctcagc gatctgtcta    7020
tttcgttcat ccatagttgc ctgactcccc gtcgtgtaga taactacgat acgggagggc    7080
ttaccatctg gccccagtgc tgcaatgata ccgcgagacc cacgctcacc ggctccagat    7140
ttatcagcaa taaaccagcc agccggaagg gccgagcgca gaagtggtcc tgcaacttta    7200
tccgcctcca tccagtctat taattgttgc cgggaagcta gagtaagtag ttcgccagtt    7260
aatagtttgc gcaacgttgt tgccattgct acaggcatcg tggtgtcacg ctcgtcgttt    7320
ggtatggctt cattcagctc cggttcccaa cgatcaaggc gagttacatg atcccccatg    7380
ttgtgcaaaa aagcggttag ctccttcggt cctccgatcg ttgtcagaag taagttggcc    7440
gcagtgttat cactcatggt tatggcagca ctgcataatt ctcttactgt catgccatcc    7500
gtaagatgct tttctgtgac tggtgagtac tcaaccaagt cattctgaga atagtgtatg    7560
cggcgaccga gttgctcttg cccggcgtca atacgggata ataccgcgcc acatagcaga    7620
actttaaaag tgctcatcat tggaaaacgt tcttcgggge gaaaactctc aaggatctta    7680
ccgctgttga gatccagttc gatgtaaccc actcgtgcac ccaactgatc ttcagcatct    7740
tttactttca ccagcgtttc tgggtgagca aaaacaggaa ggcaaaatgc cgcaaaaaag    7800
```

```
ggaataaggg cgacacggaa atgttgaata ctcatactct tccttttca atattattga    7860 agcatttatc agggttattg tctcatgagc ggatacatat ttgaatgtat ttagaaaaat    7920
aaacaaatag gggttccgcg cacatttccc cgaaaagtgc                          7960

<210> SEQ ID NO 47
<211> LENGTH: 6994
<212> TYPE: DNA
<213> ORGANISM: Artificial
<220> FEATURE:
<223> OTHER INFORMATION: vector construct

<400> SEQUENCE: 47
cacctaaatt gtaagcgtta atattttgtt aaaattcgcg ttaaattttt gttaaatcag      60 ctcattttt aaccaatagg ccgaaatcgg caaaatccct tataaatcaa agaatagac      120 cgagataggg ttgagtgttg ttccagtttg gaacaagagt ccactattaa agaacgtgga    180
ctccaacgtc aaagggcgaa aaaccgtcta tcagggcgat ggcccactac gtgaaccatc    240
accctaatca agttttttgg ggtcgaggtg ccgtaaagca ctaaatcgga acctaaaagg    300
gagcccccga tttagagctt gacggggaaa gccggcgaac gtggcgagaa aggaagggaa    360
gaaagcgaaa ggagcgggcg ctagggcgct ggcaagtgta gcggtcacgc tgcgcgtaac    420
caccacaccc gccgcgctta atgcgccgct acagggcgcg tcccattcgc cattcaggct    480
gcgcaactgt tgggaagggc gatcggtgcg ggcctcttcg ctattacgcc agctggcgaa    540 aggggggatgt gctgcaaggc gattaagttg ggtaacgcca gggttttccc agtcacgacg    600
ttgtaaaacg acggccagcg cgcgtaatac gactcactat agggcgaatt gggtacccga    660
cgcagggatg aaagtaggat gggaaaatcc cgtaccgacc gttatcgtat aaccgattttt   720 gttagtttta tcccgatcga tttcgaaccc gaggtaaaaa acgaaaacgg aacgaaaacg    780
ggatatacaa aacggtaaac ggaaacggaa acggtagagc tagtttcccg accgtttcac    840
cgggatcccg ttttaatcg gatgatcccc gtttcgttac cgtatttttct aattcgggat    900 gactgcaaca gatccctcga gcaattggtg ctatcatcat gacaaagaga aagaaatca    960 gttattagaa atgagttatt aaaactatta tgattgaaaa tatgtttctt tctcttaaac   1020
aggatttaag gggaaaatat acagggagcg aaaaattttg acttcatctg tatatacata   1080
taataaataa tacatcaata aattccatct aaatacgcta ccatatata atatatatgt    1140 atatacacac acacacacac accatctaat atatgtcatg ctacattatt aacttcagta   1200
tgaaatctac tctgctctgg agtgtatcag cgagcgactc ctctgctcgg attatcatca   1260
cgtgacctct gacctgaaca cagacctctc ttagccatag gtatacagcc tatagcatag   1320
agctcgggct gagagggaaa gtgccgccgt cagggctttc cattgacagt aaaatgctta   1380
cggccttctg ggcgatgcga tgaccctgcg cttcggcacg gctgaactct gatgacggcg   1440
tgtttctatt gtccgccgcg cgccgctgtg ctgcccttgc cagcgtataa agctgcggc    1500 agtggtgagg aaggccagag cgagccagcc ttcccagcac agctgtagtt taaacgcgtt   1560
gccataactt cgtataggat actttatacg aagttatctg catgctaggt tgccgggaac   1620
ggtgcattgg aacgcgcatt cccgtgttta ttaacaggt aagtgtcttc ctcctgtttc    1680
cttcccctgc tattctgctc aaccttccta tcagaaactg cagtatctgt attttgcta   1740 ggggatcccg ccaccatggt gagcaagggc gaggagctgt tcaccggggt ggtgcccatc    1800
ctggtcgagc tggacggcga cgtaaacggc cacaagttca gcgtgtccgg cgagggcgag   1860
ggcgatgcca cctacggcaa gctgaccctg aagttcatct gcaccaccgg caagctgccc   1920
```

```
gtgccctggc ccaccctcgt gaccaccctg acctggggcg tgcagtgctt cagccgctac    1980
cccgaccaca tgaagcagca cgacttcttc aagtccgcca tgcccgaagg ctacgtccag    2040
gagcgcacca tcttcttcaa ggacgacggc aactacaaga cccgcgccga ggtgaagttc    2100
gagggcgaca ccctggtgaa ccgcatcgag ctgaagggca tcgacttcaa ggaggacggc    2160
aacatcctgg ggcacaagct ggagtacaac tacatcagcc acaacgtcta tatcaccgcc    2220
gacaagcaga agaacggcat caaggccaac ttcaagatcc gccacaacat cgaggacggc    2280
agcgtgcagc tcgccgacca ctaccagcag aacacccca tcggcgacgg ccccgtgctg    2340
ctgcccgaca accactacct gagcacccag tccgccctga gcaaagaccc caacgagaag    2400
cgcgatcaca tggtcctgct ggagttcgtg accgccgccg ggatcactct cggcatggac    2460
gagctgtaca agtaaagcgg ccaaacccgc tgatcagcct cgactgtgcc ttctagttgc    2520
cagccatctg ttgtttgccc ctcccccgtg ccttccttga ccctggaagg tgccactccc    2580
actgtccttt cctaataaaa tgaggaaatt gcatcgcatt gtctgagtag gtgtcattct    2640
attctggggg gtgggtggg gcaggacagc aaggggagg attgggaaga caatagcagg    2700
catgctgggg atgcggtggg ctctatggct tctgaggcgg aaagaaccag cacgtggcgc    2760
ctaggccgcc gatcgtcgac tagttataat ttaaattaag attgaatcct gttgccggtc    2820
ttgcgatgat tatcatataa tttctgttga attacgttaa gcatgtaata attaacatgt    2880
aatgcatgac gttatttatg agatgggttt ttatgattag agtcccgcaa ttatacattt    2940
aatacgcgat agaaaacaaa atatagcgcg caaactagga taaattatcg cgcgcggtgt    3000
catctatgtt actagatcgg gaattgatcc ccctcgaca gcttgcatgc cgcttgggct    3060
gcaggtcgag gctaaaaaac taatcgcatt atcatcccct cgacgtactg tacatataac    3120
cactggtttt atatacagca gtactgtaca tataaccact ggttttatat acagcagtcg    3180
acgtactgta catataacca ctggttttat atacagcagt actgtacata taaccactgg    3240
ttttatatac agcagtcgag gtaagattag atatggatat gtatatggat atgtatatgg    3300
tggtaatgcc atgtaatatg ctcgactcta ggatcttcgc aagacccttc ctctatataa    3360
ggaagttcat ttcatttgga gaggacacgc tgaagctagt cgactctagc ctcgaattct    3420
gcagtcgacg gtaccgcggg cccgggatcc cgccaccatg gtgagcaagg gcgaggagga    3480
taacatggcc atcatcaagg agttcatgcg cttcaaggtg cacatggagg gctccgtgaa    3540
cggccacgag ttcgagatcg agggcgaggg cgagggccgc ccctacgagg cacccagac    3600 cgccaagctg aaggtgacca aggtggccc ctgcccttc gctgggaca tcctgtcccc    3660 tcagttcatg tacggctcca aggcctacgt gaagcacccc gccgacatcc ccgactactt    3720
gaagctgtcc ttccccgagg gcttcaagtg ggagcgcgtg atgaacttcg aggacggcgg    3780
cgtggtgacc gtgacccagg actcctccct gcaggacggc gagttcatct acaaggtgaa    3840
gctgcgcggg accaacttcc cctccgacgg ccccgtaatg cagaagaaga ccatgggctg    3900
ggaggcctcc tccgagcgga tgtaccccga ggacggcgcc ctgaagggcg agatcaagca    3960
gaggctgaag ctgaaggacg gcggccacta cgacgctgag gtcaagacca cctacaaggc    4020
caagaagccc gtgcagctgc ccggcgccta caacgtcaac atcaagttgg acatcacctc    4080
ccacaacgag gactacacca tcgtggaaca gtacgaacgc gccgagggcc gccactccac    4140
cggcggcatg gacgagctgt acaagtaaag cggccgcgac tctagatcat aatcagccat    4200
accacatttg tagaggtttt acttgcttta aaaaacctcc cacacctccc cctgaacctg    4260
```

```
aaacataaaa tgaatgcaat tgttgttgtt aacttgttta ttgcagctta taatggttac    4320
aaataaagca atagcatcac aaatttcaca aataaagcat ttttttcact gcattctagt    4380
tgtggtttgt ccaaactcat caatacgtag agtagactta tatggcttct tatgttagcc    4440
aagagcccaa gacttatcac ttatgtgcta cattaaacta tgtgtgctcc agatttatat    4500
ggattttatc tatgtttaat taagacttgt gtttacaatt ttttatattt gttttttaagt   4560 tttgaatata tgttttcatg tgtgatttta ccgaacaaaa ataccggttc ccgtccgatt    4620
tcgactttaa cccgaccgga tcgtatcggt tttcgattac cgtatttatc ccgttcgttt    4680
tcgttaccgg tatatcccgt tttcgttttcc gtcccgcaag ttaaatatga aaatgaaaac   4740
ggtagaggta ttttaccgac cgttaccgac cgttttcatc cctagtcggg gagctccagc    4800
ttttgttccc tttagtgagg gttaatttcg agcttggcgt aatcatggtc atagctgttt    4860
cctgtgtgaa attgttatcc gctcacaatt ccacacaaca tacgagccgg aagcataaag    4920
tgtaaagcct ggggtgccta atgagtgagc taactcacat taattgcgtt gcgctcactg    4980
cccgctttcc agtcgggaaa cctgtcgtgc cagctgcatt aatgaatcgg ccaacgcgcg    5040
gggagaggcg gtttgcgtat tgggcgctct tccgcttcct cgctcactga ctcgctgcgc    5100
tcggtcgttc ggctgcggcg agcggtatca gctcactcaa aggcggtaat acggttatcc    5160
acagaatcag gggataacgc aggaaagaac atgtgagcaa aaggccagca aaaggccagg    5220
aaccgtaaaa aggccgcgtt gctggcgttt ttccataggc tccgcccccc tgacgagcat    5280
cacaaaaatc gacgctcaag tcagaggtgg cgaaacccga caggactata aagataccag    5340
gcgtttcccc ctggaagctc cctcgtgcgc tctcctgttc cgaccctgcc gcttaccgga    5400
tacctgtccg cctttctccc ttcgggaagc gtggcgcttt ctcatagctc acgctgtagg    5460
tatctcagtt cggtgtaggt cgttcgctcc aagctgggct gtgtgcacga accccccgtt    5520
cagcccgacc gctgcgcctt atccggtaac tatcgtcttg agtccaaccc ggtaagacac    5580
gacttatcgc cactggcagc agccactggt aacaggatta gcagagcgag gtatgtaggc    5640
ggtgctacag agttcttgaa gtggtggcct aactacggct acactagaag gacagtattt    5700
ggtatctgcg ctctgctgaa gccagttacc ttcggaaaaa gagttggtag ctcttgatcc    5760
ggcaaacaaa ccaccgctgg tagcggtggt ttttttgttt gcaagcagca gattacgcgc    5820
agaaaaaaag gatctcaaga agatcctttg atcttttcta cggggtctga cgctcagtgg    5880
aacgaaaact cacgttaagg gattttggtc atgagattat caaaaaggat cttcacctag    5940 atcctttaa attaaaaatg aagttttaaa tcaatctaaa gtatatatga gtaaacttgg    6000
tctgacagtt accaatgctt aatcagtgag gcacctatct cagcgatctg tctatttcgt    6060
tcatccatag ttgcctgact ccccgtcgtg tagataacta cgatacggga gggcttacca    6120
tctggcccca gtgctgcaat gataccgcga gacccacgct caccggctcc agatttatca    6180
gcaataaacc agccagccgg aagggccgag cgcagaagtg gtcctgcaac tttatccgcc    6240
tccatccagt ctattaattg ttgccgggaa gctagagtaa gtagttcgcc agttaatagt    6300
ttgcgcaacg ttgttgccat tgctacaggc atcgtggtgt cacgctcgtc gtttggtatg    6360
gcttcattca gctccggttc ccaacgatca aggcgagtta catgatcccc catgttgtgc    6420
aaaaaagcgg ttagctcctt cggtcctccg atcgttgtca agtaagtt  ggccgcagtg    6480 ttatcactca tggttatggc agcactgcat aattctctta ctgtcatgcc atccgtaaga    6540
tgcttttctg tgactggtga gtactcaacc aagtcattct gagaatagtg tatgcggcga    6600
ccgagttgct cttgcccggc gtcaatacgg gataataccg cgccacatag cagaacttta    6660
```

```
aaagtgctca tcattggaaa acgttcttcg gggcgaaaac tctcaaggat cttaccgctg    6720
ttgagatcca gttcgatgta acccactcgt gcacccaact gatcttcagc atcttttact    6780
ttcaccagcg tttctgggtg agcaaaaaca ggaaggcaaa atgccgcaaa aagggaata    6840 agggcgacac ggaaatgttg aatactcata ctcttccttt ttcaatatta ttgaagcatt    6900
tatcagggtt attgtctcat gagcggatac atatttgaat gtatttagaa aaataaacaa    6960 atagggggttc cgcgcacatt tccccgaaaa gtgc                                6994
```

<210> SEQ ID NO 48
<211> LENGTH: 8535
<212> TYPE: DNA
<213> ORGANISM: Artificial
<220> FEATURE:
<223> OTHER INFORMATION: Vector construct

<400> SEQUENCE: 48

```
cacctaaatt gtaagcgtta atattttgtt aaaattcgcg ttaaattttt gttaaatcag      60
ctcatttttt aaccaatagg ccgaaatcgg caaaatccct tataaatcaa agaatagac     120 cgagataggg ttgagtgttg ttccagtttg gaacaagagt ccactattaa agaacgtgga    180
ctccaacgtc aaagggcgaa aaaccgtcta tcagggcgat ggcccactac gtgaaccatc    240
accctaatca agttttttgg ggtcgaggtg ccgtaaagca ctaaatcgga acccctaaagg    300 gagcccccga tttagagctt gacggggaaa gccggcgaac gtggcgagaa aggaagggaa    360
gaaagcgaaa ggagcgggcg ctagggcgct ggcaagtgta gcggtcacgc tgcgcgtaac    420
caccacaccc gccgcgctta atgcgccgct acagggcgcg tcccattcgc cattcaggct    480
gcgcaactgt tgggaagggc gatcggtgcg ggcctcttcg ctattacgcc agctggcgaa    540
agggggatgt gctgcaaggc gattaagttg ggtaacgcca gggttttccc agtcacgacg    600
ttgtaaaacg acggccagtg aattgtaata cgactcacta taggggcgaat tgggtacccg    660 accagggatg aaagtaggat gggaaaatcc cgtaccgacc gttatcgtat aaccgatttt    720
gttagtttta tcccgatcga tttcgaaccc gaggtaaaaa acgaaaacgg aacgaaaacg    780
ggatatacaa aacggtaaac ggaaacggaa acggtagagc tagtttcccg accgtttcac    840
cgggatcccg ttttttaatcg ggatgatccc gtttcgttac cgtattttct aattcggcga    900
tgactgcaac agatccctcg agacaatgca actgttcagc tcaggggaa aaatgccctg    960 ccagatccaa acggctggca aaagtgaatg gaaaaagcc tttcattaat gtgaaagttg    1020
ctgcgcgccc cacccagata aaagagcag aggttaacat gctctctacg gctgtccagc    1080
caaccagata ctgaggcaga aacacacccg ctggcagatg gtgagagcta cactgtcttt    1140
tccagagttt ctactggaat gcctgtcctc aagtctcaag cctctccttg cattctctca    1200
ttccacctgg ggcaaagccc caggctgggt gtgacaacat ttatcttacc actttctctc    1260
tgtacctgtc taacaggtag ggtgtgtgtg agagtgcgta tgtgtgcaag tgcgtgtgtg    1320
tgtgagagca gtcagctcca ccctctcaag agtgtgtata aaattggtca gccagctgct    1380
gagagacacg cagagggact ttgactctcc tttgtgagca acctcctcca ctcactcctc    1440
tctcagagag cactctcgta cctccttctc agcaactcaa agacacaggg tttatcggcg    1500
cgccaccatg gcacccaaga agaaggagaa gatgaaagcg ttaacggcca ggcaacaaga    1560
ggtgtttgat ctcatccgtg atcacatcag ccagacaggt atgccgccga cgcgtgcgga    1620
aatcgcgcag cgtttggggt tccgttcccc aaacgcggct gaagaacatc tgaaggcgct    1680
```

```
ggcacgcaaa ggcgttattg aaattgtttc cggcgcatca cgcgggattc gtctgttgca   1740
ggaagaggaa gaagggttgc cgctggtagg tcgtgtggct gccggtgaac cgtcgagcgc   1800
cggtaccgaa ttcccggtg  tcgaccagaa aaagttcaat aaagtcagag ttgtgagagc   1860
actggatgct gttgctctcc cacagccagt gggcgttcca aatgaaagcc aagccctaag   1920
ccagagattc acttttcac  caggtcaaga catacagttg attccaccac tgatcaacct   1980
gttaatgagc attgaaccag atgtgatcta tgcaggacat gacaacacaa aacctgacac   2040
ctccagttct ttgctgacaa gtcttaatca actaggcgag aggcaacttc tttcagtagt   2100
caagtggtct aaatcattgc caggttttcg aaacttacat attgatgacc agataaactct  2160 cattcagtat tcttggatga gcttaatggt gtttggtcta ggatggagat cctacaaaca   2220
cgtcagtggg cagatgctgt attttgcacc tgatctaata ctaaatgaac agcggatgaa   2280
agaatcatca ttctattcat tatgccttac catgtggcag atcccacagg agtttgtcaa   2340
gcttcaagtt agccaagaag agttcctctg tatgaaagta ttgttacttc ttaatacaat   2400
tcctttggaa gggctacgaa gtcaaaccca gtttgaggag atgaggtcaa gctacattag   2460
agagctcatc aaggcaattg gtttgaggca aaaggagtt  gtgtcgagct cacagcgttt   2520
ctatcaactt acaaaacttc ttgataactt gcatgatctt gtcaaacaac ttcatctgta   2580
ctgcttgaat acatttatcc agtcccgggc actgagtgtt gaatttccag aaatgatgtc   2640
tgaagttatt gctgggtcga cgcccatgga attccagtac ctgccagata cagacgatcg   2700
tcaccggatt gaggagaaac gtaaaaggac atatgagacc ttcaagagca tcatgaagaa   2760
gagtcctttc agcggaccca ccgaccccg  gcctccacct cgacgcattg ctgtgccttc   2820
ccgcagctca gcttctgtcc ccaagccagc accccagccc tatccctta  cgtcatccct   2880 gagcaccatc aactatgatg agtttcccac catggtgttt ccttctgggc agatcagcca   2940
ggcctcggcc ttggccccgg cccctcccca gtcctgccc  caggctccag cccctgcccc   3000
tgctccagcc atggtatcag ctctggccca ggccccagcc cctgtcccag tcctagcccc   3060
aggccctcct caggctgtgg ccccacctgc ccccaagccc acccaggctg gggaaggaac   3120
gctgtcagag gccctgctgc agctgcagtt tgatgatgaa gacctggggg ccttgcttgg   3180
caacagcaca gacccagctg tgttcacaga cctggcatcc gtcgacaact ccgagtttca   3240
gcagctgctg aaccagggca tacctgtggc cccccacaca actgagccca tgctgatgga   3300
gtaccctgag gctataactc gcctagtgac aggggcccag aggcccccg  acccagctcc   3360 tgctccactg ggggcccgg  ggctcccaa  tggcctcctt tcaggagatg aagacttctc   3420
ctccattgcg gacatggact tctcagccct gctgagtcag atcagctcct aaggcggccg   3480
gccgcgactc tagatcataa tcagccatac cacatttgta gaggttttac ttgctttaaa   3540
aaacctccca cacctccccc tgaacctgaa acataaaatg aatgcaattg ttgttgttaa   3600
cttgtttatt gcagcttata atggttacaa ataaagcaat agcatcacaa atttcacaaa   3660
taaagcattt ttttcactgc attctagttg tggtttgtcc aaactcatca atgtatctta   3720
agtttaaacg cgttaacaat tggaaattaa gattgaatcc tgttgccggt cttgcgatga   3780
ttatcatata atttctgttg aattacgtta agcatgtaat aattaacatg taatgcatga   3840
cgttatttat gagatgggtt tttatgatta gagtcccgca attatacatt taatacgcga   3900
tagaaaacaa aatatagcgc gcaaactagg ataaattatc gcgcgcggtg tcatctatgt   3960
tactagatcg ggaattgatc cccctcgac  agcttgcatg ccgcttgggc tgcaggtcga   4020
ggctaaaaaa ctaatcgcat tatcatcccc tcgacgtact gtacatataa ccactggttt   4080
```

```
tatatacagc agtactgtac atataaccac tggttttata tacagcagtc gacgtactgt    4140
acatataacc actggtttta tatacagcag tactgtacat ataaccactg gttttatata    4200
cagcagtcga ggtaagatta gatatggata tgtatatgga tatgtatatg gtggtaatgc    4260
catgtaatat gctcgactct aggatcttcg caagacccTt cctctatata aggaagttca    4320
tttcatttgg agaggacacg ctgaagctag tcgactctag cctcgaattc tgcagtcgac    4380
ggtaccgcgg gcccgggatc caccggtcgc caccatggtg agcaagggcg aggagctgtt    4440
caccggggtg gtgcccatcc tggtcgagct ggacggcgac gtaaacggcc acaagttcag    4500
cgtgtccggc gagggcgagg gcgatgccac ctacggcaag ctgaccctga agttcatctg    4560
caccaccggc aagctgcccg tgccctggcc caccctcgtg accaccctga cctacggcgt    4620
gcagtgcttc agccgctacc ccgaccacat gaagcagcac gacttcttca gtccgccat    4680 gcccgaaggc tacgtccagg agcgcaccat cttcttcaag gacgacggca actacaagac    4740
ccgcgccgag gtgaagttcg agggcgacac cctggtgaac cgcatcgagc tgaagggcat    4800
cgacttcaag gaggacggca acatcctggg gcacaagctg gagtacaact acaacagcca    4860
caacgtctat atcatggccg acaagcagaa gaacggcatc aaggtgaact tcaagatccg    4920
ccacaacatc gaggacggca gcgtgcagct cgccgaccac taccagcaga caccccat     4980 cggcgacggc cccgtgctgc tgcccgacaa ccactacctg agcacccagt ccgccctgag    5040
caaagacccc aacgagaagc gcgatcacat ggtcctgctg gagttcgtga ccgccgccgg    5100
gatcactctc ggcatggacg agctgtacaa gttaagcggc ggcatgaccg aatataagct    5160
tgtggtcgtg ggagctgtag gcgtaggcaa aagcgctctc accatccaac tcatccagaa    5220
ccactttgtg gatgaatatg acccgactat agaggactcg tacaggaagc aggtggtgat    5280
tgacggagag acgtgtctac tggacatcct ggacactgca ggtcaggagg agtacagtgc    5340
catgagggac cagtacatga ggacaggaga gggcttcctc tgtgtctttg ccatcaataa    5400
caccaagtcc ttcgaggaca ttcaccacta cagggagcag ataaagcgag taaaggactc    5460
tgaggacgtc cccatggttc tggtggggaa taagtgtgat cttcagtccc acaatgtgga    5520
ctccaaacag gctcaggatt tagcacgcag ctacggcatc ccatttatag agacctcagc    5580
aaagacaaga cagggtgtgg acgacgcgtt ttatactta gtccgagaaa tccggaaaca    5640
caaggagaag atgagcaagg agggcaaaaa gaaaaagaag aaatccaaaa caaaatgtgc    5700
attaatgtga gcggccgcga ctctagatca taatcagcca taccacattt gtagaggttt    5760
tacttgcttt aaaaaacctc ccacacctcc cctgaacct gaaacataaa atgaatgcaa    5820
ttgttgttgt taacttgttt attgcagctt ataatggtta caaataaagc aatagcatca    5880
caaatttcac aaataaagca tttttttcac tgcattctag ttgtggtttg tccaaactca    5940
tcaatacgta gagtagactt atatggcttc ttatgttagc caagagccca agacttatca    6000
cttatgtgct acattaaact atgtgtgctc cagattata tggatttat ctatgtttaa    6060 ttaagacttg tgtttacaat tttttatatt tgttttaag ttttgaatat atgttttcat    6120
gtgtgatttt accgaacaaa ataccggtt cccgtccgat tcgacttta acccgaccgg    6180 atcgtatcgg ttttcgatta ccgtatttat cccgttcgtt ttcgttaccg gtatatcccg    6240
ttttcgtttc cgtcccgcaa gttaaatatg aaaatgaaaa cggtagaggt attttaccga    6300
ccgttaccga ccgttttcat ccctagtcgg ggagctccag cttttgttcc ctttagtgag    6360
ggttaatttc gagcttggcg taatcatggt catagctgtt tcctgtgtga aattgttatc    6420
```

```
cgctcacaat tccacacaac atacgagccg aagcataaa gtgtaaagcc tggggtgcct    6480
aatgagtgag ctaactcaca ttaattgcgt tgcgctcact gcccgctttc cagtcgggaa    6540
acctgtcgtg ccagctgcat taatgaatcg gccaacgcgc ggggagaggc ggtttgcgta    6600
ttgggcgctc ttccgcttcc tcgctcactg actcgctgcg ctcggtcgtt cggctgcggc    6660
gagcggtatc agctcactca aaggcggtaa tacggttatc cacagaatca ggggataacg    6720
caggaaagaa catgtgagca aaaggccagc aaaaggccag gaaccgtaaa aaggccgcgt    6780
tgctggcgtt tttccatagg ctccgccccc ctgacgagca tcacaaaaat cgacgctcaa    6840
gtcagaggtg gcgaaacccg acaggactat aaagatacca ggcgtttccc cctggaagct    6900
ccctcgtgcg ctctcctgtt ccgaccctgc cgcttaccgg atacctgtcc gcctttctcc    6960
cttcgggaag cgtggcgctt tctcatagct cacgctgtag gtatctcagt tcggtgtagg    7020
tcgttcgctc caagctgggc tgtgtgcacg aaccccccgt tcagcccgac cgctgcgcct    7080
tatccggtaa ctatcgtctt gagtccaacc cggtaagaca cgacttatcg ccactggcag    7140
cagccactgg taacaggatt agcagagcga ggtatgtagg cggtgctaca gagttcttga    7200
agtggtggcc taactacggc tacactagaa ggacagtatt tggtatctgc gctctgctga    7260
agccagttac cttcggaaaa agagttggta gctcttgatc cggcaaacaa accaccgctg    7320
gtagcggtgg ttttttttgtt tgcaagcagc agattacgcg cagaaaaaaa ggatctcaag    7380
aagatccttt gatcttttct acggggtctg acgctcagtg gaacgaaaac tcacgttaag    7440
ggattttggt catgagatta tcaaaaagga tcttcaccta gatccttttta aattaaaaat    7500 gaagttttaa atcaatctaa agtatatatg agtaaacttg gtctgacagt taccaatgct    7560
taatcagtga ggcacctatc tcagcgatct gtctatttcg ttcatccata gttgcctgac    7620
tccccgtcgt gtagataact acgatacggg agggcttacc atctggcccc agtgctgcaa    7680
tgataccgcg agacccacgc tcaccggctc cagatttatc agcaataaac cagccagccg    7740
gaagggccga gcgcagaagt ggtcctgcaa ctttatccgc ctccatccag tctattaatt    7800
gttgccggga agctagagta agtagttcgc cagttaatag tttgcgcaac gttgttgcca    7860
ttgctacagg catcgtggtg tcacgctcgt cgtttggtat ggcttcattc agctccggtt    7920
cccaacgatc aaggcgagtt acatgatccc ccatgttgtg caaaaaagcg gttagctcct    7980
tcggtcctcc gatcgttgtc agaagtaagt tggccgcagt gttatcactc atggttatgg    8040
cagcactgca taattctctt actgtcatgc catccgtaag atgcttttct gtgactggtg    8100
agtactcaac caagtcattc tgagaatagt gtatgcggcg accgagttgc tcttgcccgg    8160
cgtcaatacg ggataatacc gcgccacata gcagaacttt aaaagtgctc atcattggaa    8220
aacgttcttc ggggcgaaaa ctctcaagga tcttaccgct gttgagatcc agttcgatgt    8280
aacccactcg tgcacccaac tgatcttcag catcttttac tttcaccagc gtttctgggt    8340
gagcaaaaac aggaaggcaa aatgccgcaa aaaagggaat aagggcgaca cggaaatgtt    8400
gaatactcat actcttcctt tttcaatatt attgaagcat ttatcagggt tattgtctca    8460
tgagcggata catatttgaa tgtatttaga aaaataaaca ataggggtt ccgcgcacat    8520 ttccccgaaa agtgc                                                    8535
```